(12) United States Patent
Richardson et al.

(10) Patent No.: US 12,402,924 B2
(45) Date of Patent: *Sep. 2, 2025

(54) BONE REPAIR DEVICES AND METHODS

(71) Applicant: CircumFIx Solutions, Inc., Piperton, TN (US)

(72) Inventors: Kenneth Walter Richardson, Piperton, TN (US); Louis A. Houff, Piperton, TN (US); Jacob H. Carroll, Oakland, TN (US)

(73) Assignee: CircumFIx Solutions, Inc., Piperton, TN (US)

( * ) Notice: Subject to any disclaimer, the term of this patent is extended or adjusted under 35 U.S.C. 154(b) by 388 days.

This patent is subject to a terminal disclaimer.

(21) Appl. No.: 17/875,147

(22) Filed: Jul. 27, 2022

(65) Prior Publication Data

US 2023/0034375 A1    Feb. 2, 2023

Related U.S. Application Data

(60) Provisional application No. 63/227,060, filed on Jul. 29, 2021.

(51) Int. Cl.
*A61B 17/80*      (2006.01)

(52) U.S. Cl.
CPC ........ *A61B 17/808* (2013.01); *A61B 17/8076* (2013.01)

(58) Field of Classification Search
CPC ... A61B 17/82; A61B 17/823; A61B 17/8861; A61B 17/8863; A61B 17/8869; A61B 17/808
See application file for complete search history.

(56) References Cited

U.S. PATENT DOCUMENTS

| 1,950,799 A | 3/1934 | Jones |
| 4,119,091 A | 10/1978 | Partridge |
| (Continued) | | |

FOREIGN PATENT DOCUMENTS

| JP | S62270147 A | 11/1987 |
| JP | 2003515571 A1 | 5/2003 |
| (Continued) | | |

OTHER PUBLICATIONS

International Search Report and Written Opinion issued in International Application No. PCT/US2023/019867 dated Nov. 7, 2023.

(Continued)

*Primary Examiner* — Si Ming Ku
(74) *Attorney, Agent, or Firm* — Nelson Mullins Riley & Scarborough LLP

(57) ABSTRACT

A plate assembly for stabilizing a bone is provided. The plate assembly includes a fixation plate having rails that form a window. The plate assembly includes a band having a tail and a head. The head defines an internal cavity configured to receive a portion of the tail. The fixation plate is configured to be positioned proximate to a bone. The head is configured to be at least partially received within the window. Further, the band is configured to be wrapped around the fixation plate and the bone, and the internal cavity of the head is configured to receive an end of the tail to form a loop. The band is configured to receive a tension force to tighten the loop formed by the band. The band may passively engage the fixation plate so that bands may be easily removed from windows when no tension is applied to the band.

19 Claims, 72 Drawing Sheets

(56) References Cited

U.S. PATENT DOCUMENTS

| | | | |
|---|---|---|---|
| 4,262,391 A | 4/1981 | Peash | |
| 4,730,615 A | 3/1988 | Sutherland et al. | |
| 4,896,668 A | 1/1990 | Popoff et al. | |
| 5,139,498 A | 8/1992 | Astudillo Ley | |
| 5,190,545 A * | 3/1993 | Corsi | A61B 17/842 |
| | | | 606/916 |
| 5,324,291 A | 6/1994 | Ries et al. | |
| 5,330,489 A | 7/1994 | Green et al. | |
| 5,607,430 A | 3/1997 | Bailey | |
| 5,665,089 A | 9/1997 | Dall et al. | |
| 5,702,399 A | 12/1997 | Kilpela et al. | |
| 5,722,976 A | 3/1998 | Brown | |
| 5,741,259 A | 4/1998 | Chan | |
| 5,941,881 A | 8/1999 | Barnes | |
| 6,387,099 B1 | 5/2002 | Lange et al. | |
| 7,033,377 B2 | 4/2006 | Miller, III | |
| 7,229,444 B2 | 6/2007 | Boyd | |
| 7,537,596 B2 | 5/2009 | Jensen | |
| 7,648,504 B2 | 1/2010 | Heino et al. | |
| 8,460,295 B2 | 6/2013 | McClellan et al. | |
| 8,512,379 B2 | 8/2013 | Heino et al. | |
| 8,674,457 B2 | 3/2014 | Toh et al. | |
| 8,758,348 B2 | 6/2014 | McClellan et al. | |
| 8,888,791 B2 | 11/2014 | Jaramillo et al. | |
| 8,974,457 B2 | 3/2015 | McClellan et al. | |
| 9,023,058 B2 | 5/2015 | Jaramillo et al. | |
| 9,474,553 B2 | 10/2016 | Koch | |
| 9,585,705 B2 * | 3/2017 | Koch | A61B 17/1691 |
| 9,597,132 B2 | 3/2017 | Houff | |
| 9,700,363 B2 | 7/2017 | Jaramillo et al. | |
| 10,070,904 B2 | 9/2018 | Madjarov et al. | |
| 10,154,864 B2 | 12/2018 | Houff | |
| 10,716,608 B2 | 7/2020 | Beyersdorf et al. | |
| 10,758,290 B2 | 9/2020 | Detweiler et al. | |
| 10,786,294 B2 | 9/2020 | Martinez-Ferro et al. | |
| 11,033,308 B2 | 6/2021 | Stecco et al. | |
| 11,241,264 B2 | 2/2022 | Houff | |
| 2002/0177853 A1 | 11/2002 | Chervitz et al. | |
| 2007/0038218 A1 | 2/2007 | Grevious | |
| 2007/0123883 A1 | 5/2007 | Ellis et al. | |
| 2008/0208205 A1 | 8/2008 | Kraemer | |
| 2009/0105717 A1 | 4/2009 | Bluechel | |
| 2009/0287215 A1 | 11/2009 | Fisher et al. | |
| 2010/0094294 A1 | 4/2010 | Gillard et al. | |
| 2010/0211075 A1 | 8/2010 | Stone | |
| 2011/0035008 A1 | 2/2011 | Williams | |
| 2011/0087295 A1 | 4/2011 | Kubiak et al. | |
| 2011/0106153 A1 | 5/2011 | Stone et al. | |
| 2011/0295257 A1 | 12/2011 | McClellan et al. | |
| 2011/0313435 A1 | 12/2011 | Aldridge et al. | |
| 2012/0041441 A1 | 2/2012 | Bernstein et al. | |
| 2012/0059424 A1 | 3/2012 | Epperly et al. | |
| 2012/0089193 A1 | 4/2012 | Stone et al. | |
| 2012/0221060 A1 | 8/2012 | Blain | |
| 2013/0165933 A1 | 6/2013 | Gephart | |
| 2013/0172944 A1 | 7/2013 | Fritizinger et al. | |
| 2013/0289564 A1 | 10/2013 | Bernstein et al. | |
| 2013/0296930 A1 | 11/2013 | Belson et al. | |
| 2014/0148863 A1 | 5/2014 | Barsoum et al. | |
| 2014/0155895 A1 | 6/2014 | McClellan et al. | |
| 2014/0171945 A1 | 6/2014 | Reese | |
| 2014/0243905 A1 | 8/2014 | Cavalazzi et al. | |
| 2014/0309699 A1 | 10/2014 | Houff | |
| 2014/0378976 A1 | 12/2014 | Garcia | |
| 2015/0045794 A1 | 2/2015 | Garcia et al. | |
| 2016/0000483 A1 | 1/2016 | Stone | |
| 2017/0281232 A1 | 10/2017 | Smith et al. | |
| 2019/0099207 A1 | 4/2019 | Houff | |
| 2020/0078063 A1 | 3/2020 | Garcia et al. | |

FOREIGN PATENT DOCUMENTS

| | | | |
|---|---|---|---|
| JP | 2005137757 A | 6/2005 | |
| JP | 2010535553 A | 11/2010 | |
| WO | 2009021876 A2 | 2/2009 | |
| WO | 2012114360 A1 | 8/2012 | |
| WO | 2013003719 A1 | 1/2013 | |

OTHER PUBLICATIONS

The International Search Report and the Written Opinion for PCT/US2014/011187, dated Apr. 4, 2014; 10 Pages.

The International Search Report and the Written Opinion for PCT/US2014/015875, dated May 6, 2014; 10 Pages.

Communication pursuant to Article 94(3) EPC; Examination Report; Oct. 25, 2016; 7 pages.

The International Search Report and Written Opinion for PCT/US2021/038246, dated Oct. 13, 2021; 11 pages.

International Search Report and Written Opinion for International application No. PCT/US2022/038478; dated Nov. 14, 2022; 16 pages.

* cited by examiner

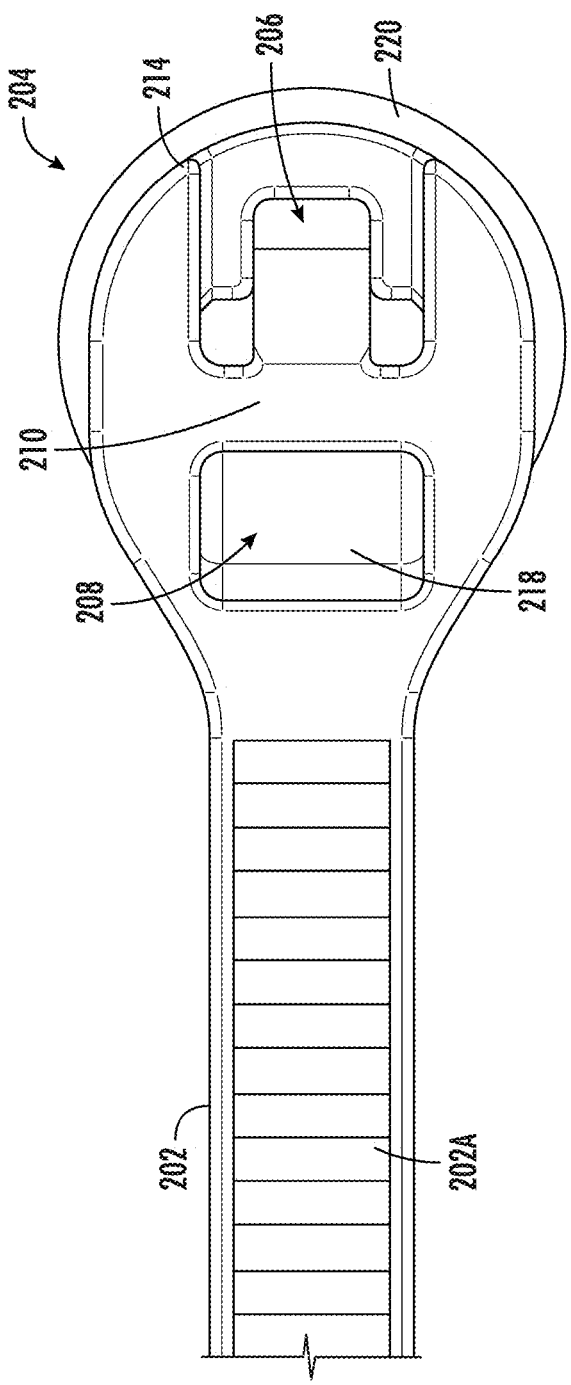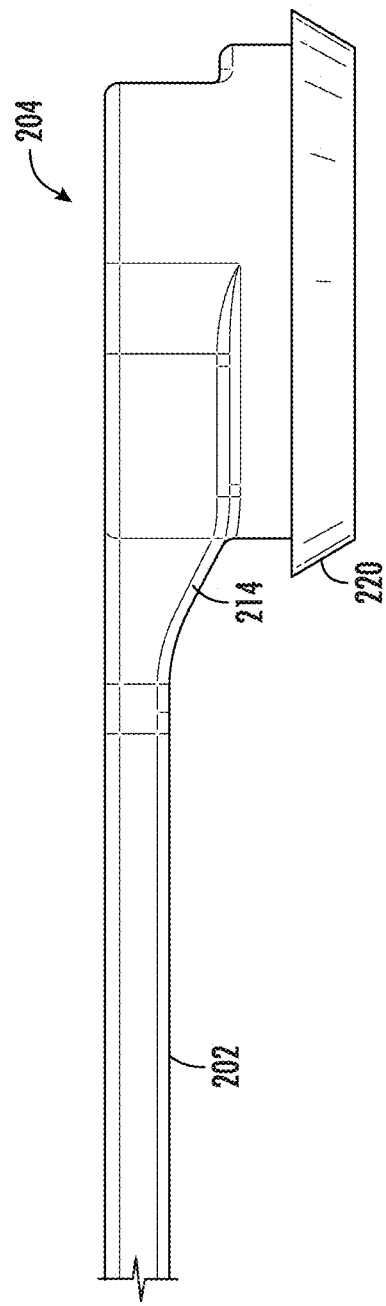
FIG. 2A
FIG. 2B

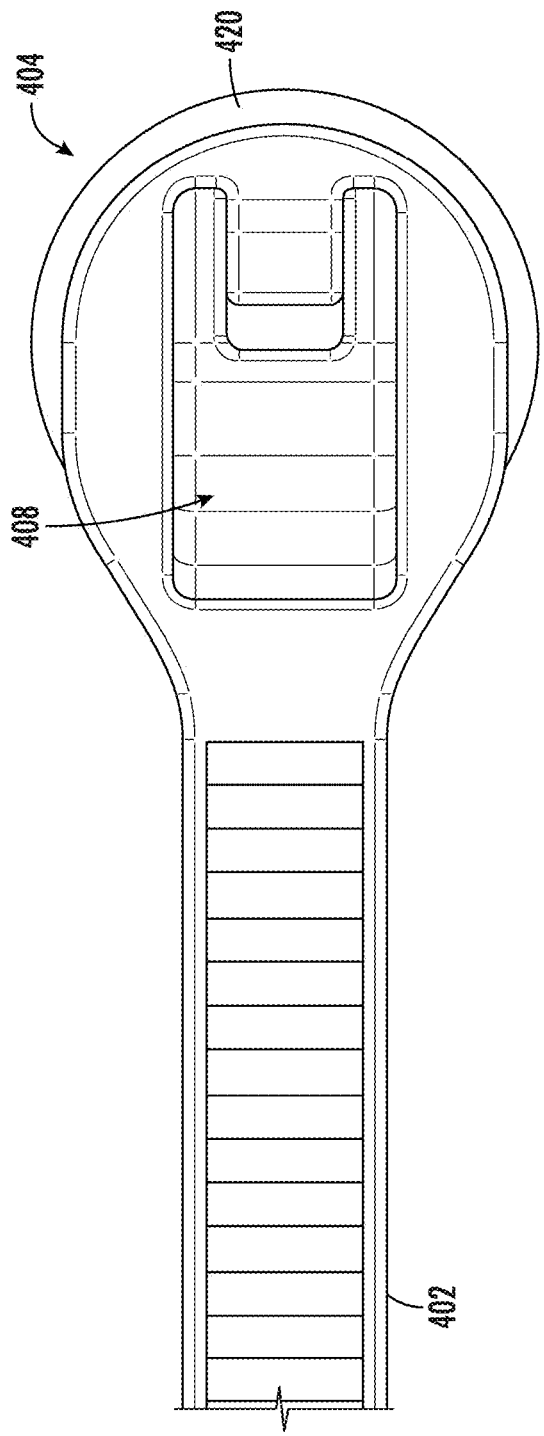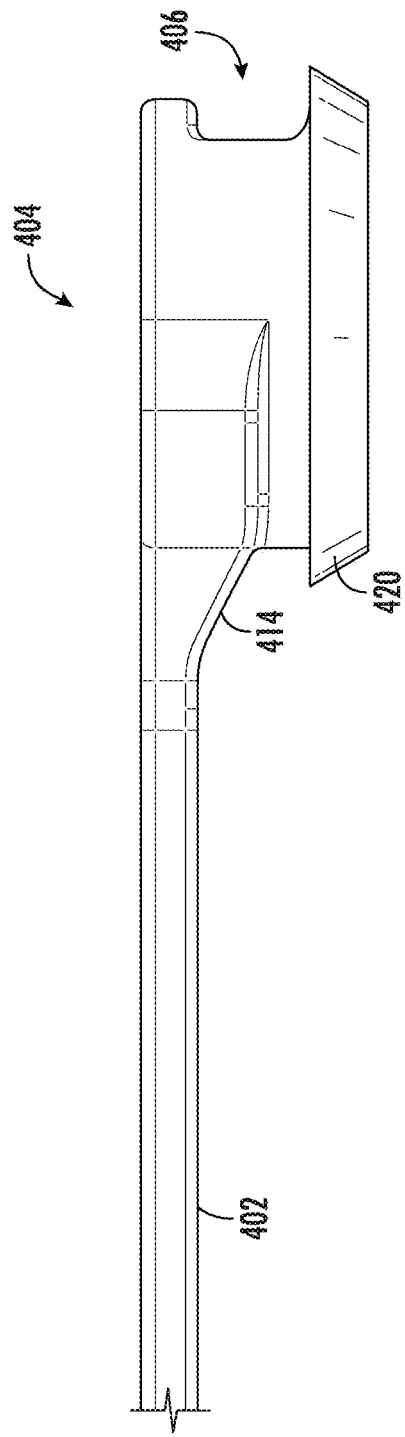
FIG. 4A
FIG. 4B

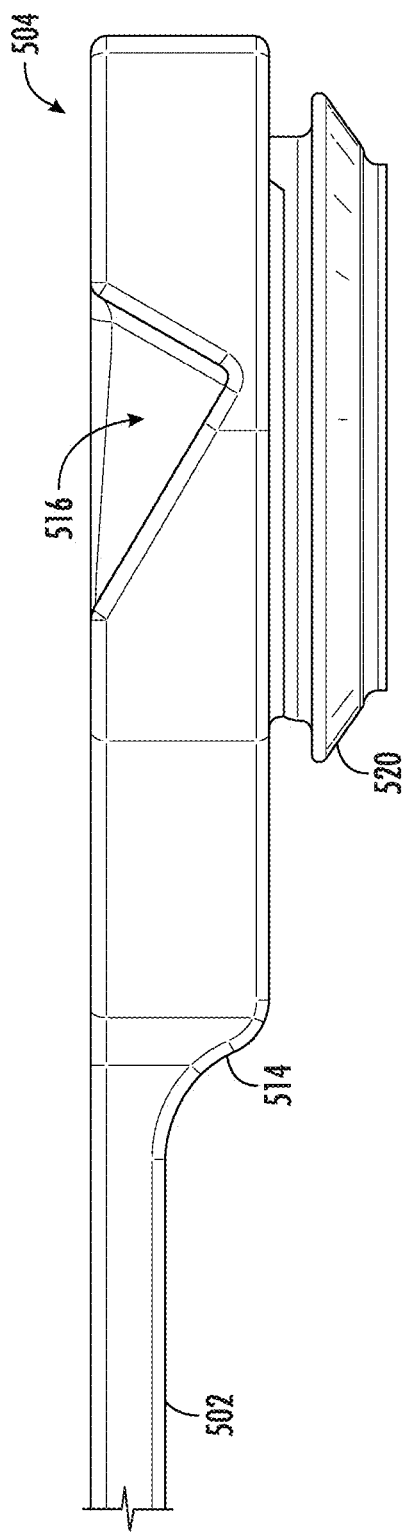
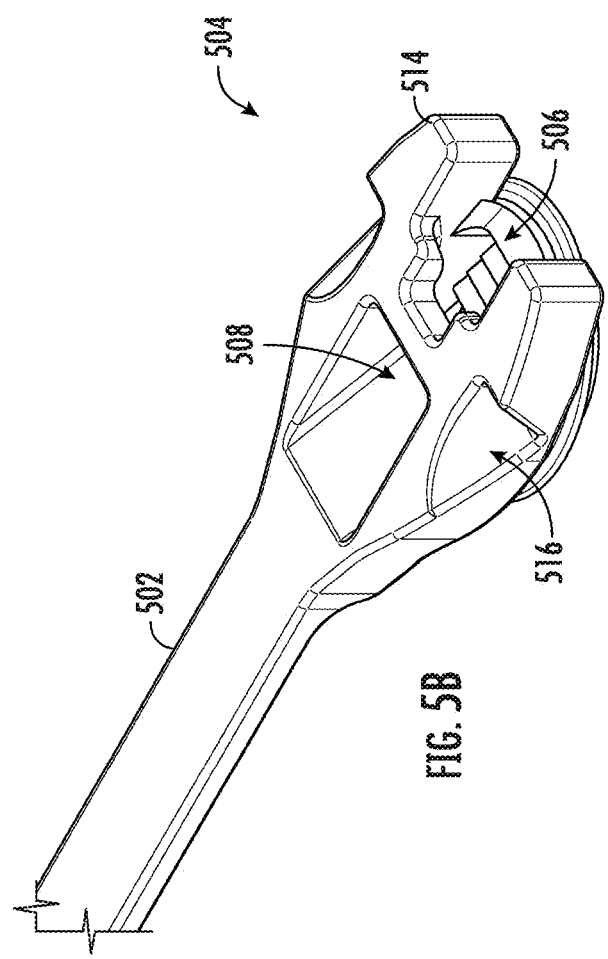
FIG. 5A
FIG. 5B

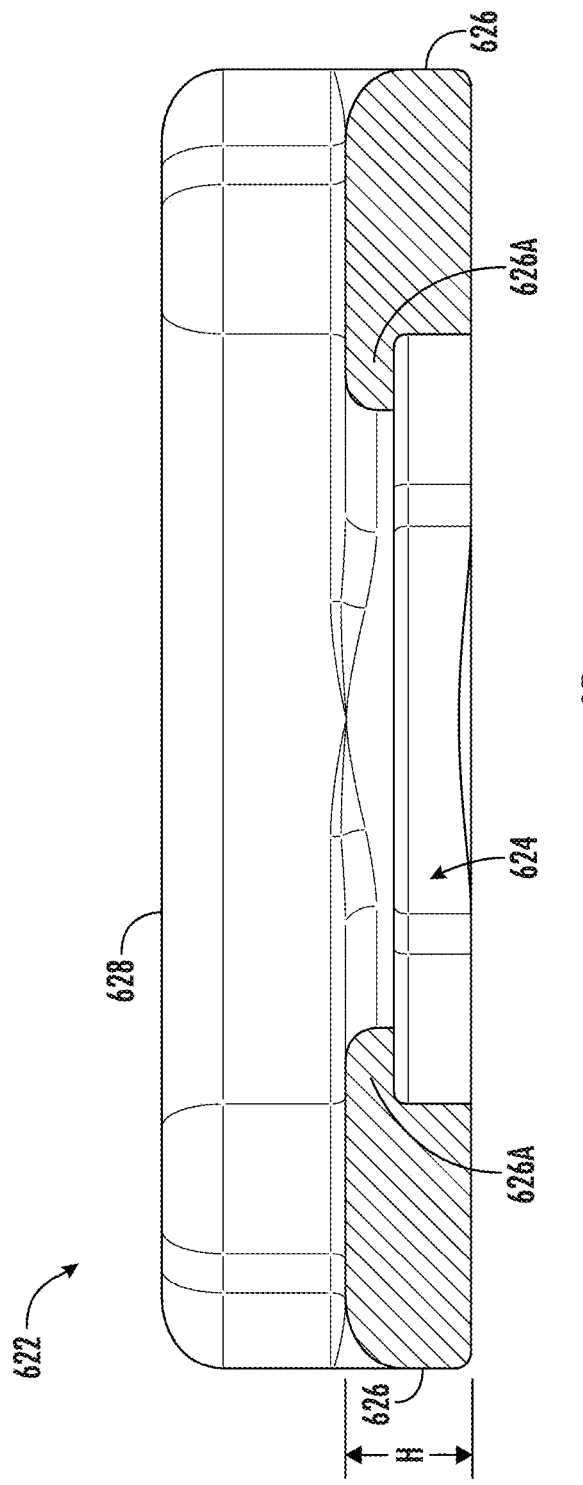

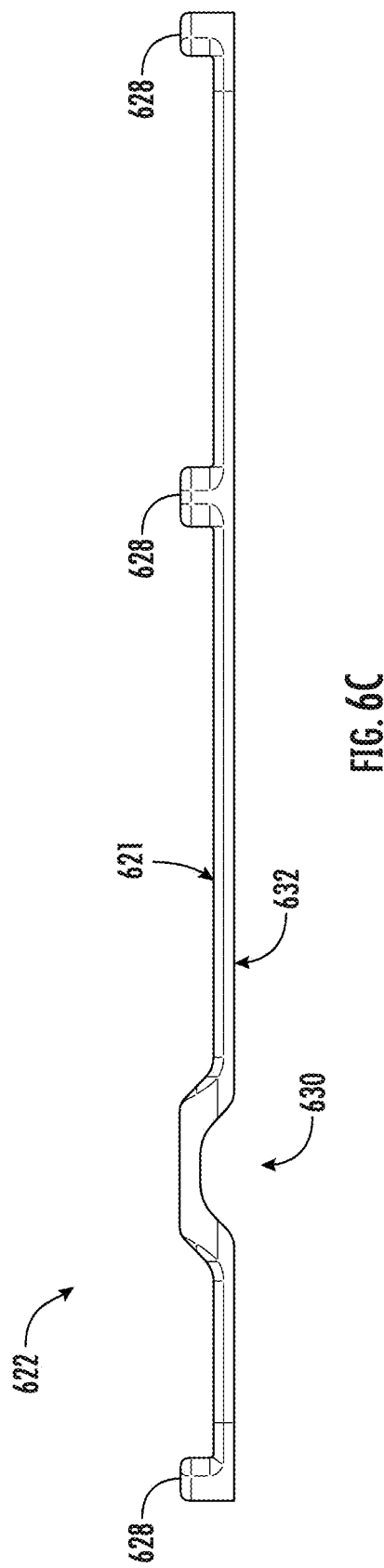

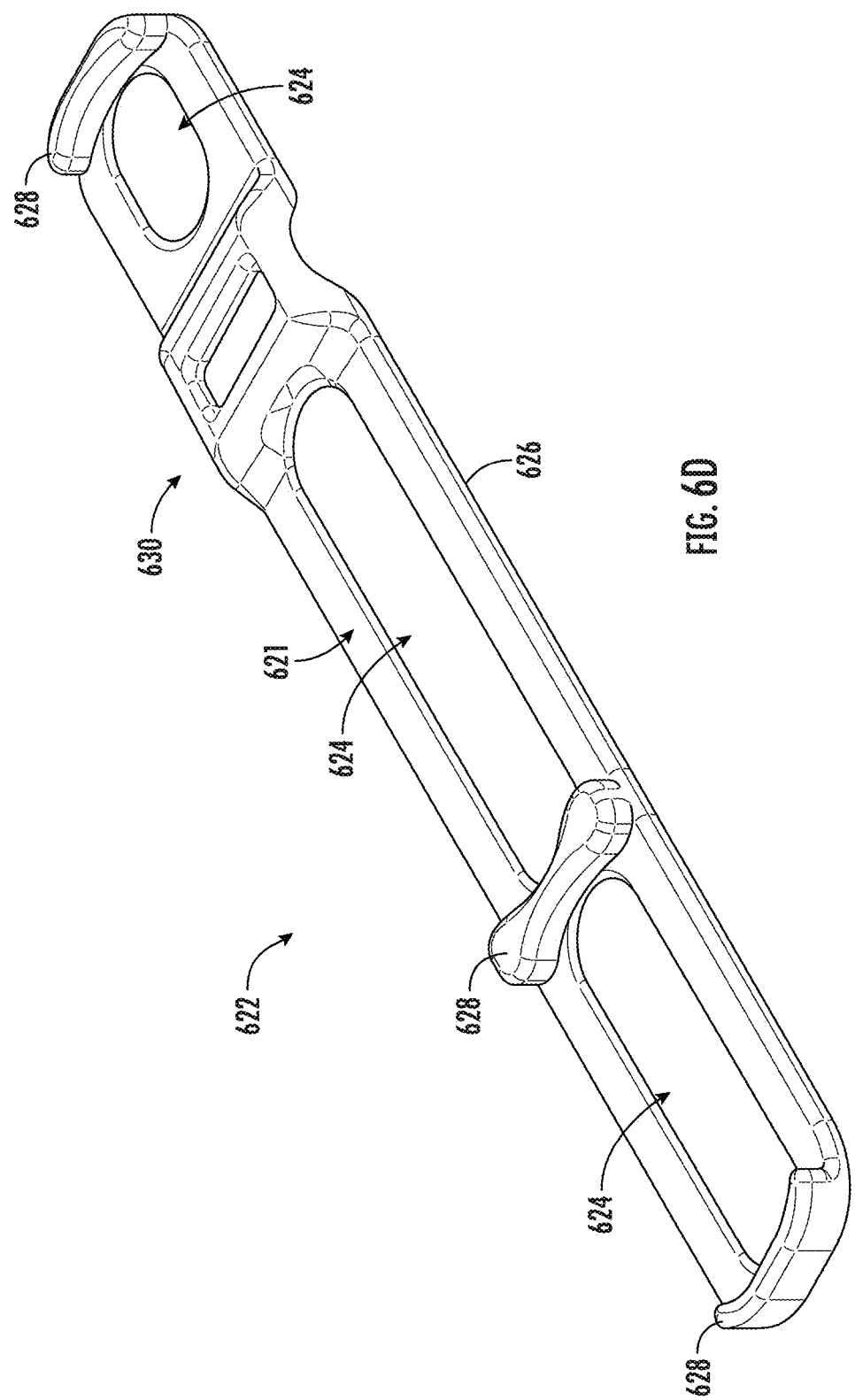

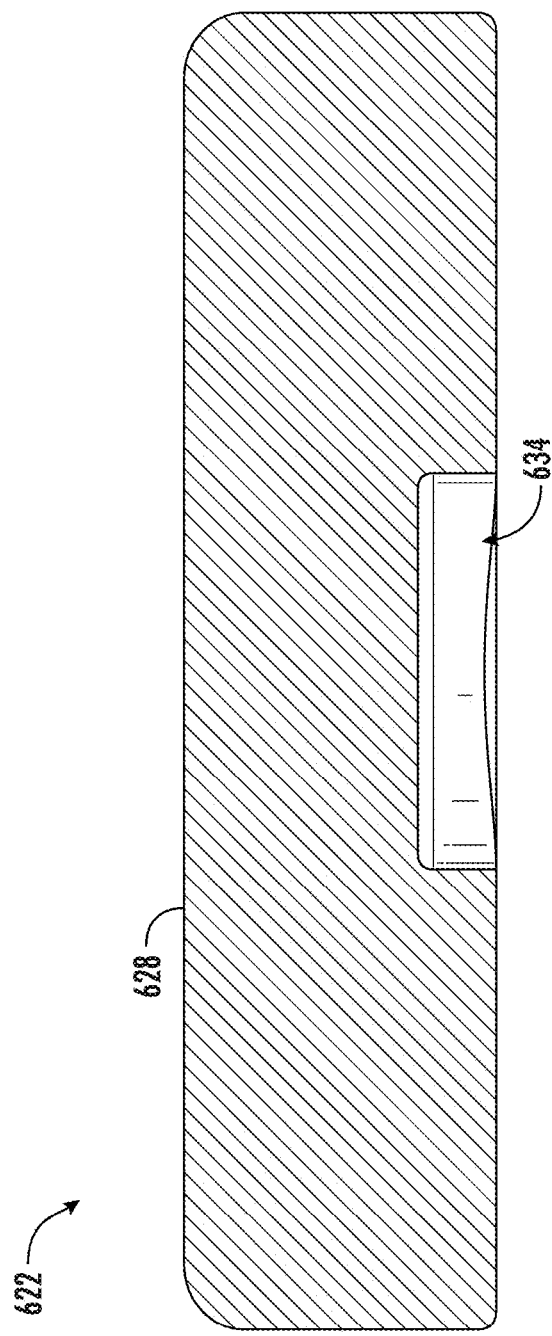

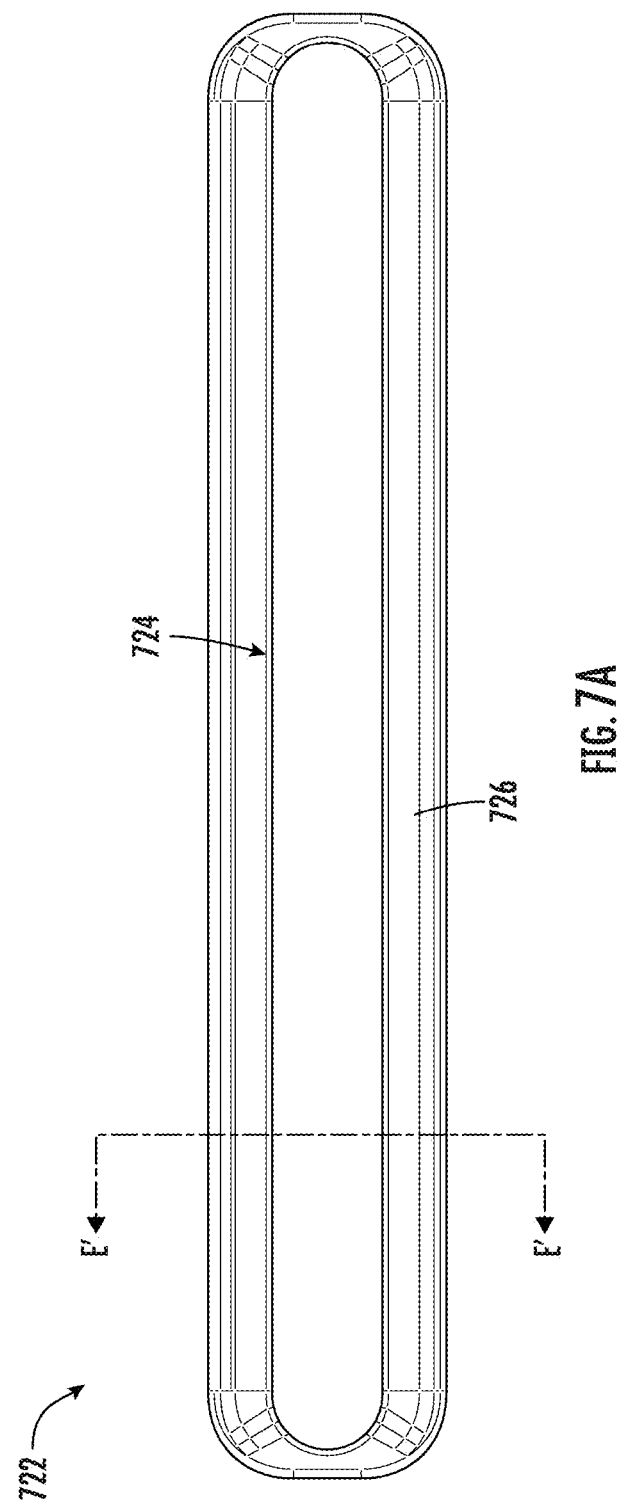

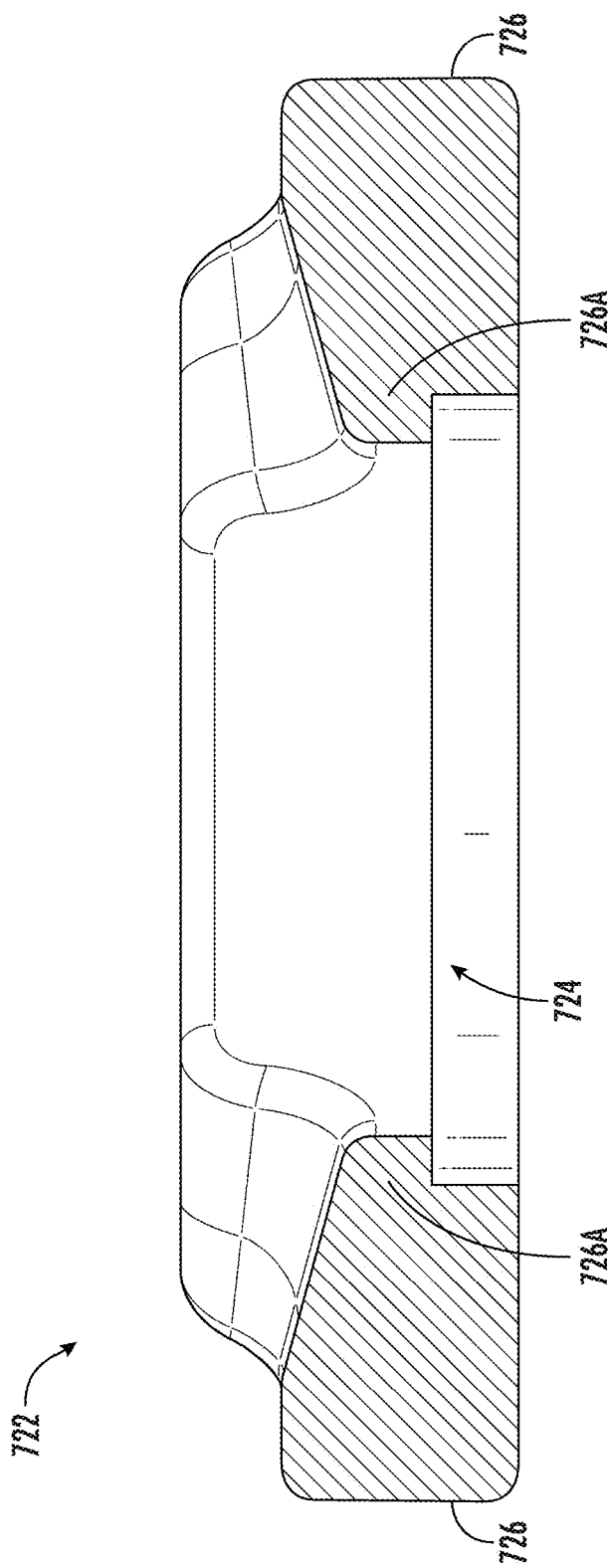

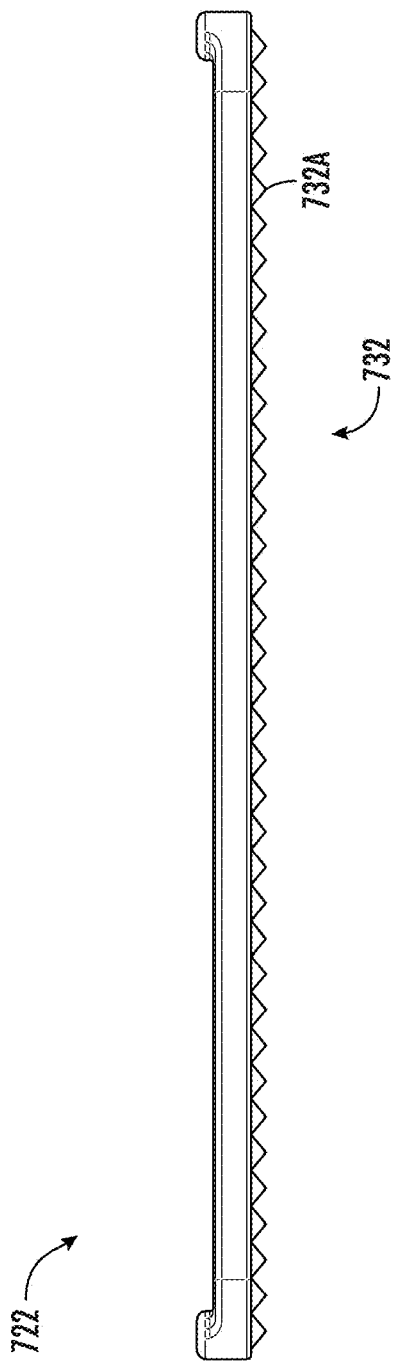

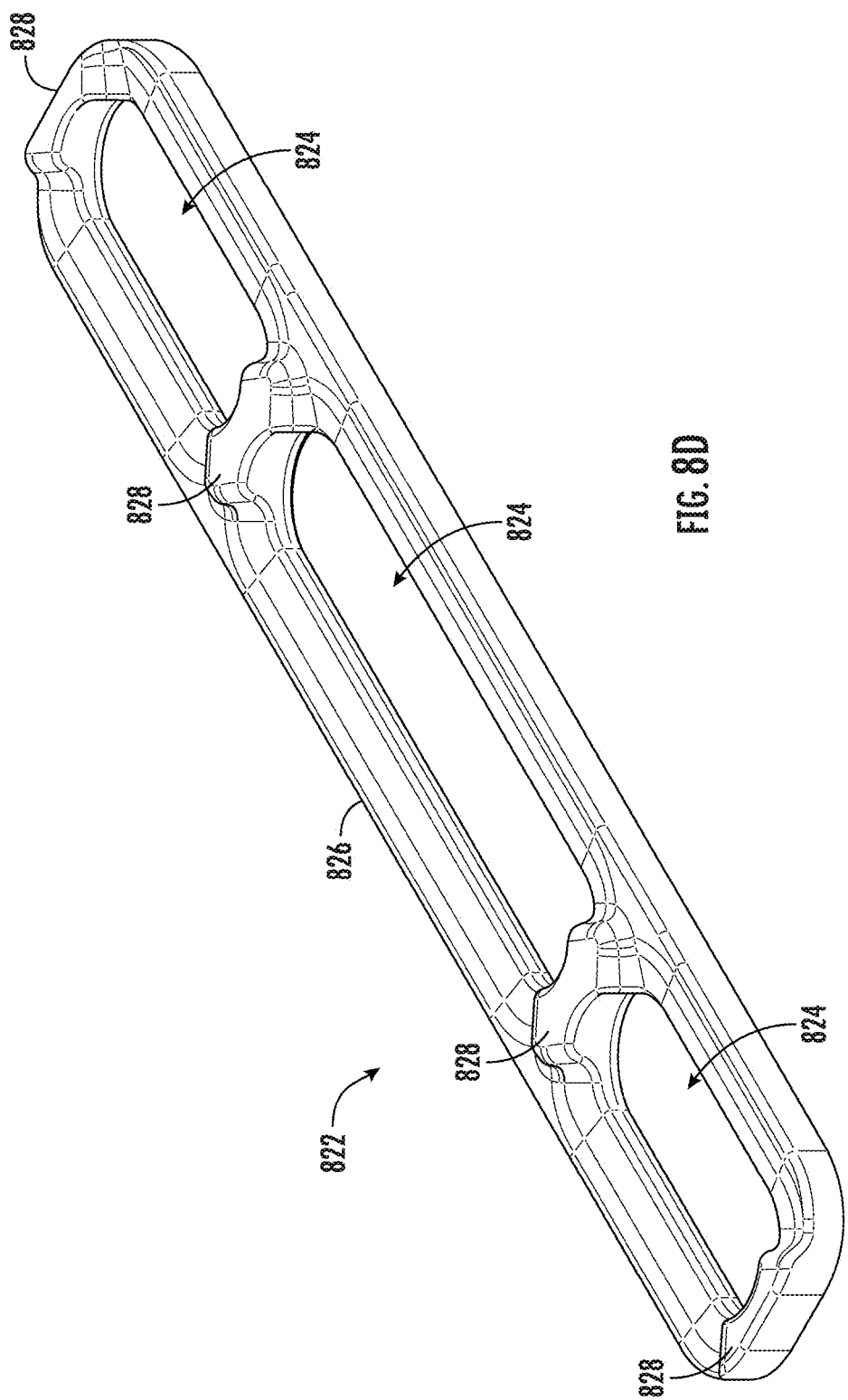

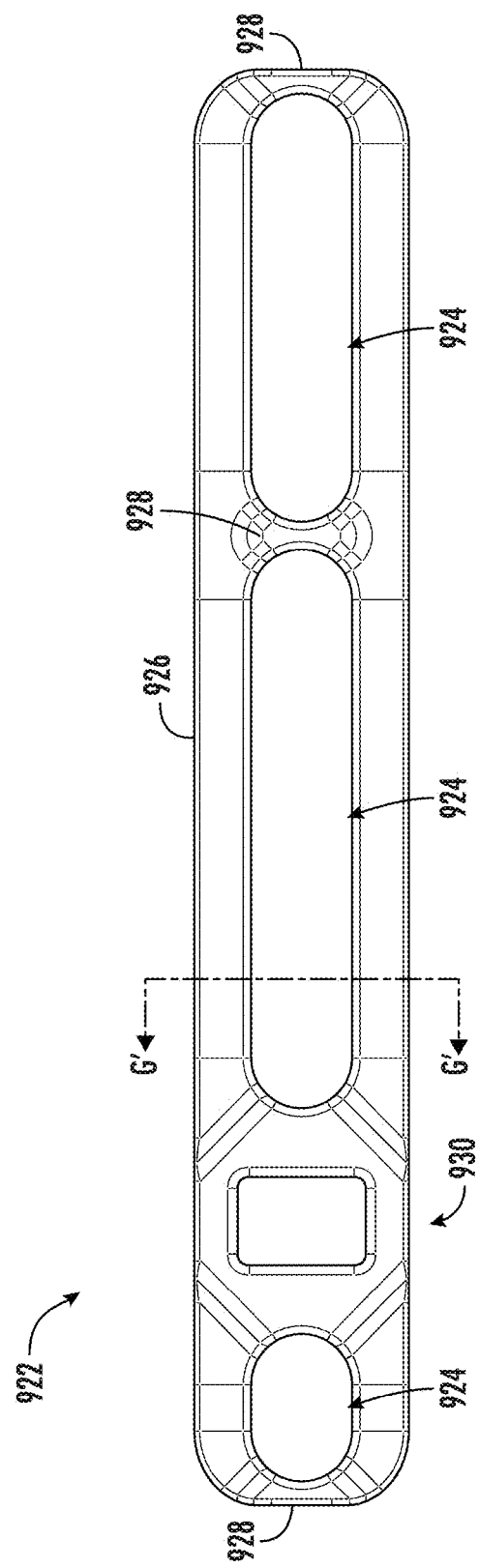

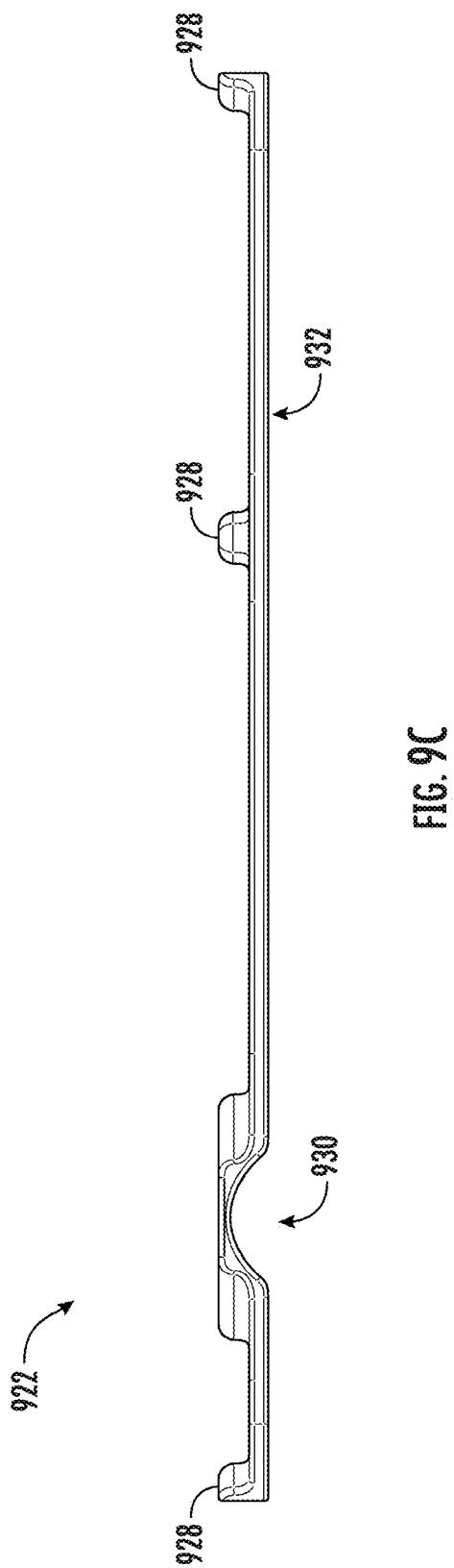

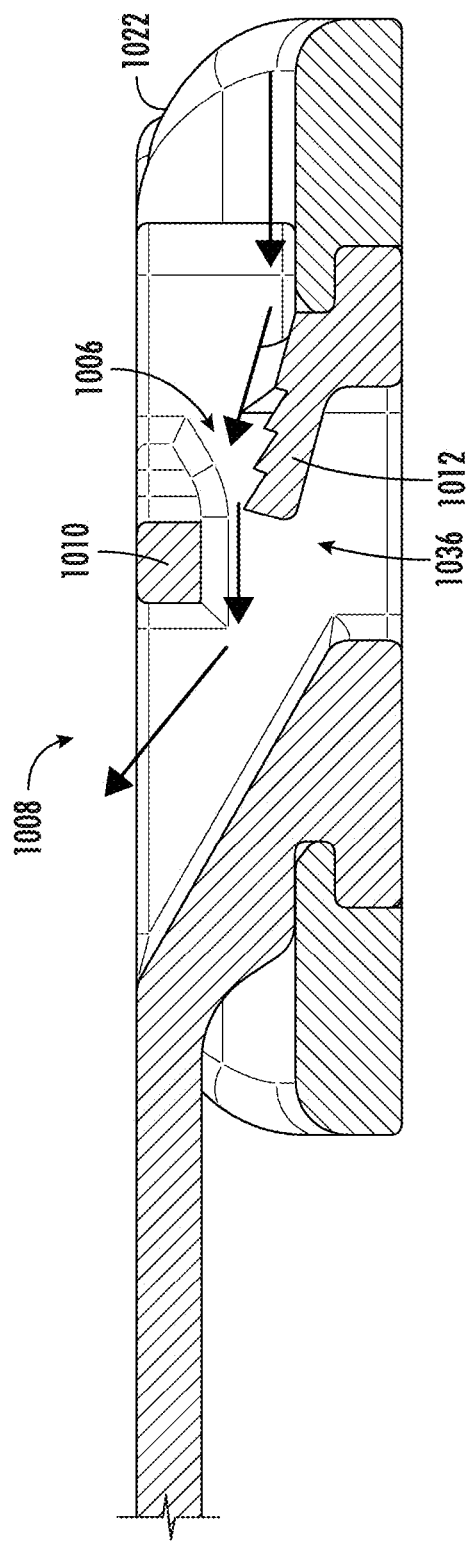

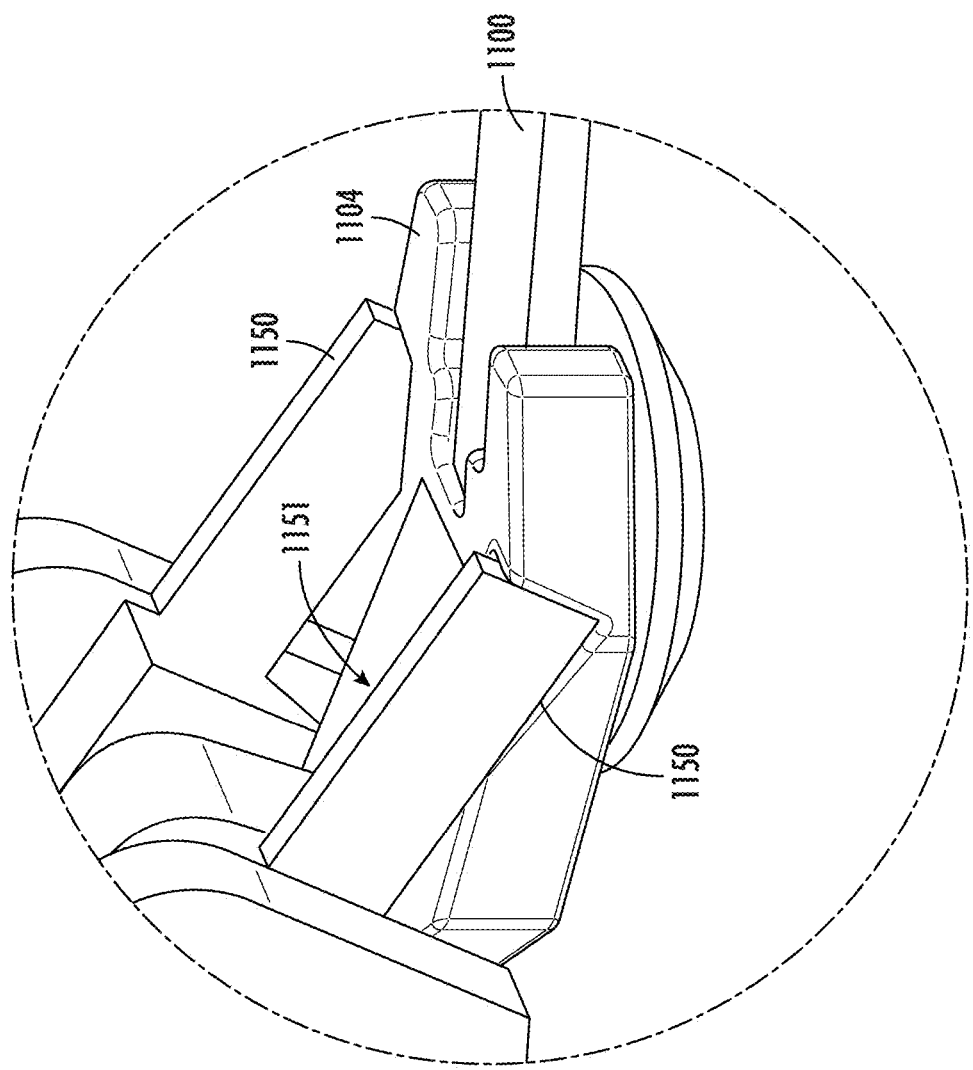

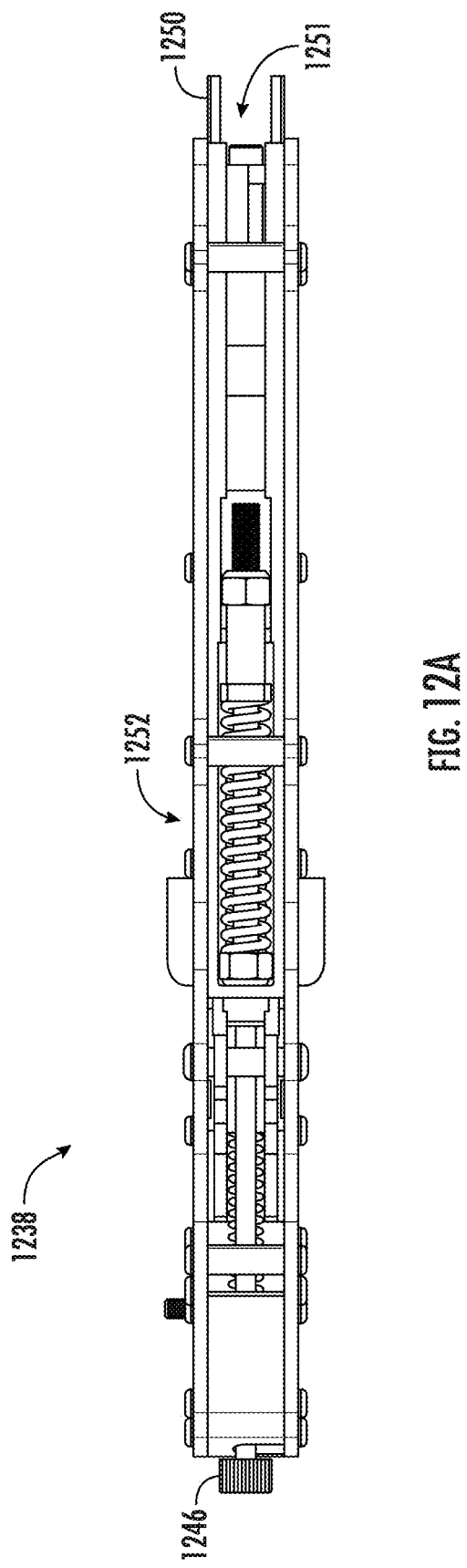

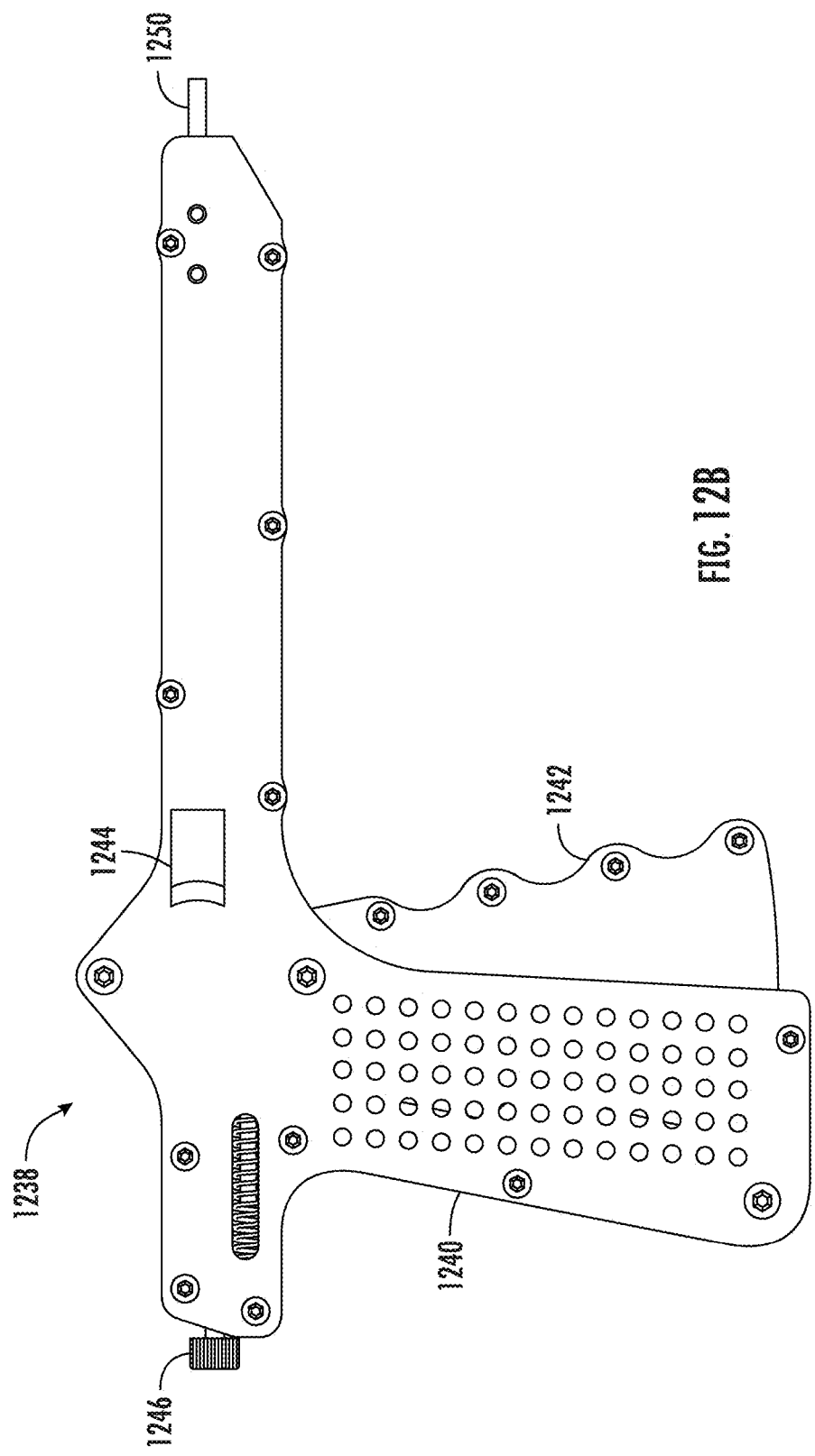

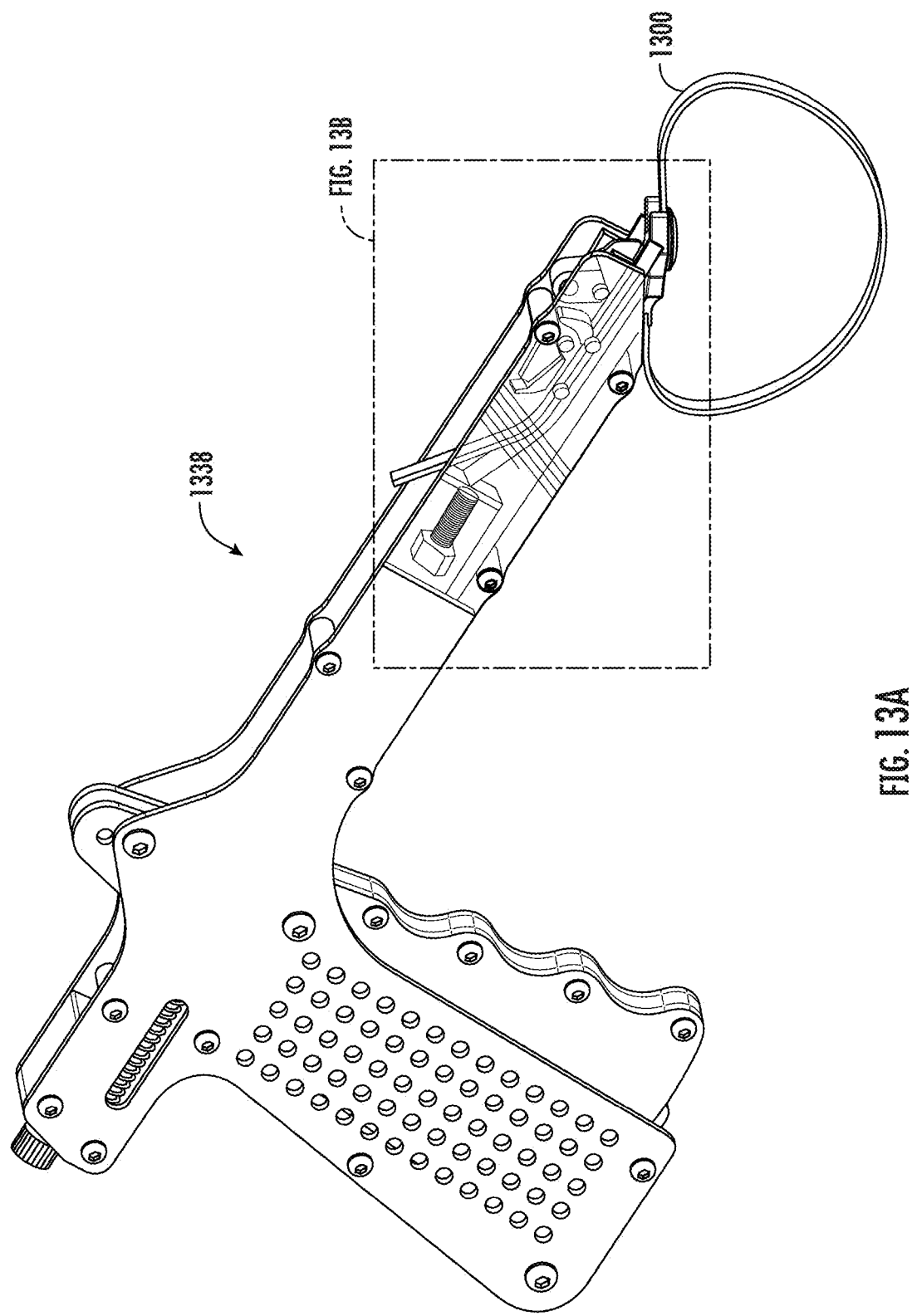

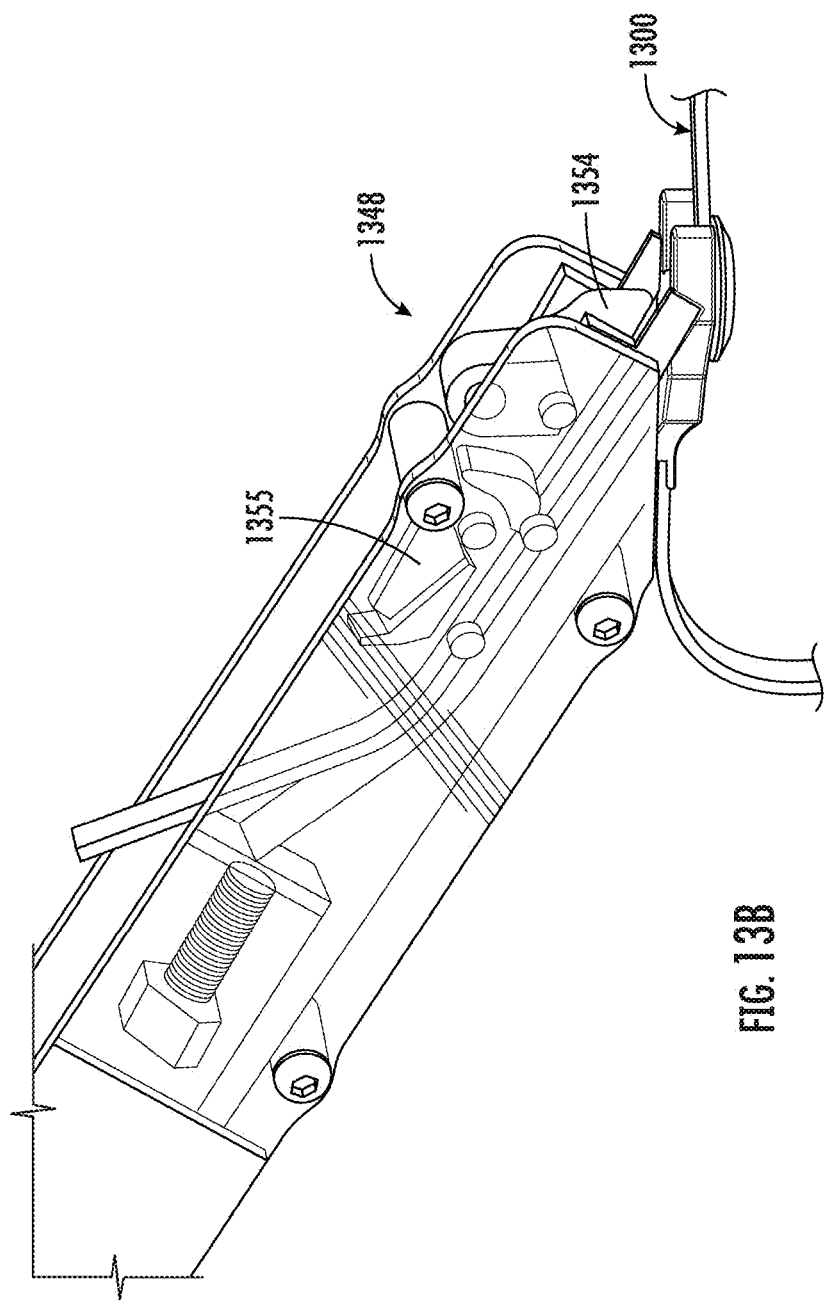

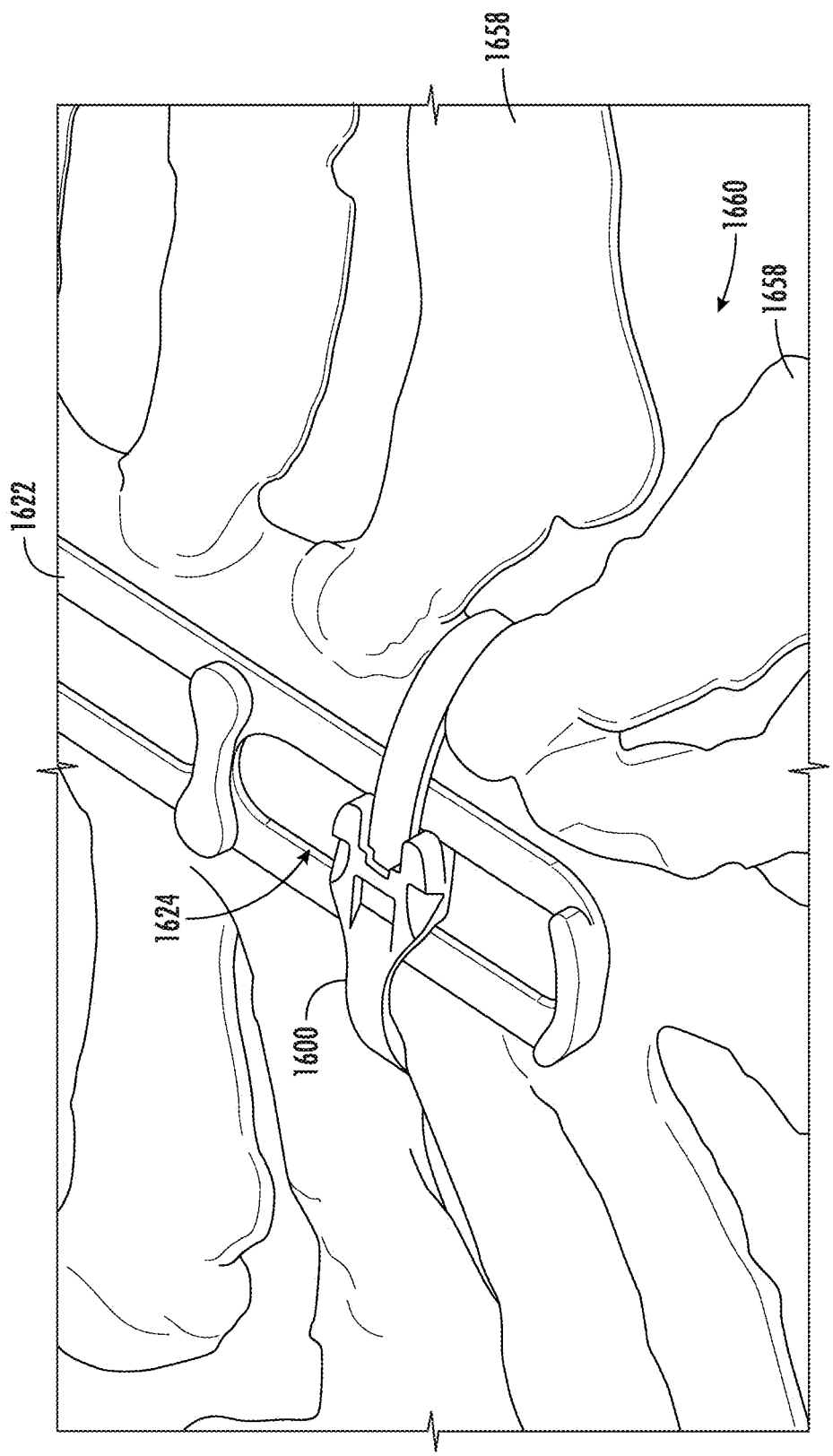

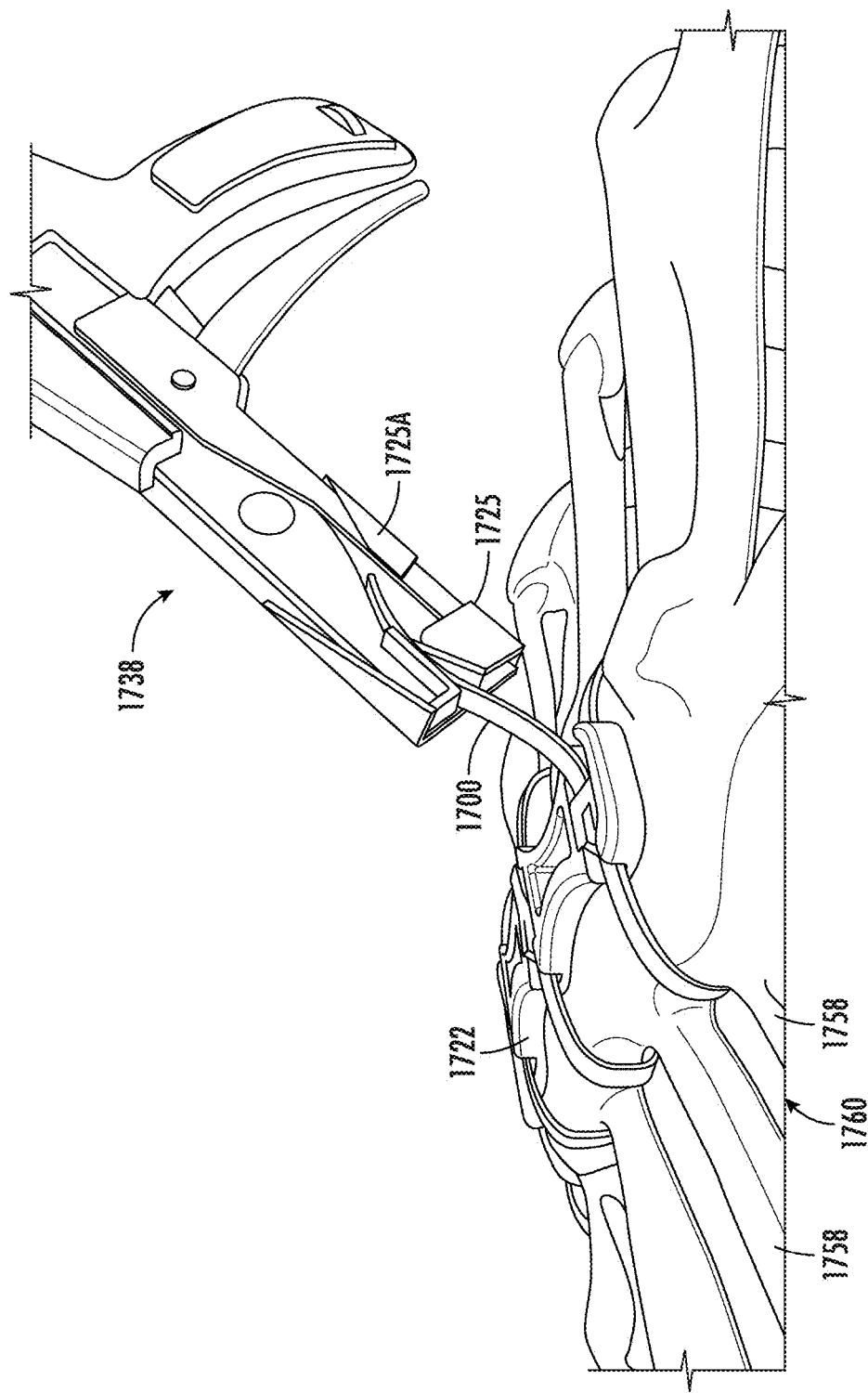

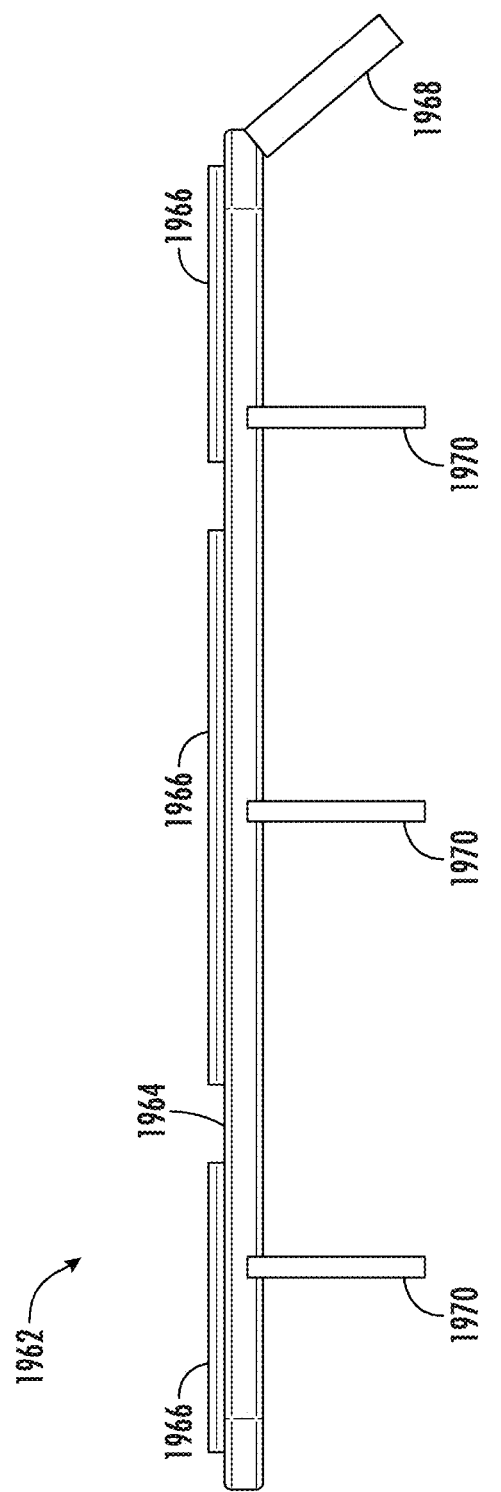

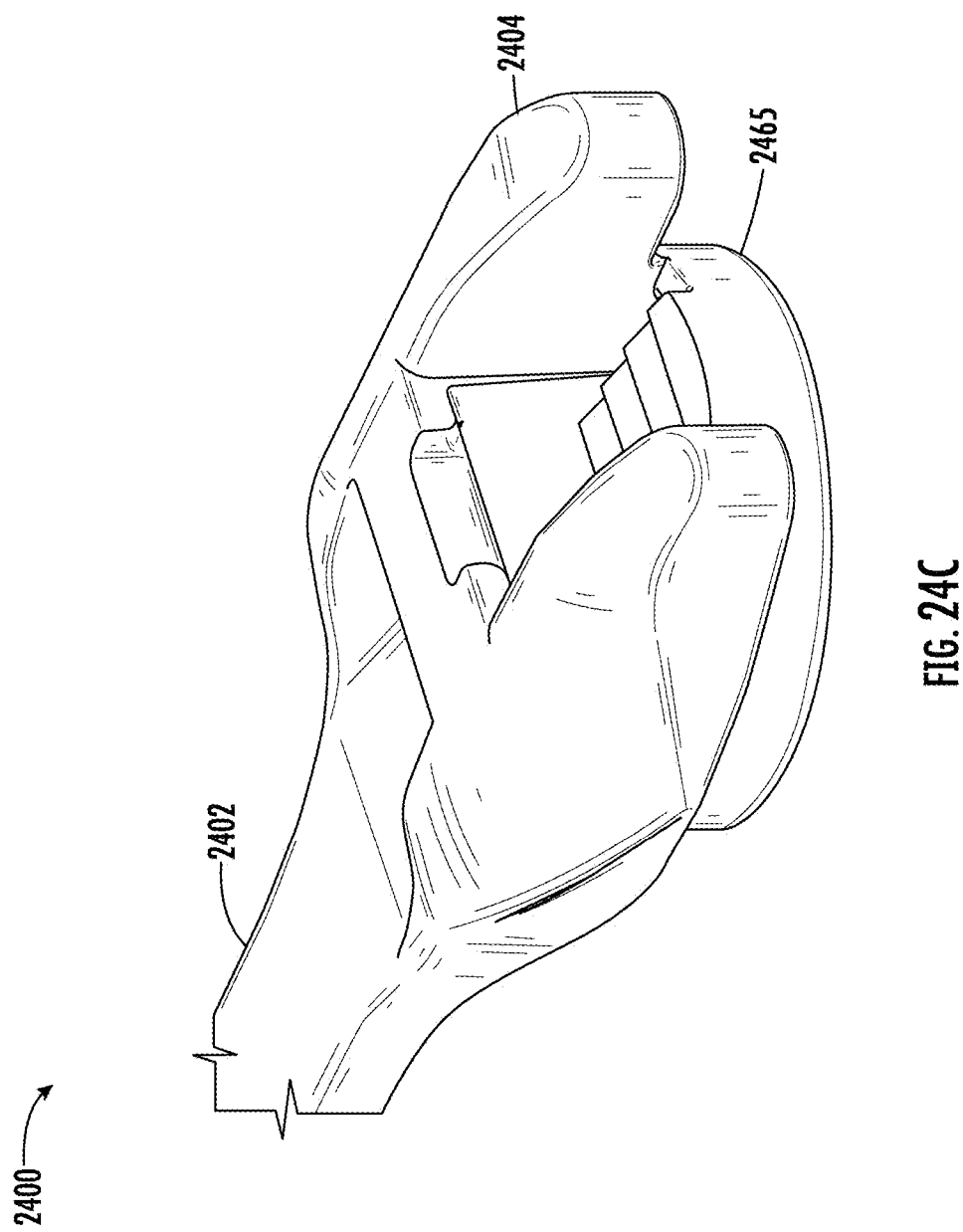

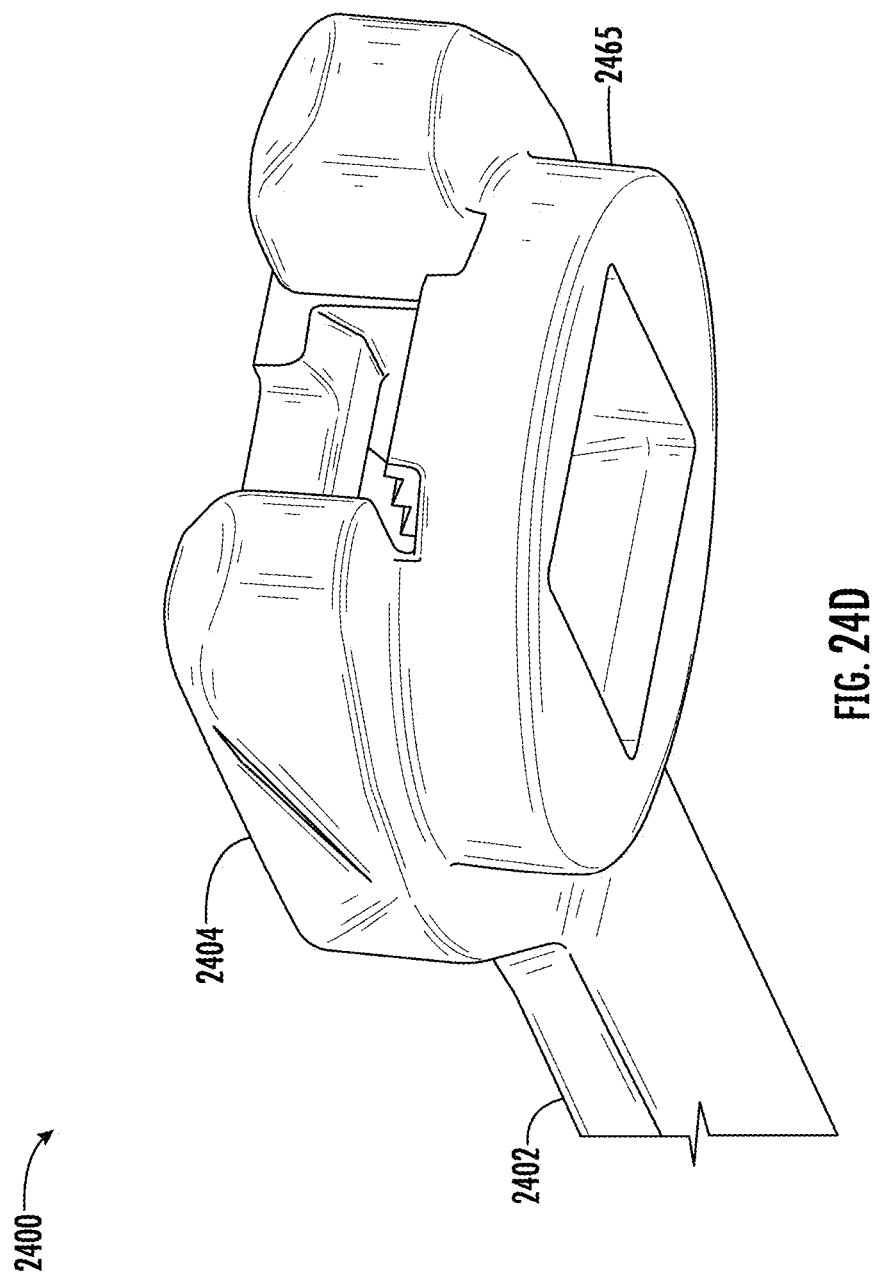

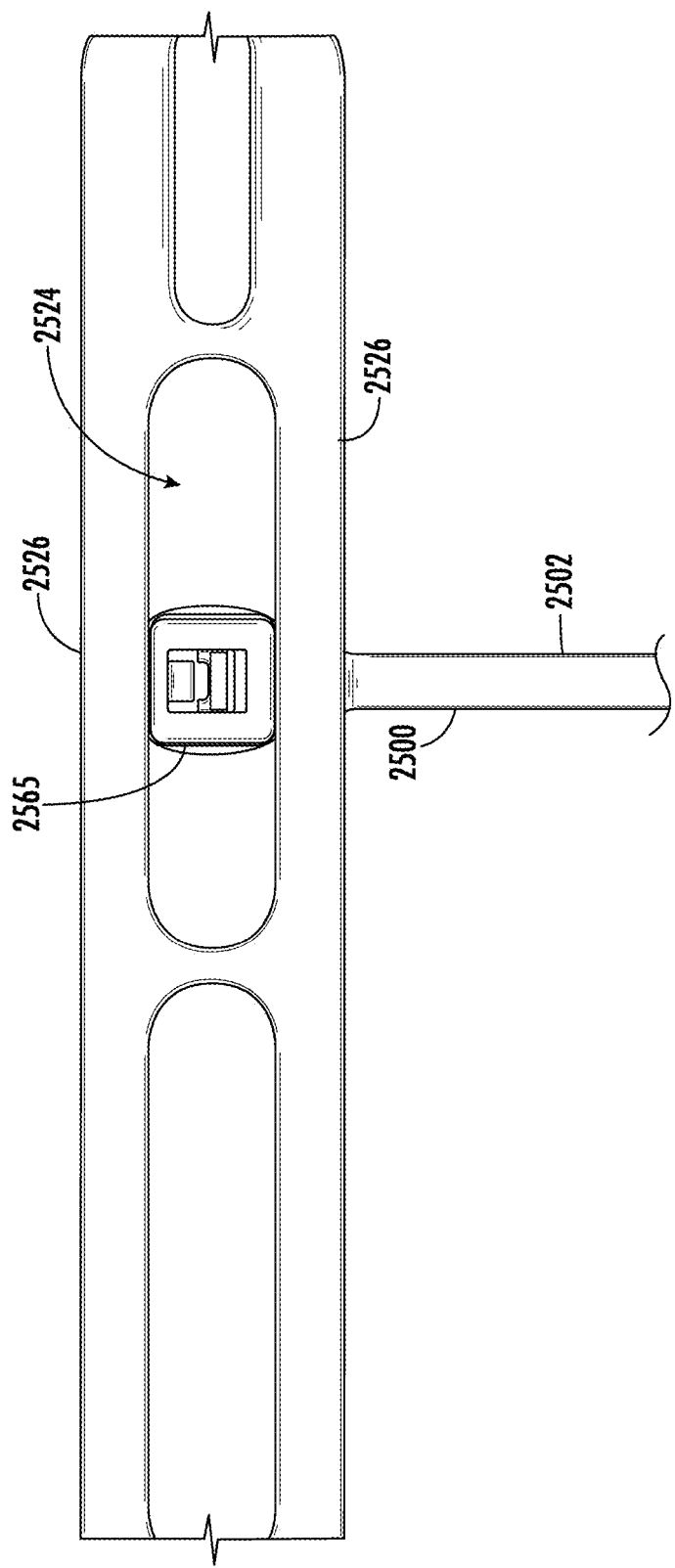

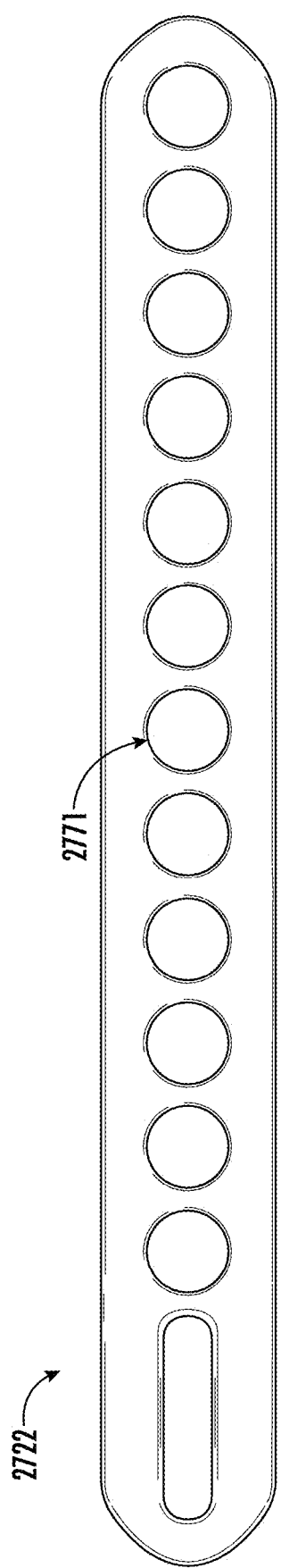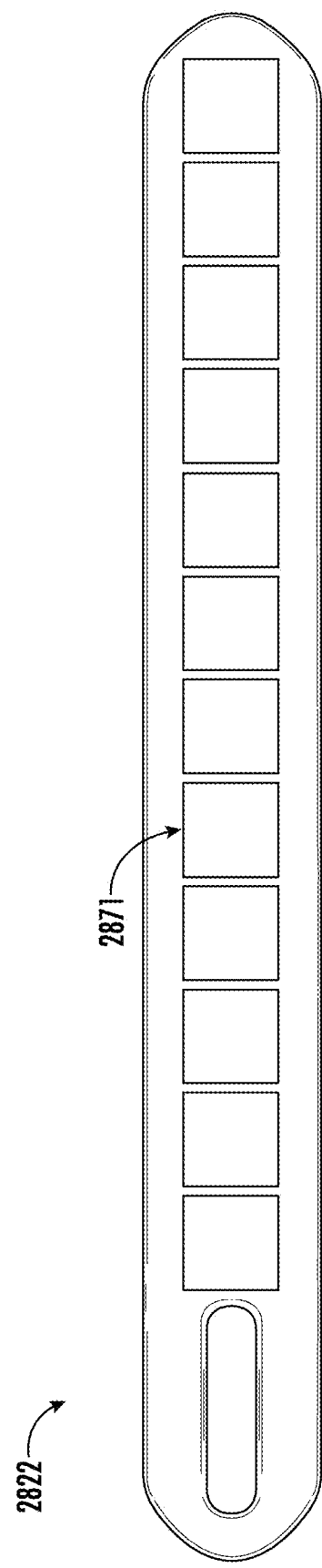

BONE REPAIR DEVICES AND METHODS

CROSS REFERENCE TO RELATED APPLICATIONS

This application claims the benefit of U.S. Provisional Patent Application No. 63/227,060, filed on Jul. 29, 2021, and entitled "Sternum Fixation Devices and Methods". The entire contents of the aforementioned application is hereby incorporated herein by reference for all purposes.

FIELD OF THE INVENTION

Embodiments of the present invention relate generally to methods and apparatuses for stabilizing a bone and for removal of excess fluid from a surgical site.

BACKGROUND OF THE INVENTION

In sternotomy surgeries, the patient's sternum is severed in half to create access to the inter-thoracic cavity to perform operative surgical procedures. Following such procedures, the two separated halves of the sternum must be repositioned adjacent to each other and affixed so that the two halves may be permitted to heal. Attempts have been made to constrain the separated halves together using wire threaded around the sternum and manually tensioned and twisted into place. However, wire can cause irritation to the sternum and other surrounding areas of the body, causing the patient additional pain and discomfort. Additionally, there are inherent inconsistencies from surgeon to surgeon as to the positioning of the wire, the tightness of the tensioning, the manner of twisting, etc.

Furthermore, after surgical procedures and/or a sternotomy, excess fluid (e.g. blood) may collect around a surgical site. If excess fluid is not removed, this excess fluid may become infectious, posing serious risk to the health of the patient and retarding or preventing recovery. Through ingenuity and effort, the inventors have developed various improvements to reclosure of the sternum following sternotomies and draining of related fluid.

BRIEF SUMMARY OF THE INVENTION

Various embodiments provided herein disclose methods and apparatuses for stabilizing a bone and/or for removal of excess fluid from a surgical site. A plate assembly is contemplated having a fixation plate that may be positioned against a bone, such as the sternum, to assist in the stabilization of the bone. Bands may be attached to the fixation plate and wrapped around the fixation plate and the bone so that the bands form a loop. The loops formed by the bands may be tensioned and eventually cut by a tensioning gun. The fixation plate may have windows and other openings therein to generally create an open architecture within the fixation plate, and this open architecture may be beneficial to permit the free passage of blood and biological materials to effect healing at a bone site.

A surgical drain assembly may be provided in some embodiments as well. The surgical drain assembly may comprise a drain body that may be provided between the fixation plate and a bone (e.g. the sternum). The drain body may be snap fitted or otherwise attached to the fixation plate. Furthermore, the drain body may have extension tubes attached to the drain body, and the extension tubes may be wrapped behind the sternum or behind another bone to collect any excess fluid, such as blood, at that location. A drainage tube and/or an inlet tube may also be provided. The drainage tube may permit fluid collected from an internal cavity of the drain body to be removed from the patient's body, and the inlet tube may permit fluids (e.g. medicines, etc.) to be introduced to a surgical site via the surgical drain assembly. The drain body may be positioned above the sternum and the fixation plate to permit easy installation and removal of the drain body.

The tensioning gun may permit a user to set a tension limit, with this tension limit being the maximum tension that may be applied to a band using the tensioning gun. Once the tension limit has been reached, the tensioning gun may cease applying tension. In some embodiments, upon reaching the tension limit, a cutting blade may be activated to cut the band. Alternatively, the tensioning gun may continue to apply tension to the band at or around the tension limit, and the tensioning gun may cause a cutting blade to be actuated to cut the band. As another alternative, the tensioning gun may apply tension up to the tension limit, and the user may deploy another cutting tool to cut the band upon the tension limit being reached.

While bands may be manually installed, tensioned, and then cut, it may be disadvantageous to perform these tasks manually for several reasons. First, manual performance of these tasks can lead to human error. The bands may not be tightened to an appropriate tension and this may cause the patient to heal improperly and/or to experience pain (i.e. too loose may allow too much movement of the sternum; too tight may cause pain for the patient or too much tension on the sternum). Second, manual performance of the tasks will be less user-friendly. Where the fixation plate is being installed at a severed sternum, one or more installers would need to maintain the two severed sternum halves in an appropriate position, they would need to maintain the fixation plate at the appropriate position, and they would need to install bands to retain the fixation plate in the appropriate position. This may be difficult to do at the same time, increasing frustration for the installers and leading to an increased risk of error during installation. Third, manual performance of the tasks may very time consuming for installer(s).

Tensioning guns are contemplated that may be used to apply tension to bands until a desired tension level is reached. Once the desired tension level is reached, the tensioning gun may cut the band. The tensioning gun may reduce human error by maintaining a consistent amount of tension in each band. Manual tensioning places undue reliance on user judgment based on prior experience, visualization or tactile feel, and approximations or guesswork from the installer may lead to errors. The tensioning gun may be easier for installers to operate, thereby eliminating any approximations or guesswork from the installer as to whether the tension level is appropriate. By cutting the bands automatically after the desired tension is obtained, this may alleviate the need for the installer to perform this task separately. The tensioning gun may also tighten the bands more quickly than manual tightening of bands.

In an example embodiment, a plate assembly for stabilizing a bone is provided. The plate assembly includes a fixation plate having rails that form a window. The plate assembly also includes a band having a tail and a head defining an internal cavity being configured to receive a portion of the tail. The fixation plate is configured to be positioned proximate to a bone, and the head is configured to be at least partially received at the fixation plate between the rails within the window. The band is configured to be wrapped around the fixation plate and the bone. Furthermore, the internal cavity of the head is configured to receive an end of the tail to form a loop, and the band is configured to receive a tension force to tighten the loop formed by the band.

In some embodiments, the head may include a bottom portion, and this bottom portion may not include radially extending tabs. Additionally, in some embodiments, the bottom portion may be configured to be passively received within a window of the fixation plate.

In some embodiments, the head may be configured to be selectively removable from the window when no loop has been formed by the band, and the band may be configured to urge the head towards the fixation plate upon tightening of the loop formed by the band. Furthermore, the window may possess an elongate shape that is configured to permit the head to slide along the window in some embodiments. In some embodiments, translatory movement of the band may be at least partially restricted upon tightening of the loop formed by the band.

Additionally, in some embodiments, a shape of the bottom portion and a shape of the window may both configured to permit the band to rotate relative to the window when no tension is being applied to the band. Furthermore, in some embodiments, the bottom portion has a circular shape.

In some embodiments, a shape of the bottom portion and a shape of the window may both be configured to prevent the band from rotating relative to the window when no tension is being applied to the band. Furthermore, in some embodiments, the bottom portion may have a square shape, a triangular shape, a rectangular shape, a pentagonal shape, a hexagonal shape, an octagonal shape, or a star shape. In some embodiments, the bottom portion may simply have a square shape.

In some embodiments, a shape of the bottom portion may match the shape of the window. Further, receipt of the bottom portion in the window may be configured to prevent translatory movement of the bottom portion relative to the window. Additionally, in some embodiments, receipt of the bottom portion in the window may be configured to prevent rotational movement of the bottom portion relative to the window.

In some embodiments, the head may include a bottom lock having radially extending tabs. The rails may have protruding portions that extend into the window, and a portion of the head may be configured to be received within the window. The bottom lock may be configured to engage the protruding portions to restrict the head from being removed from the window.

In some embodiments, the bottom lock may possess a cam shape with reduced portions and enlarged portions. Edges of the enlarged portions may extend farther away from a center of the bottom lock than edges of the reduced portions. Additionally, in some embodiments, the band may be configured to rotate between an open position and a closed position, and the bottom lock may be oriented relative to the fixation plate such that the head may be removed from the fixation plate when the band is in an open position. The bottom lock may be oriented relative to the fixation plate such that the head may not be removed from the fixation plate when the band is in a closed position.

In some embodiments, the fixation plate may include one or more holes. The hole(s) may be configured to receive one or more additional fasteners. Further, in some embodiments, the additional fastener(s) may include at least one of a screw, a wire, and a suture.

In some embodiments, a tensioning tool may be used to apply a tension force to the band(s). The tensioning tool may have a tension limit that is the maximum tension that can be applied to a given band. The tensioning tool may be configured to apply tension to the band(s) until the tension limit has been reached.

BRIEF DESCRIPTION OF THE DRAWINGS

Figure 1A:
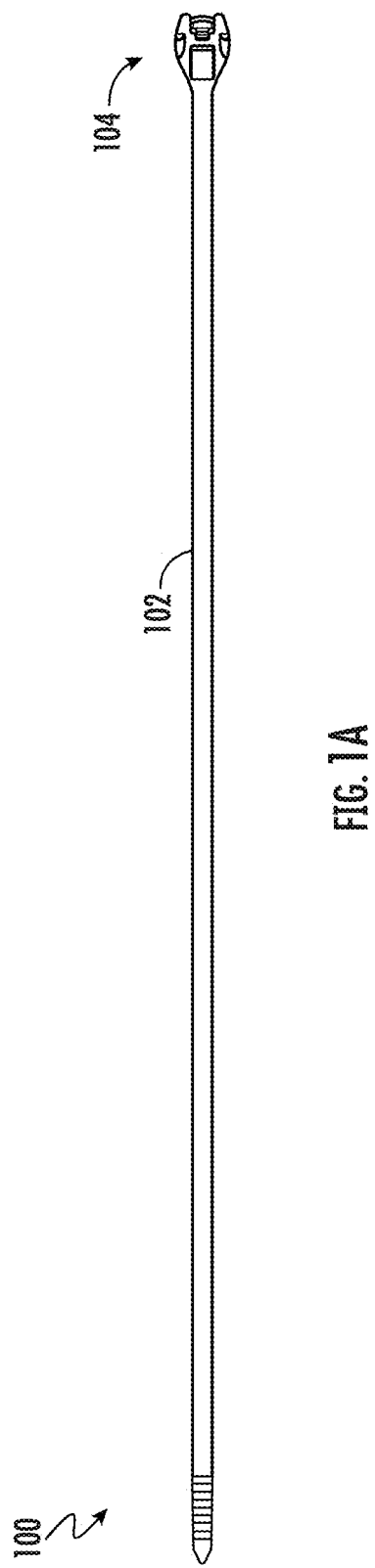
Figure 1B:
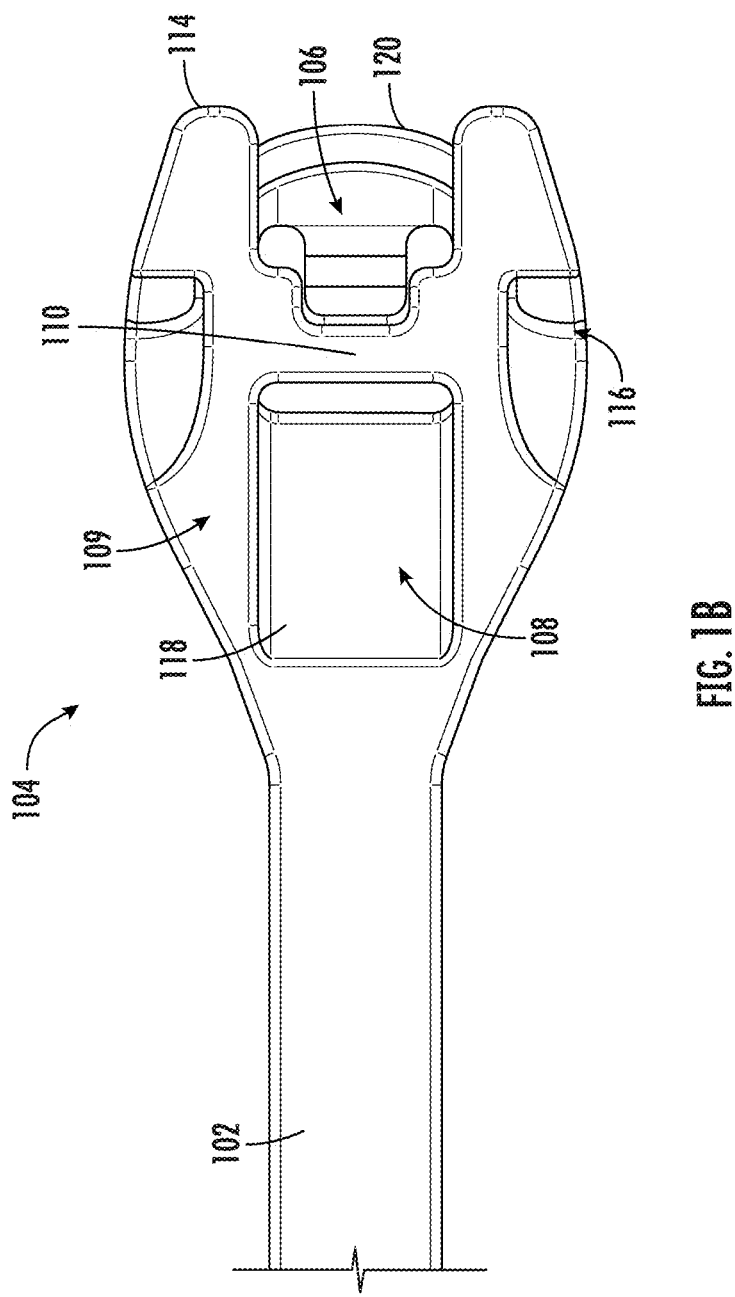
Figure 1C:
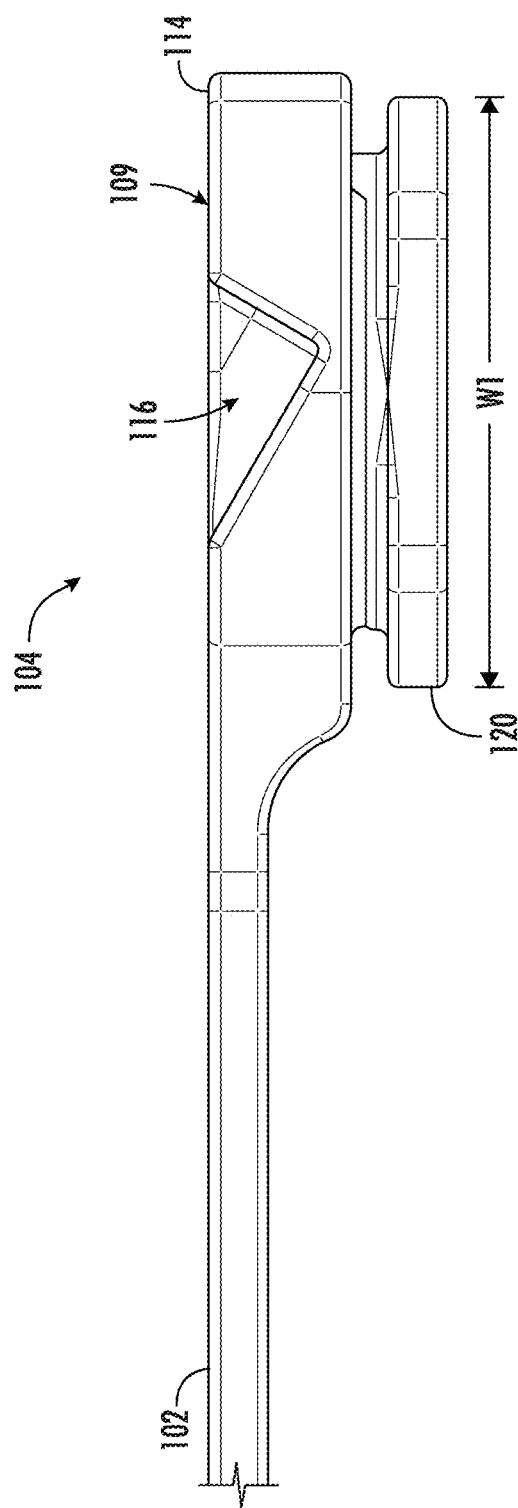
Figure 1D:
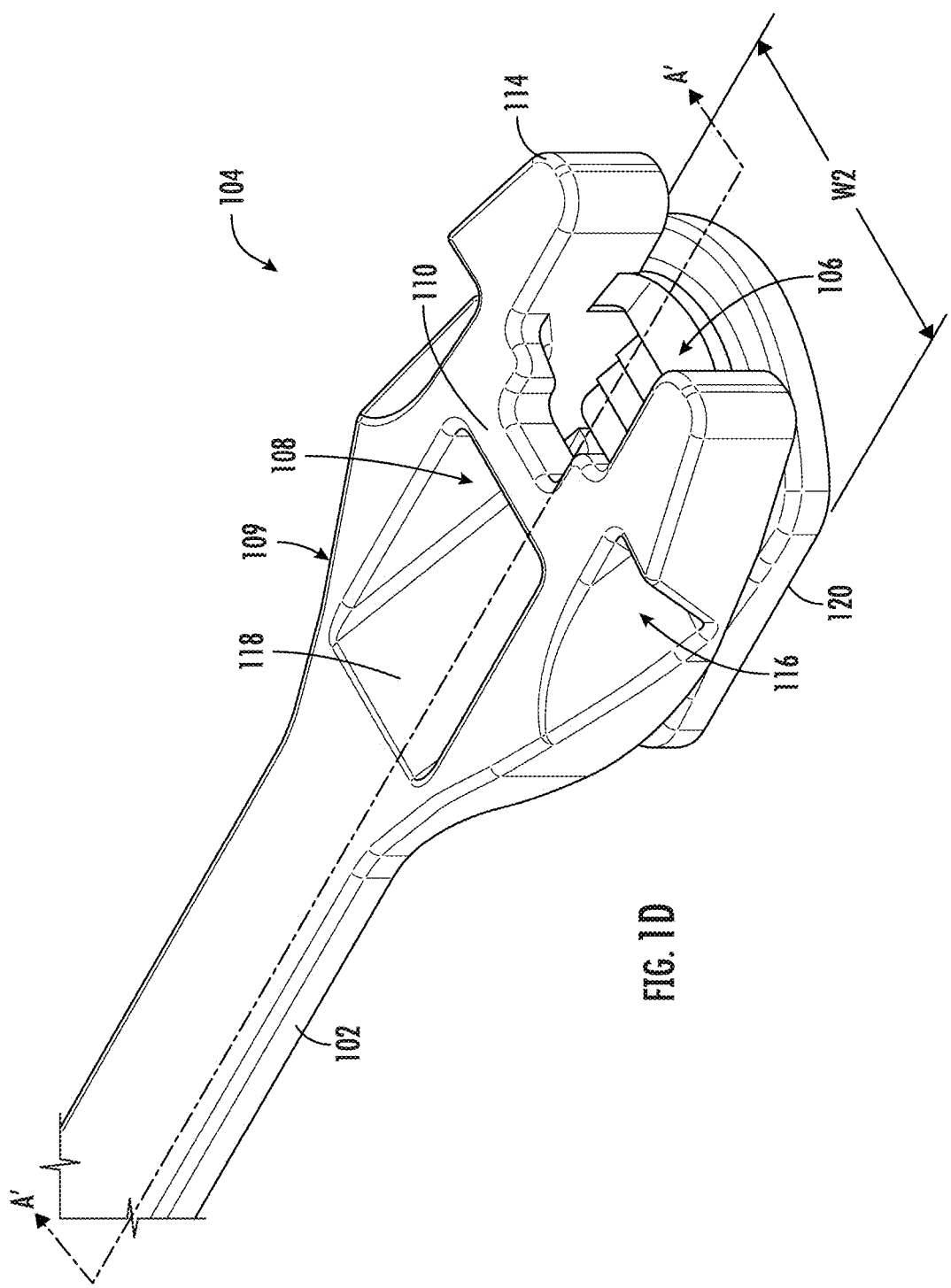
Figure 1E:
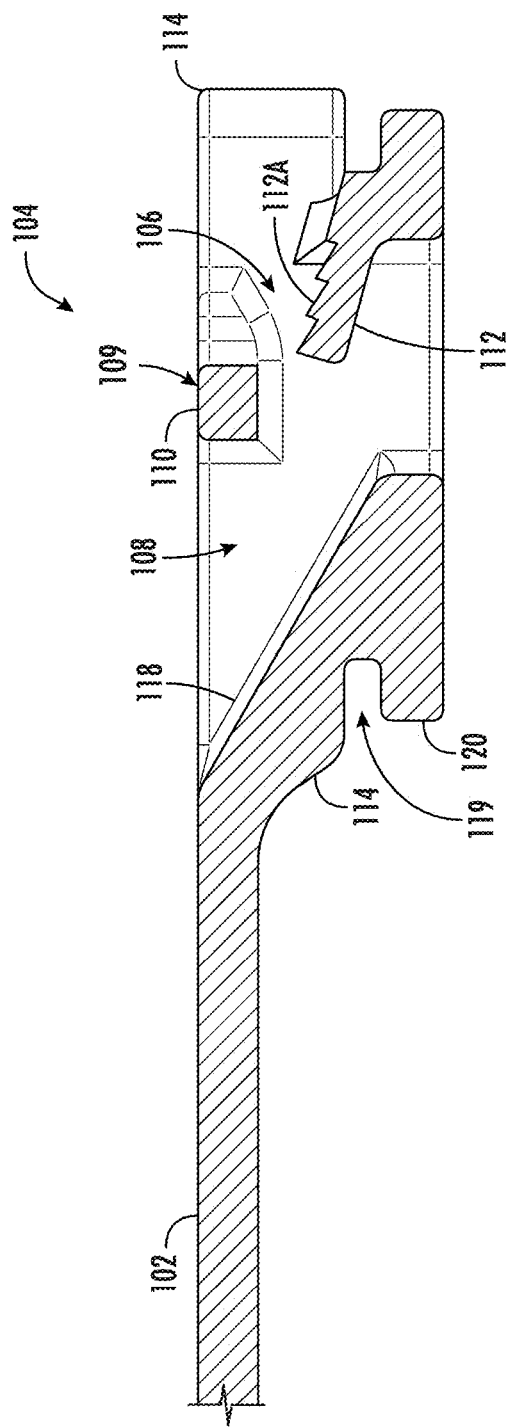
Figure 2C:
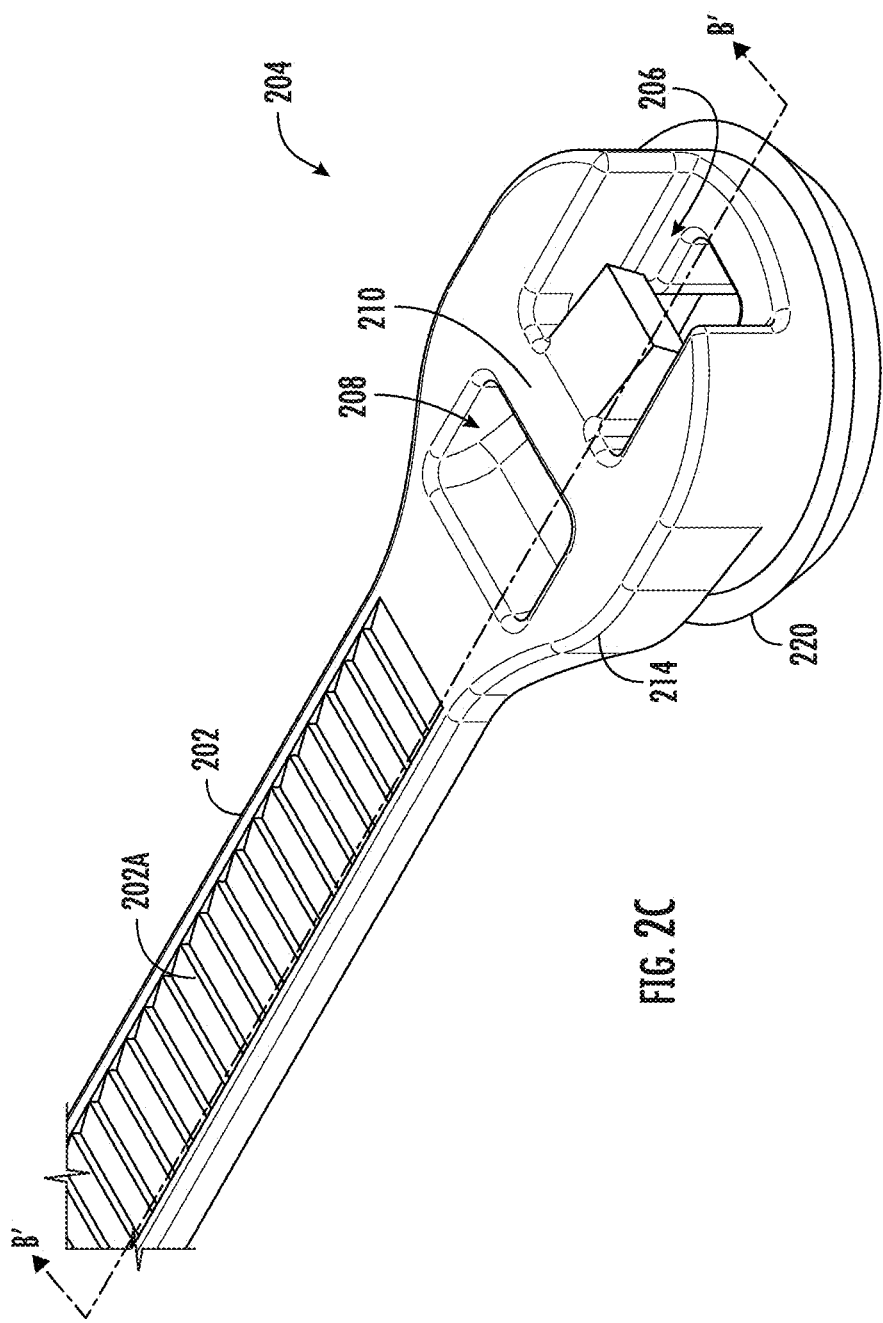
Figure 2D:
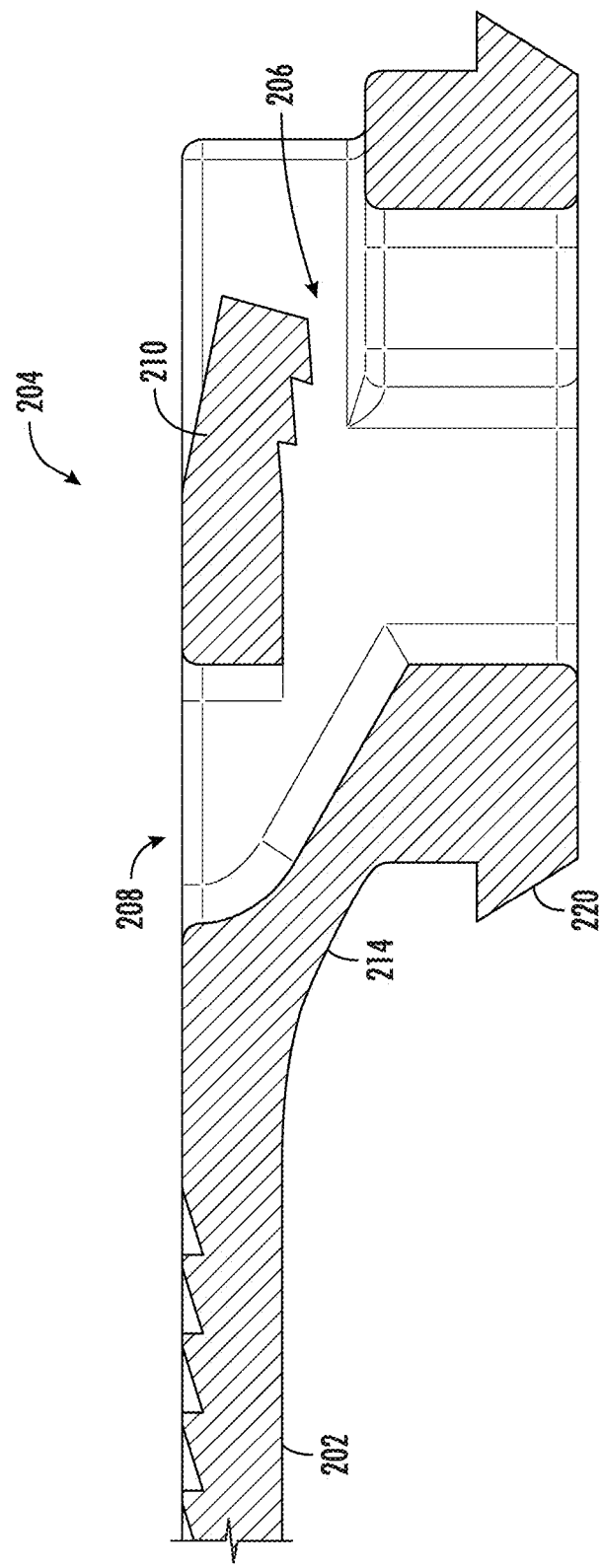
Figure 3:
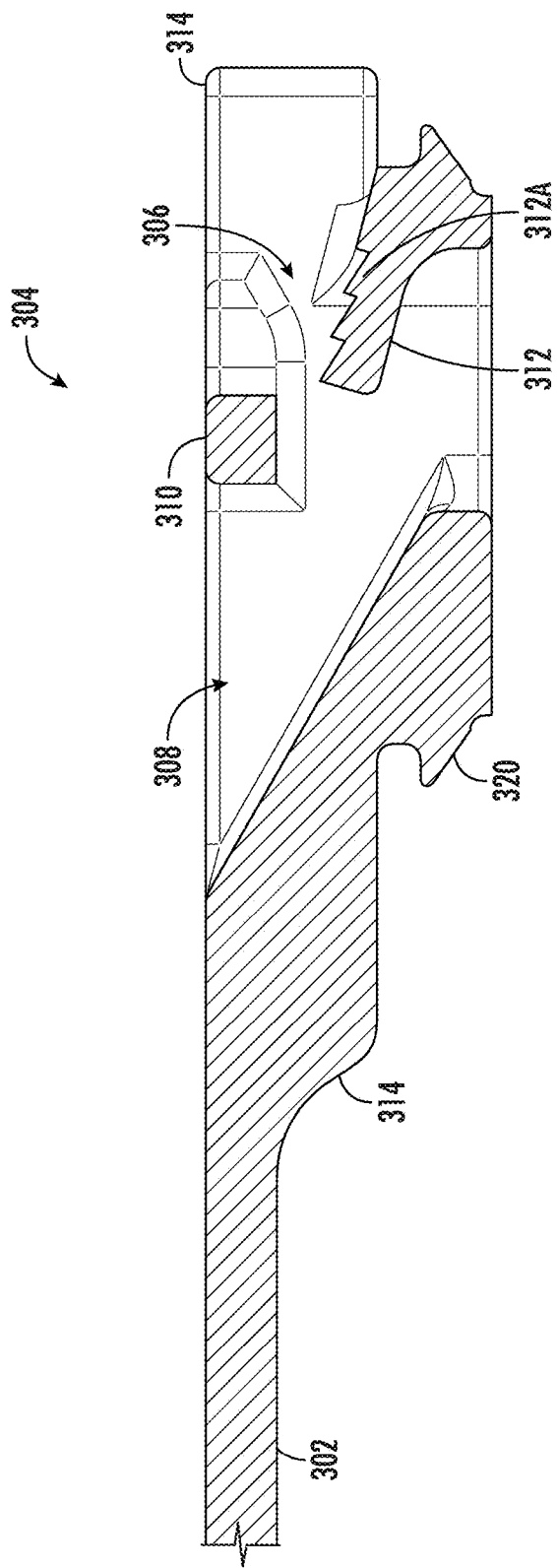
Figure 4C:
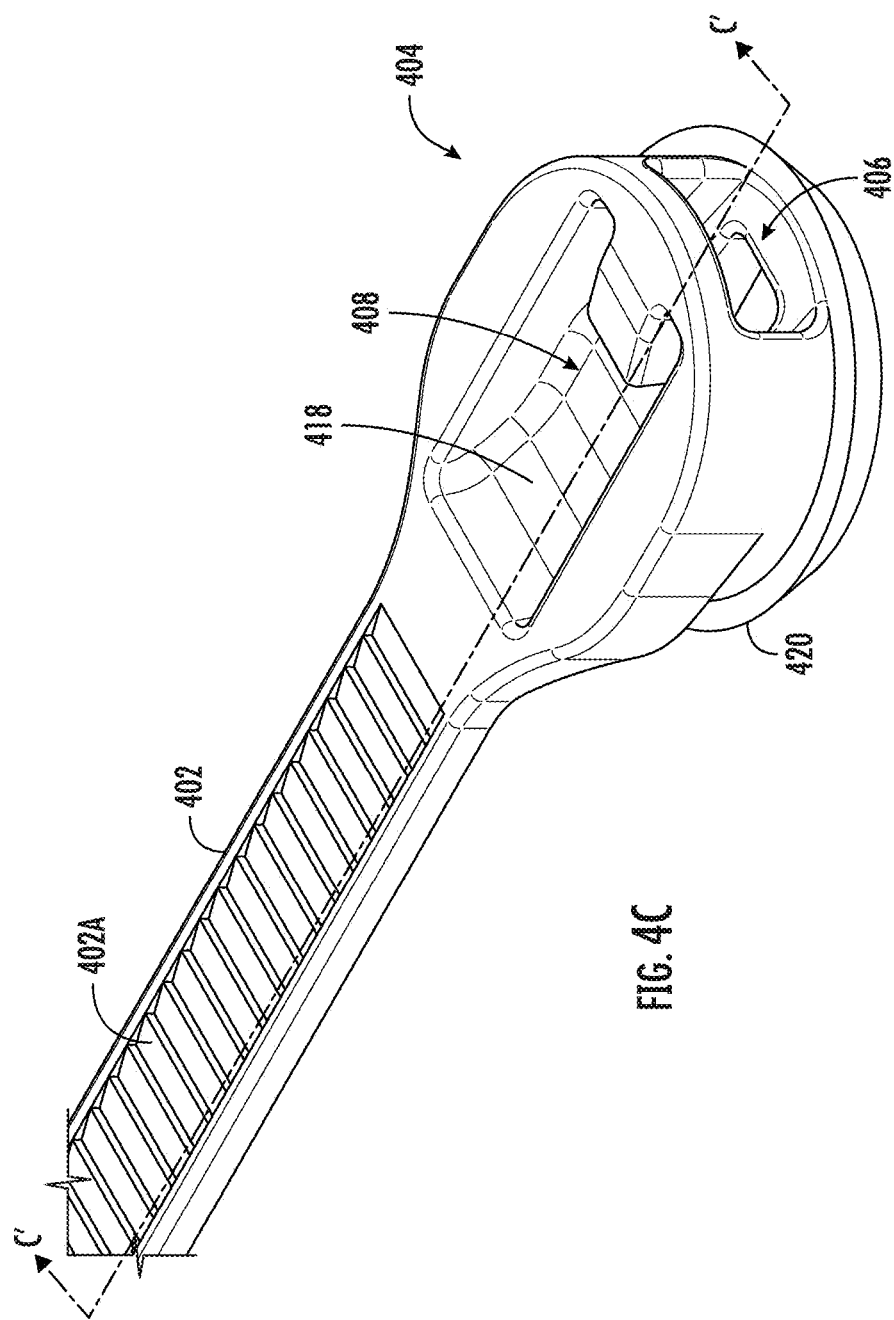
Figure 4D:
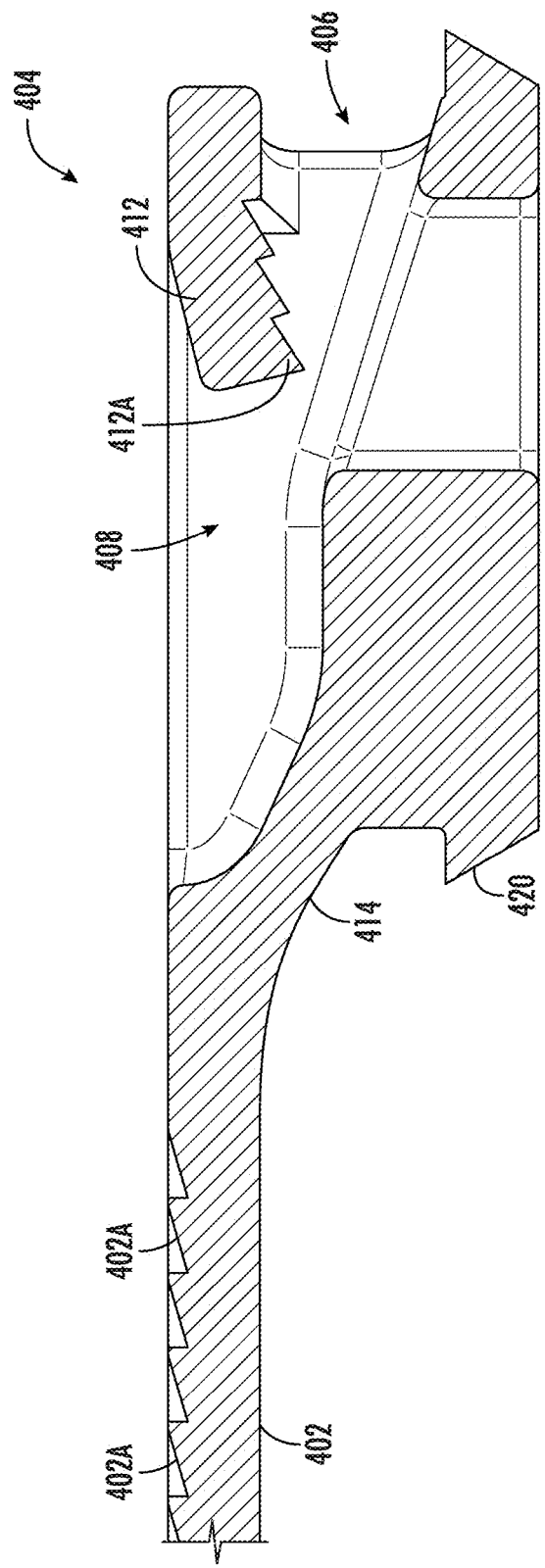
Figure 6A:
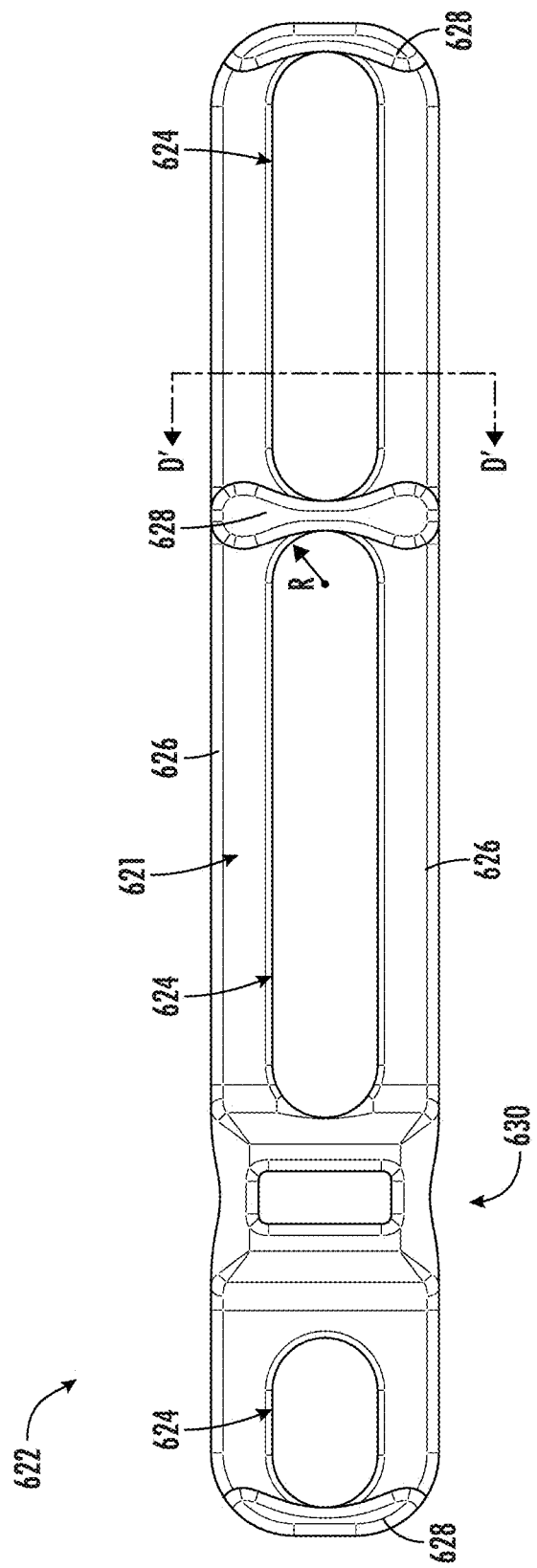
Figure 7C:
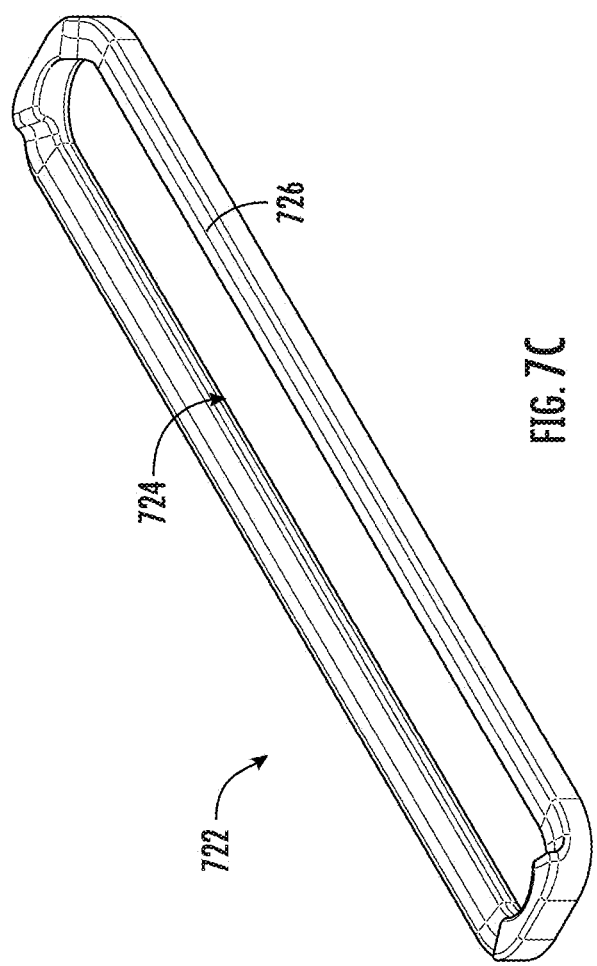
Figure 7D:
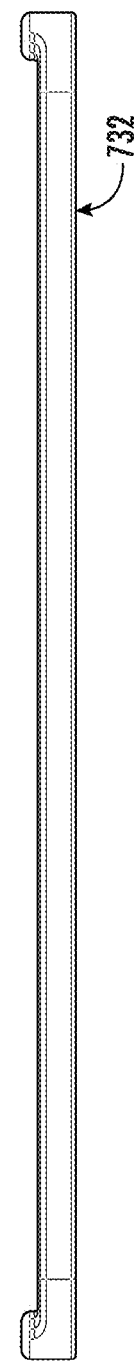
Figure 8A:
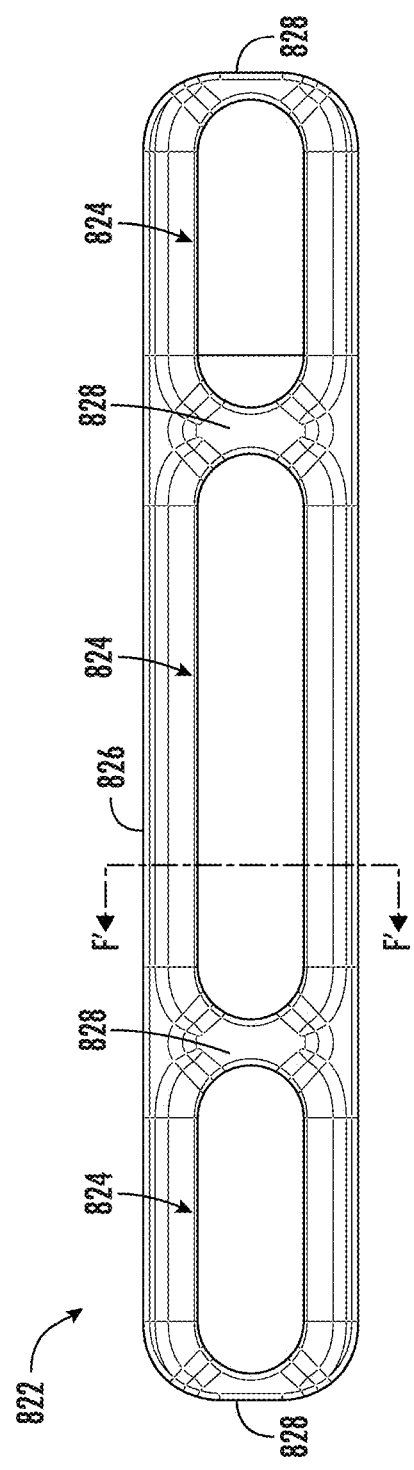
Figure 8B:
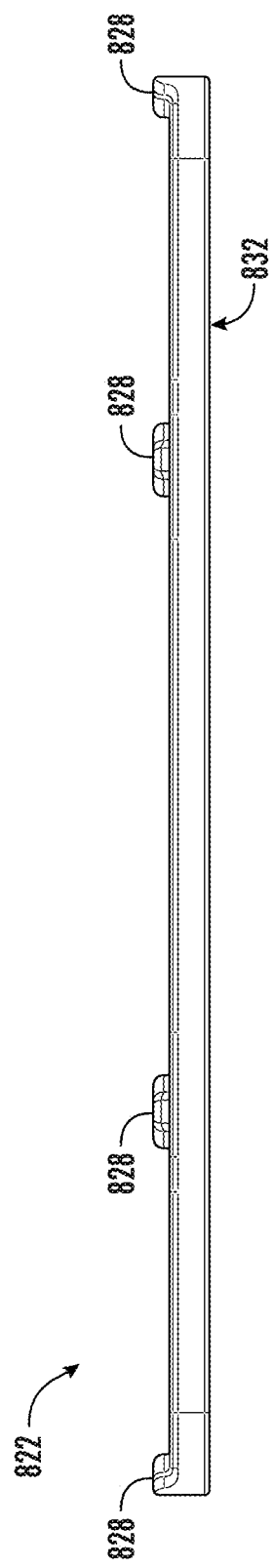
Figure 8C:
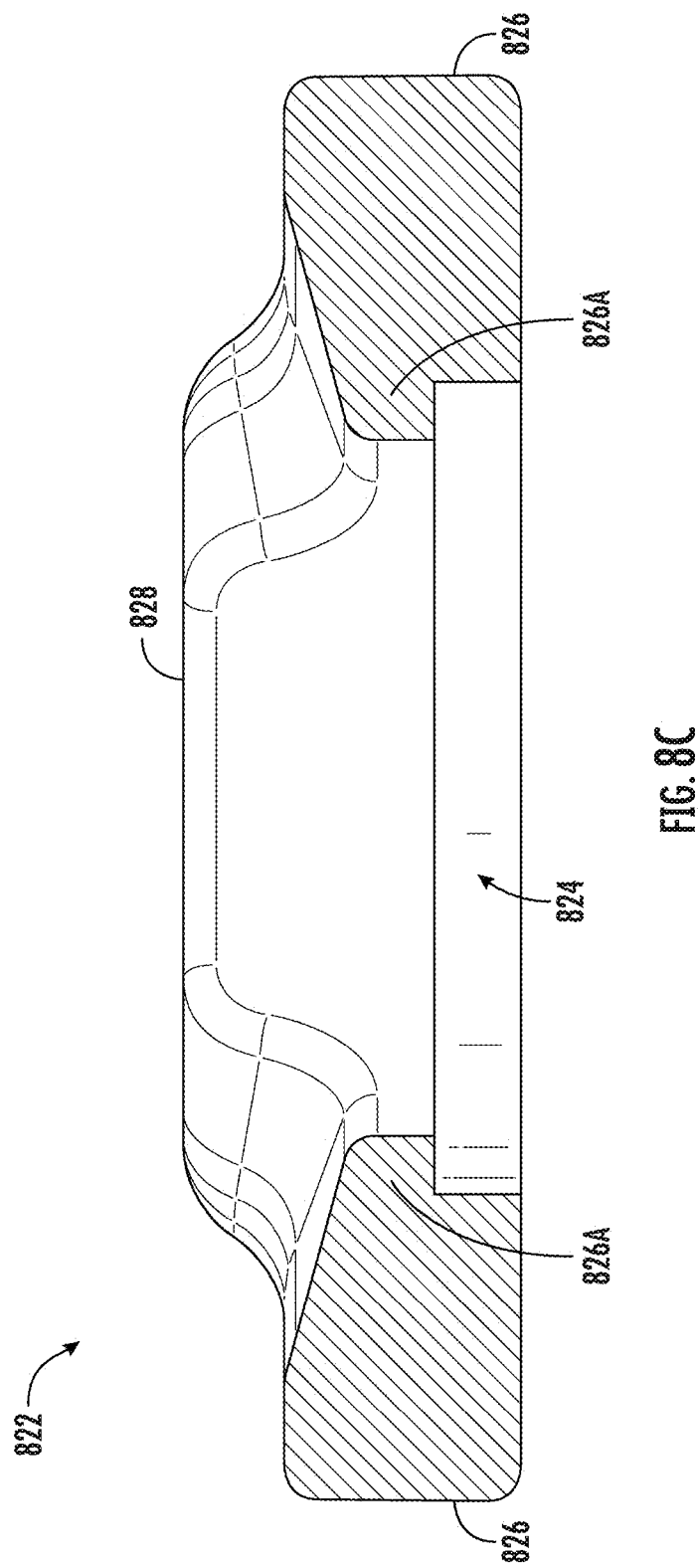
Figure 9B:
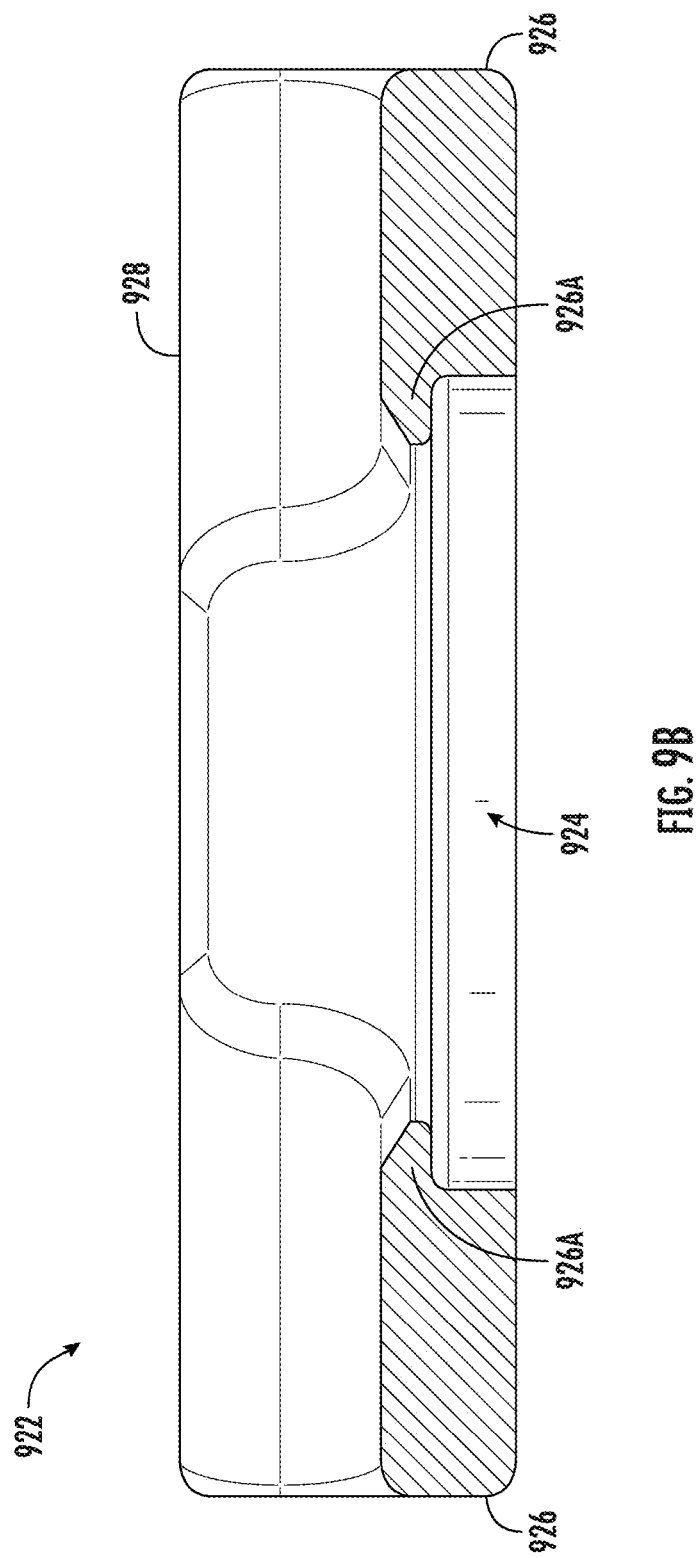
Figure 9D:
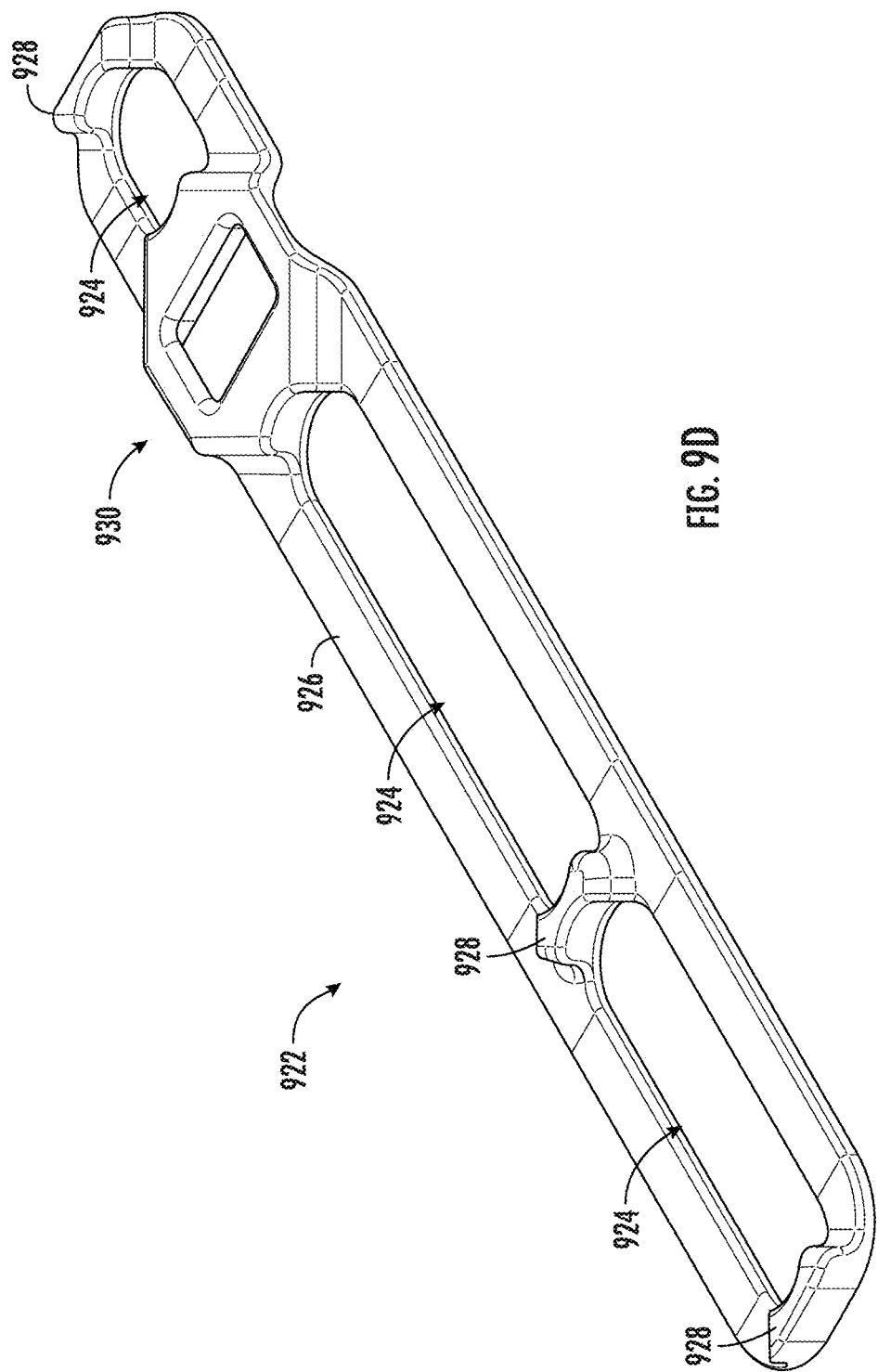
Figure 10A:
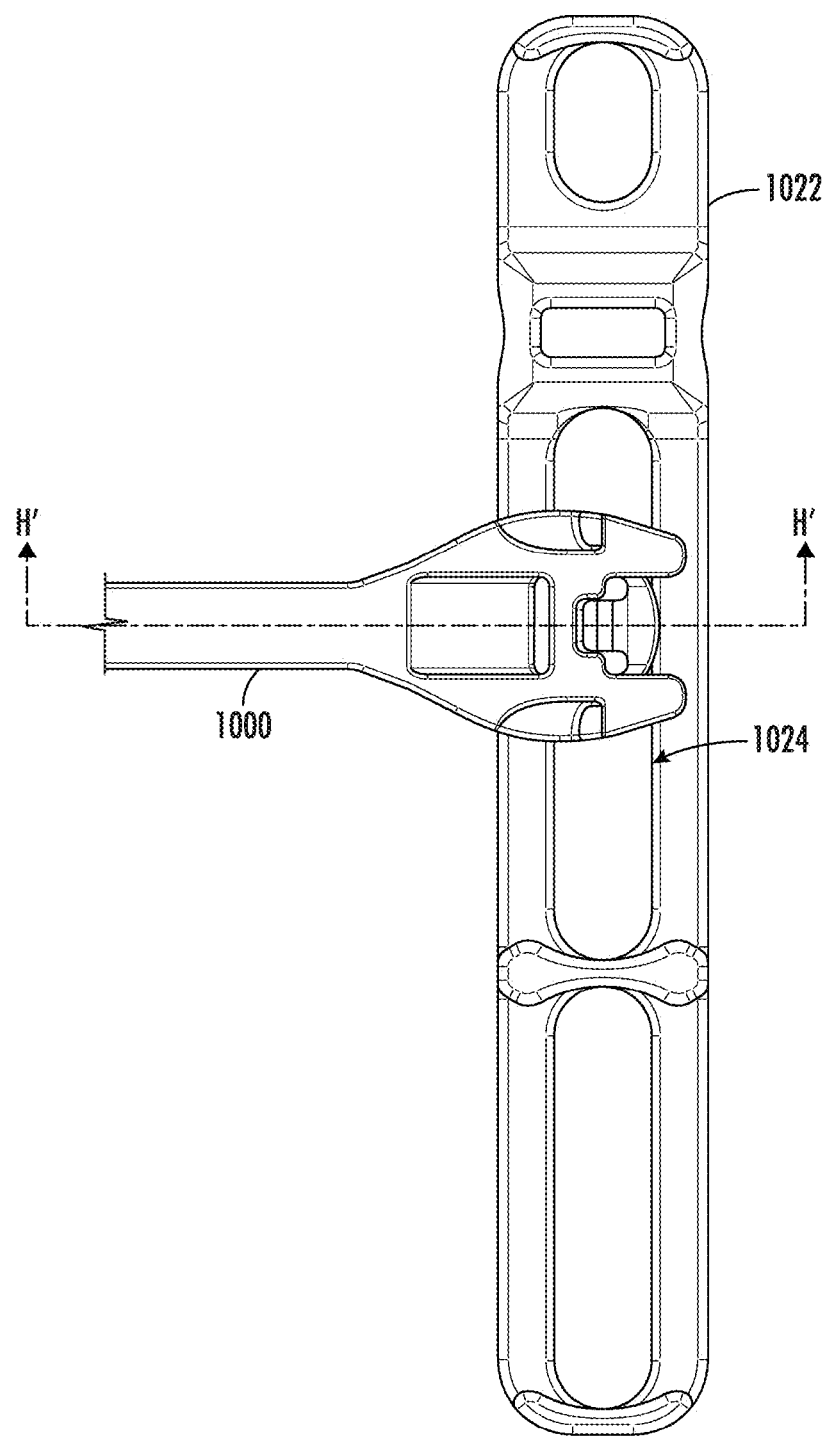
Figure 10B:
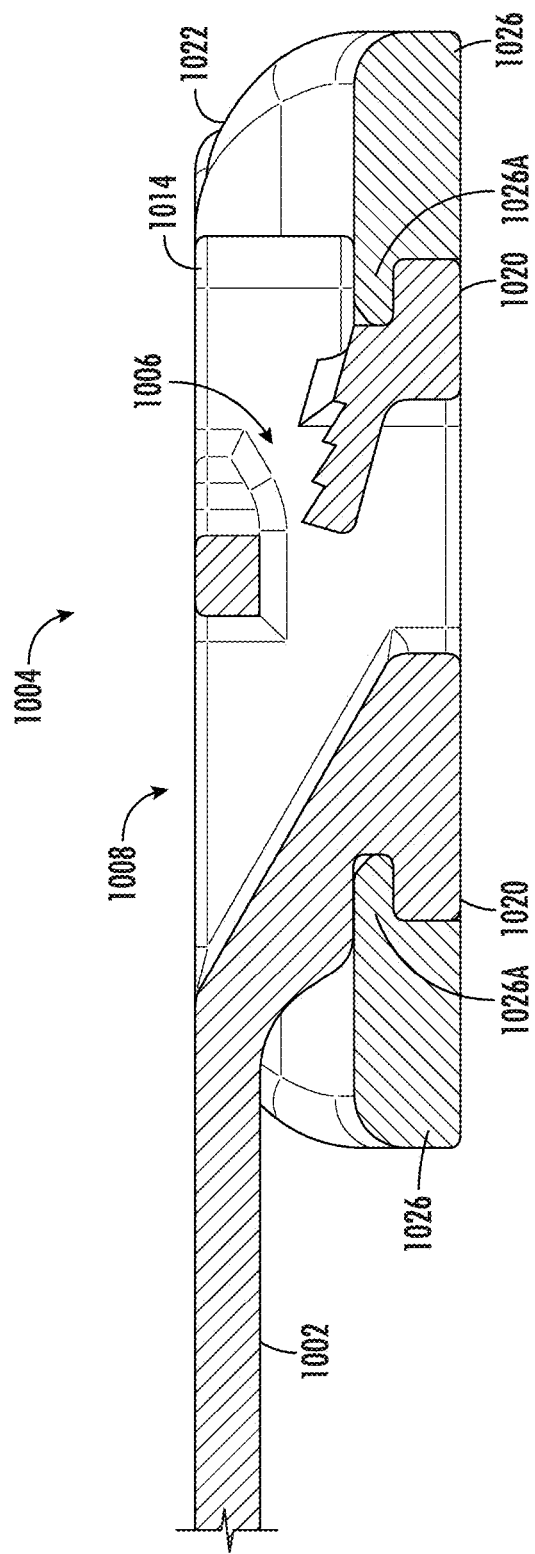
Figure 10C:
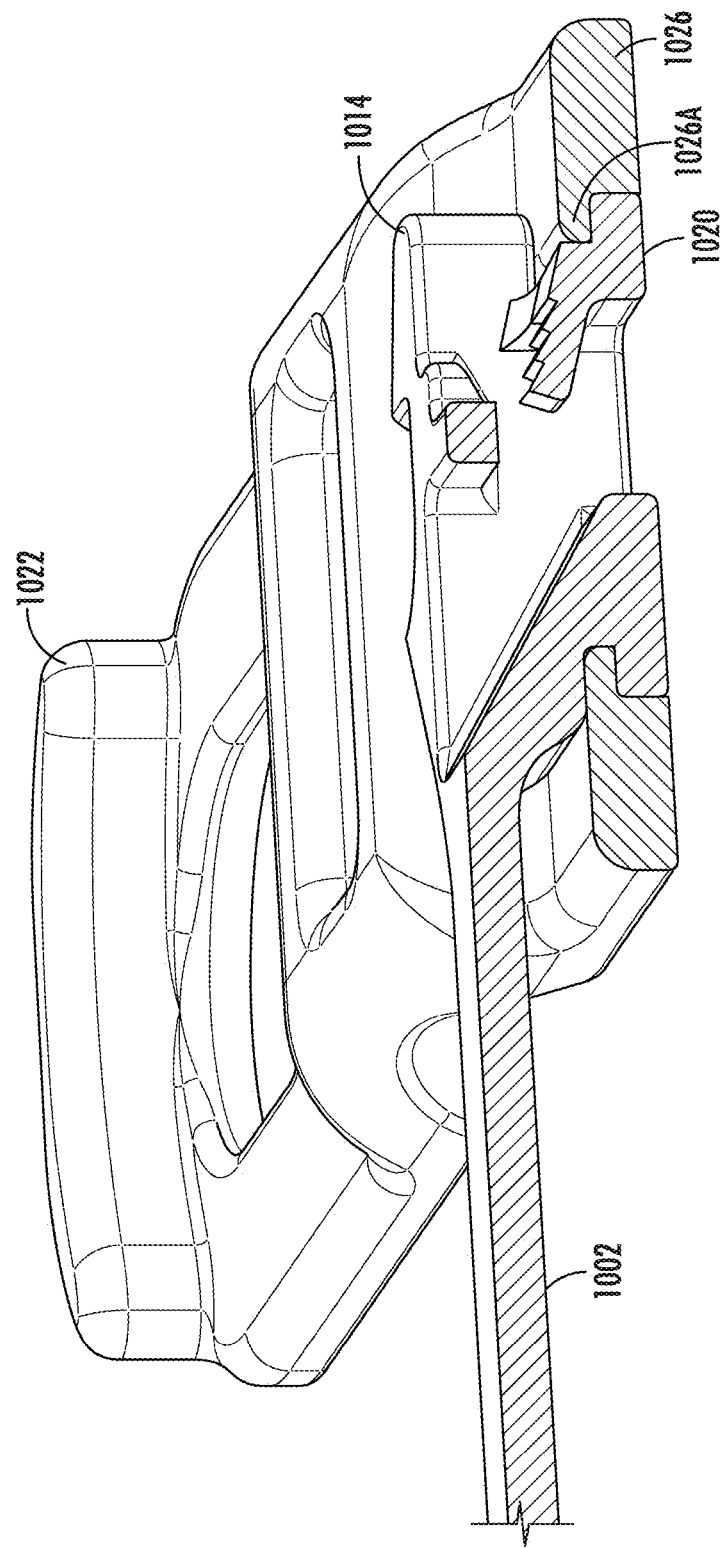
Figure 10E:
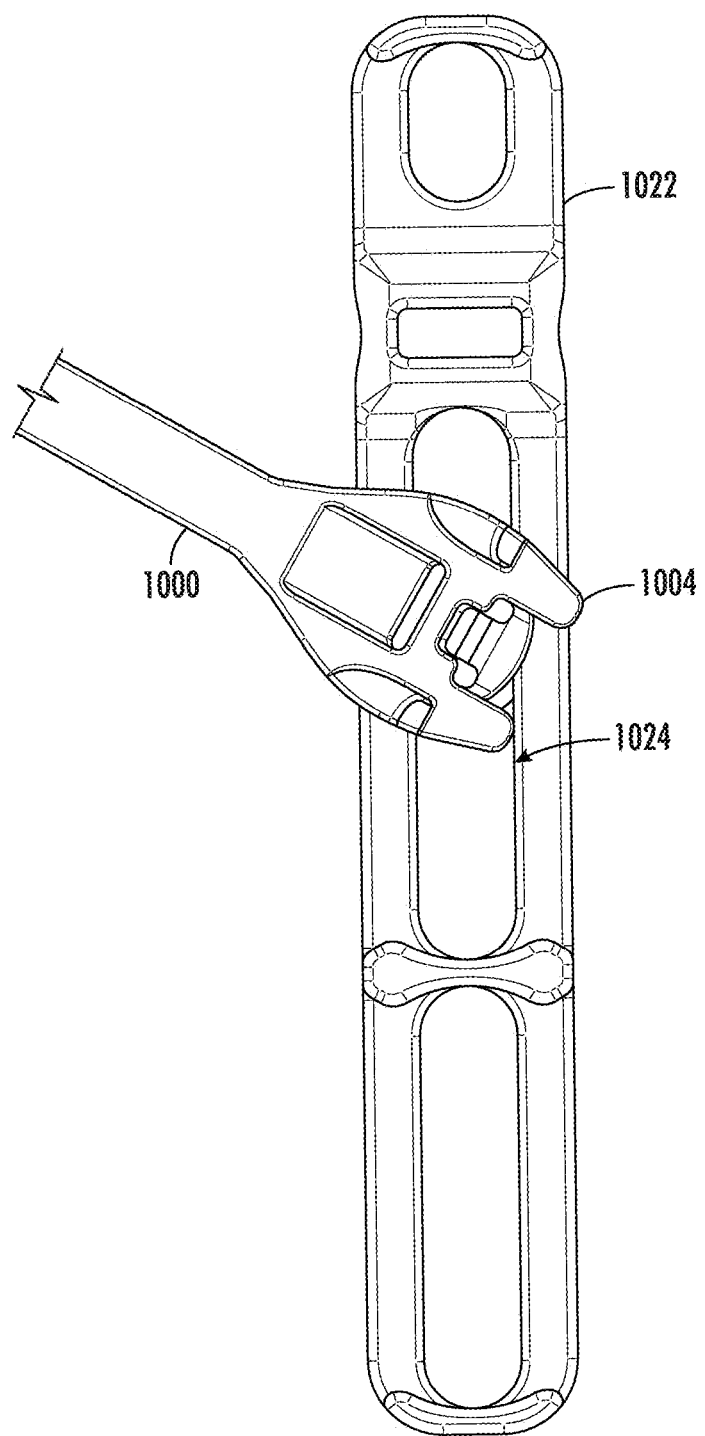
Figure 11A:
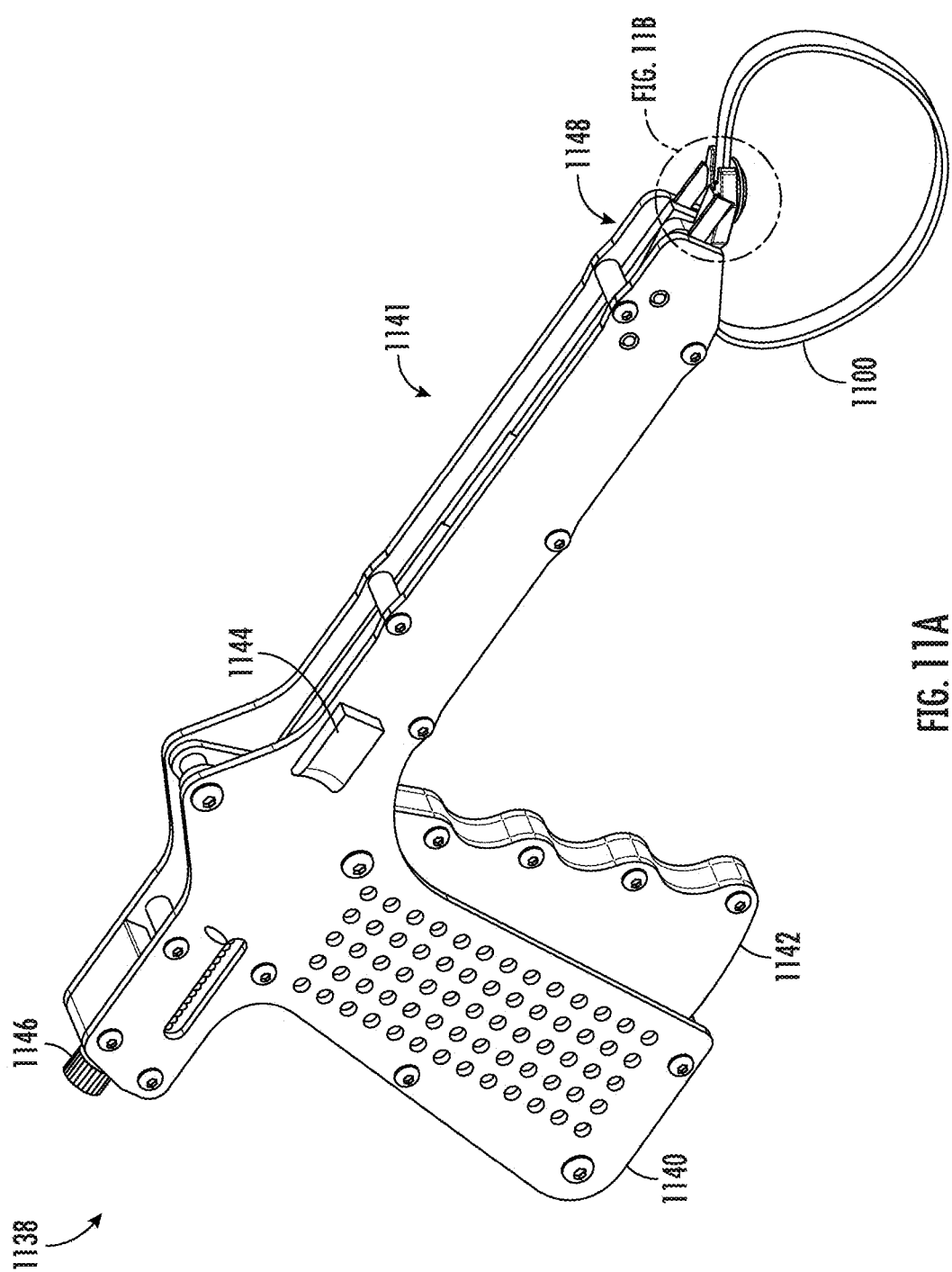
Figure 14:
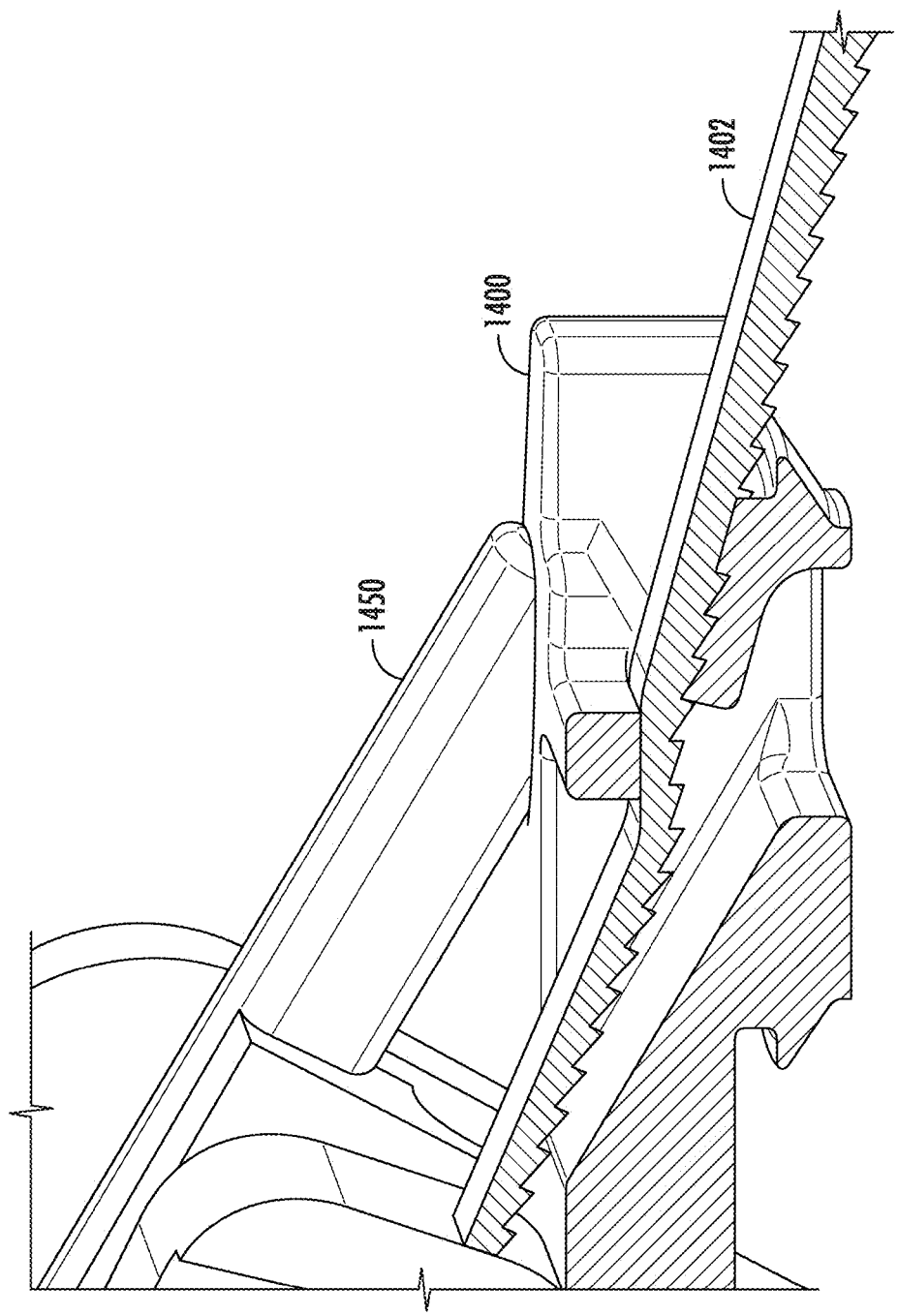
Figure 15:
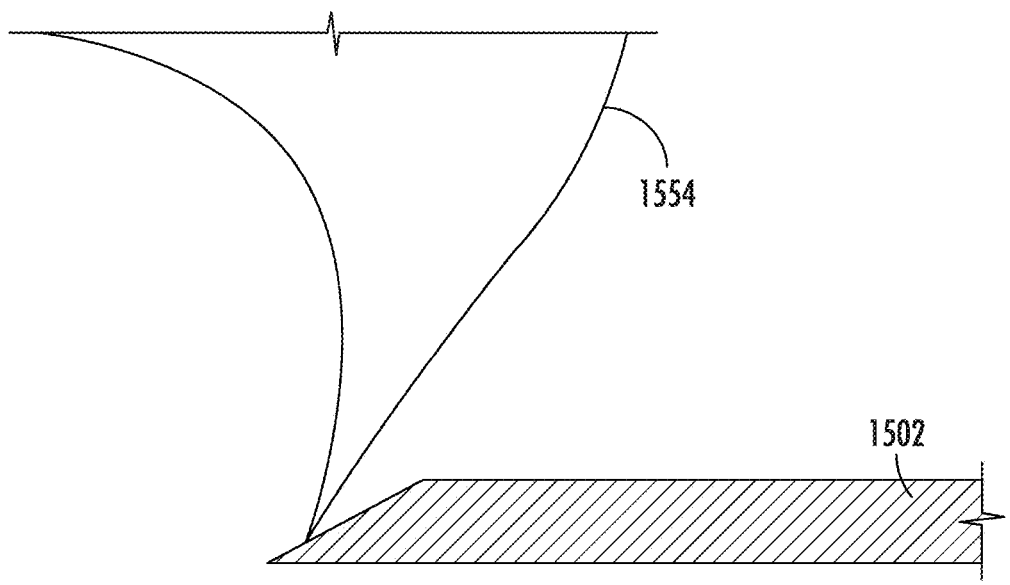
Figure 16A:
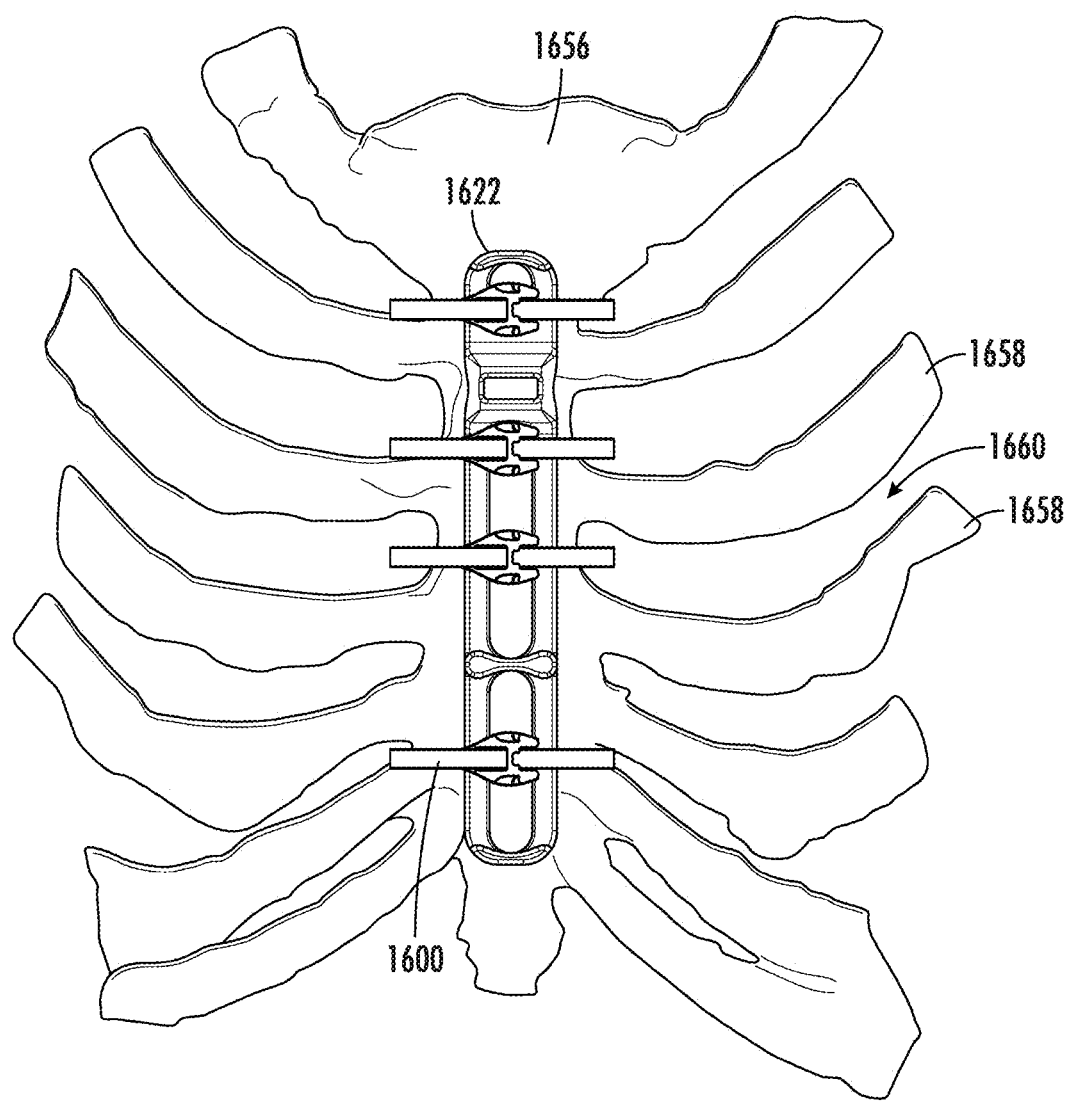
Figure 18A:
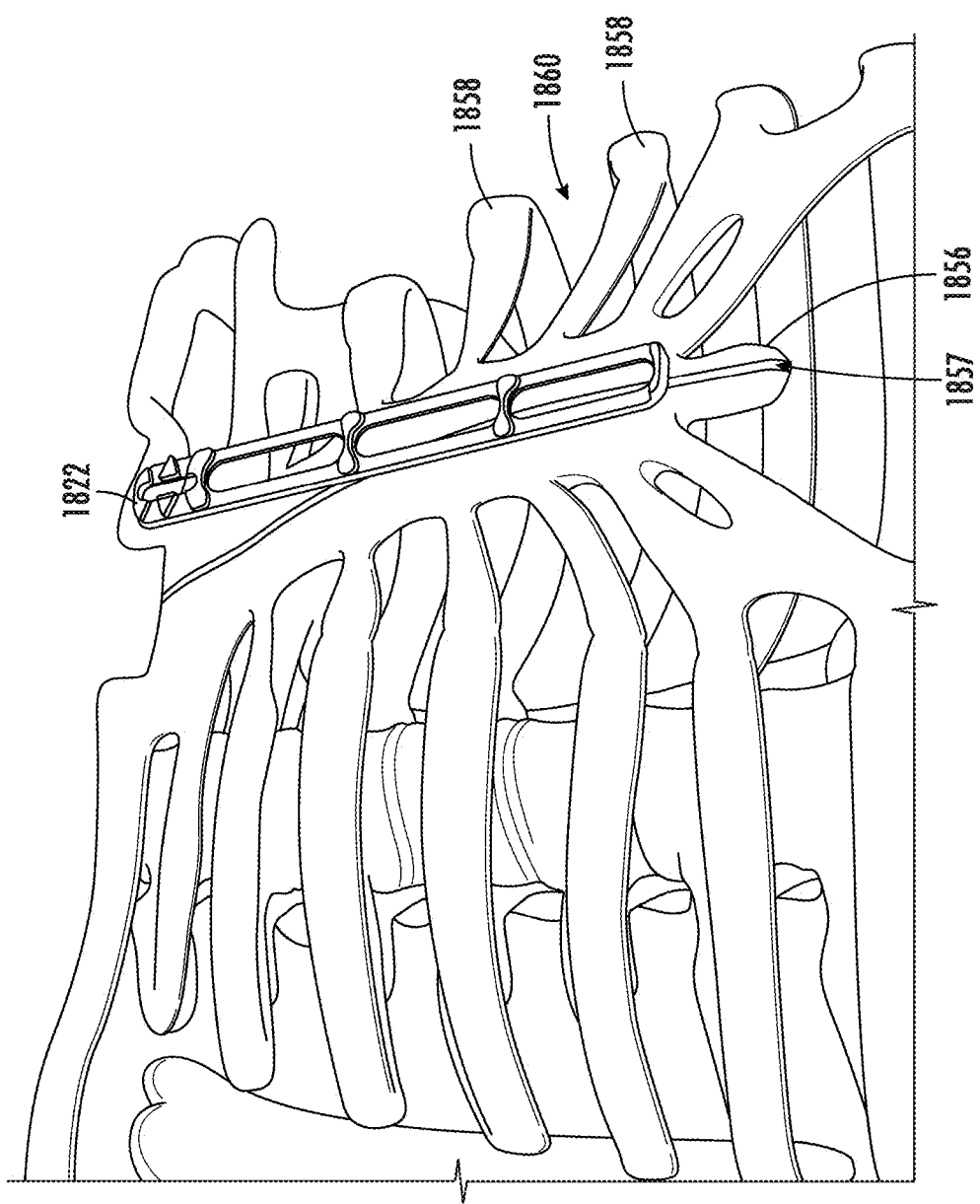
Figure 18B:
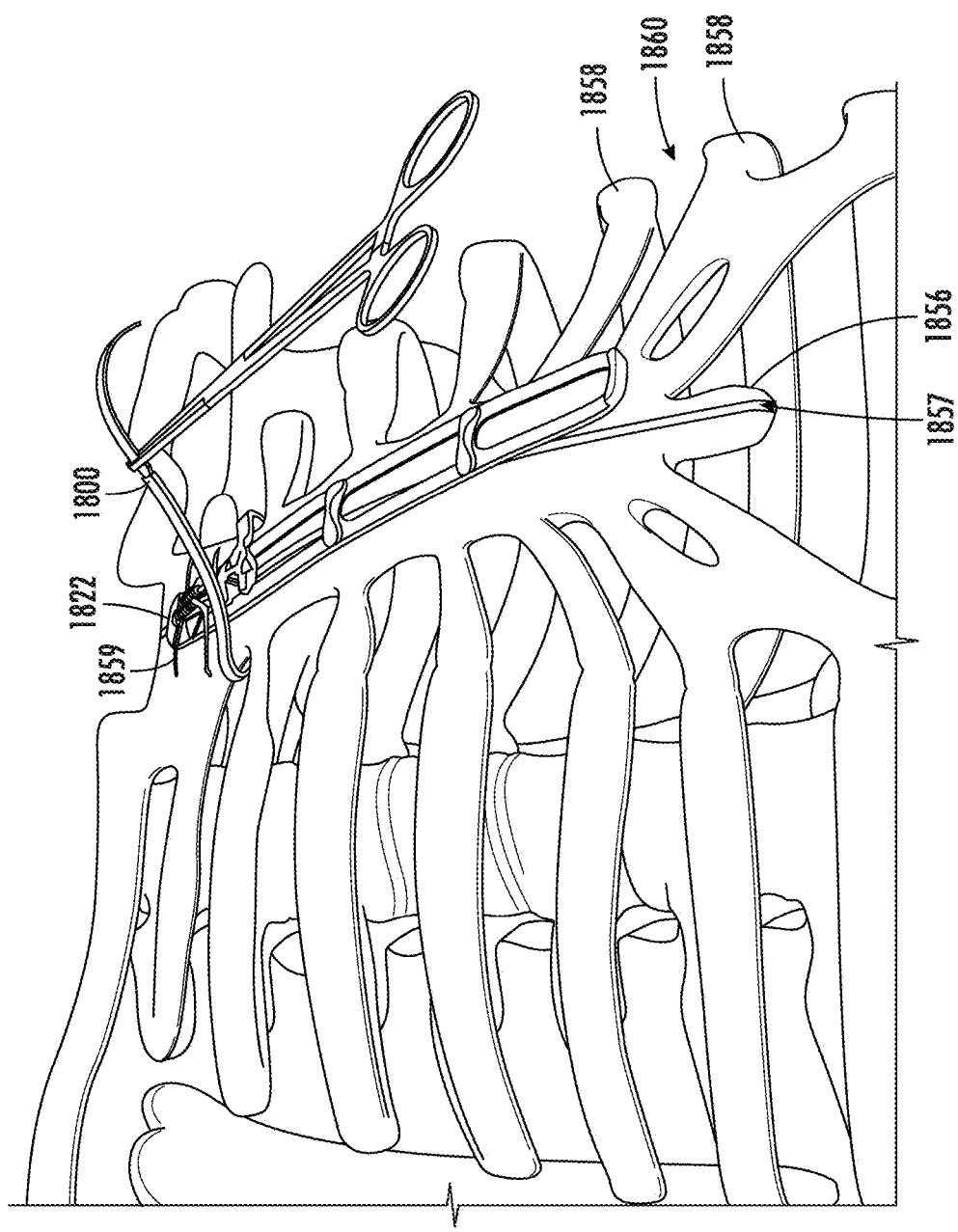
Figure 18C:
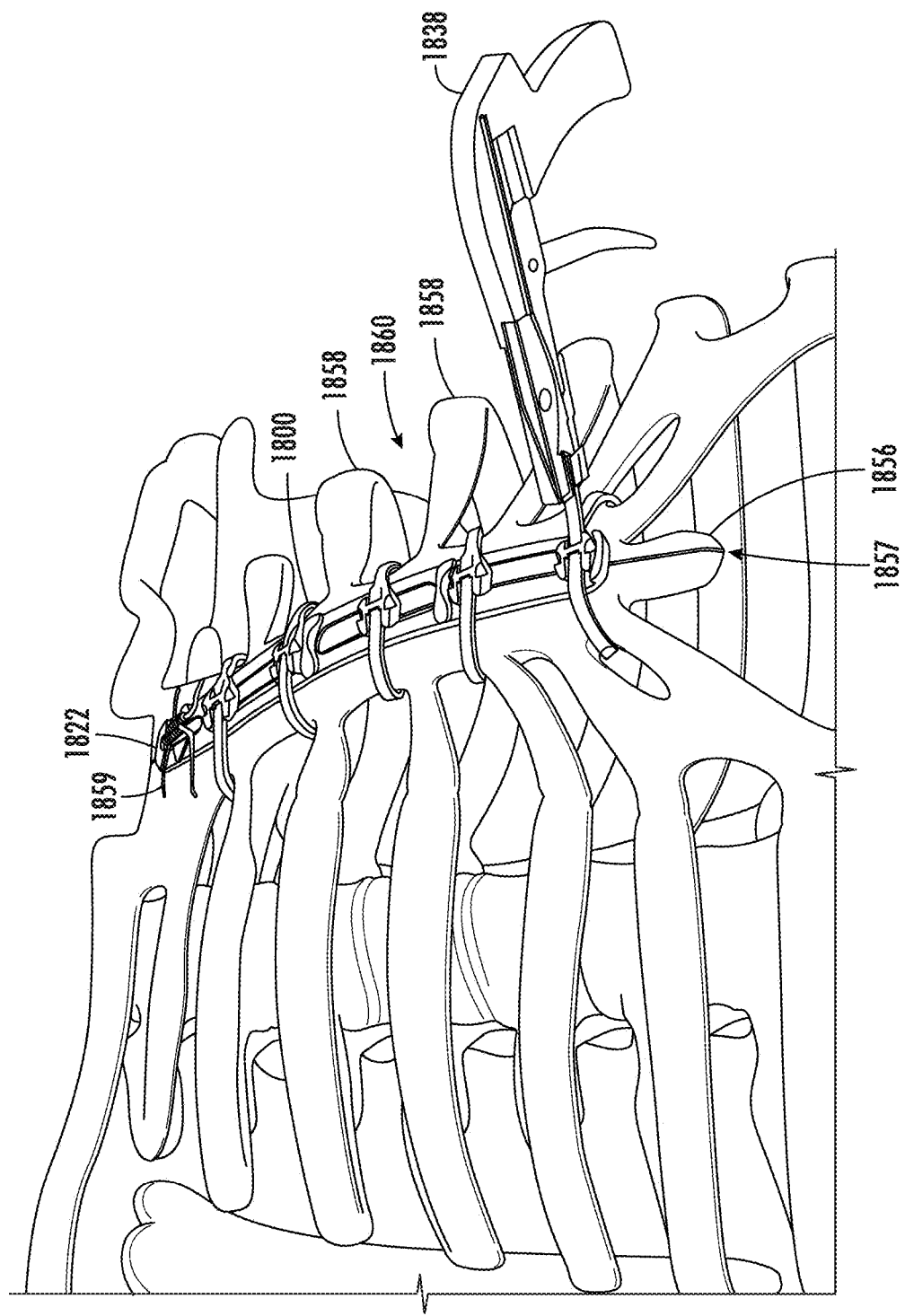
Figure 19A:
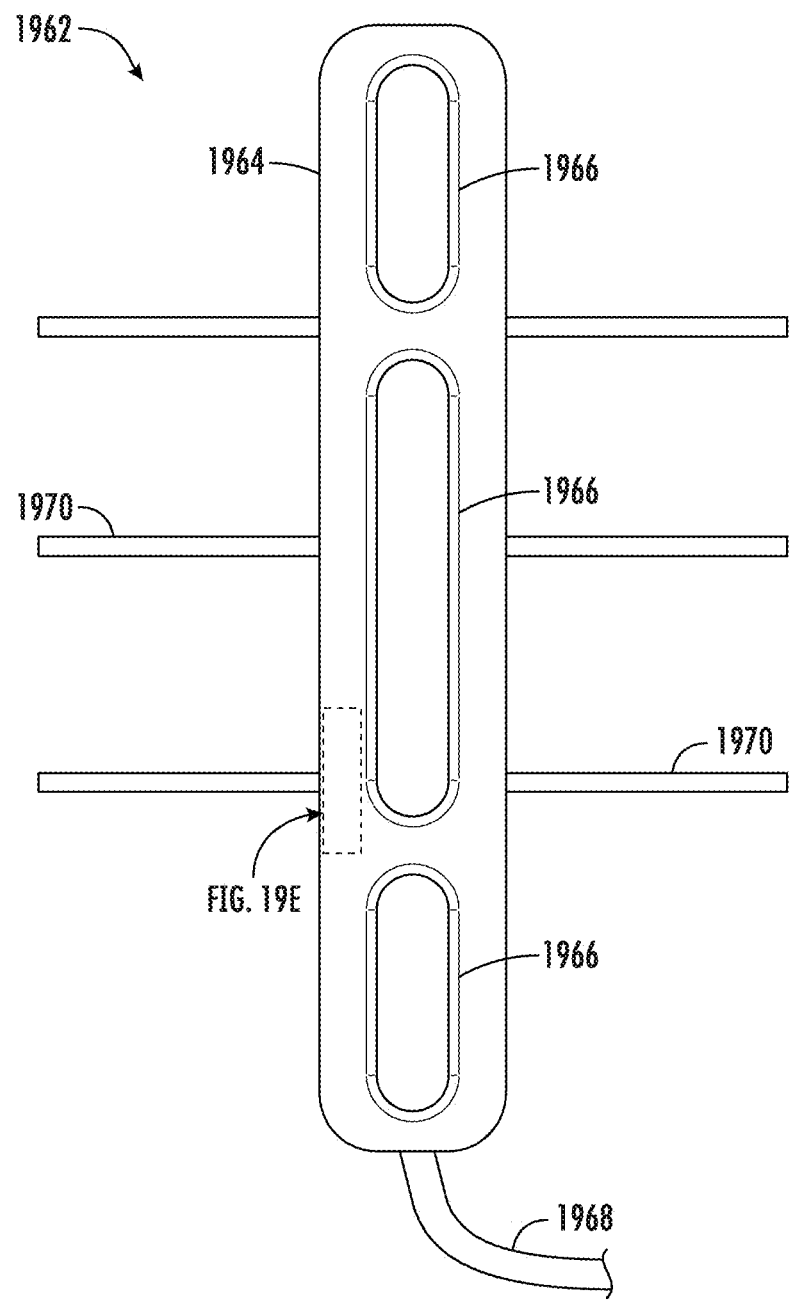
Figure 19C:
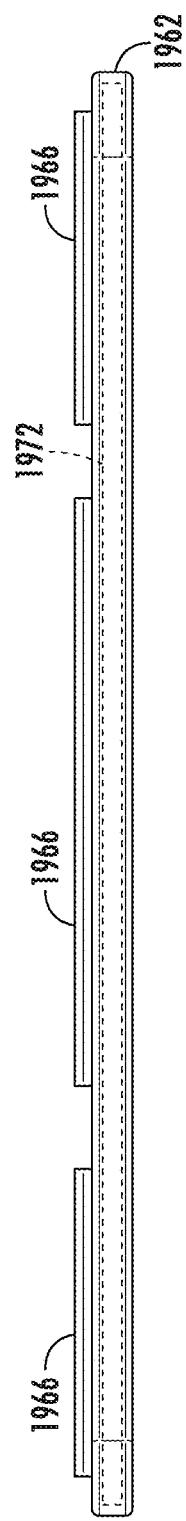
Figure 19D:
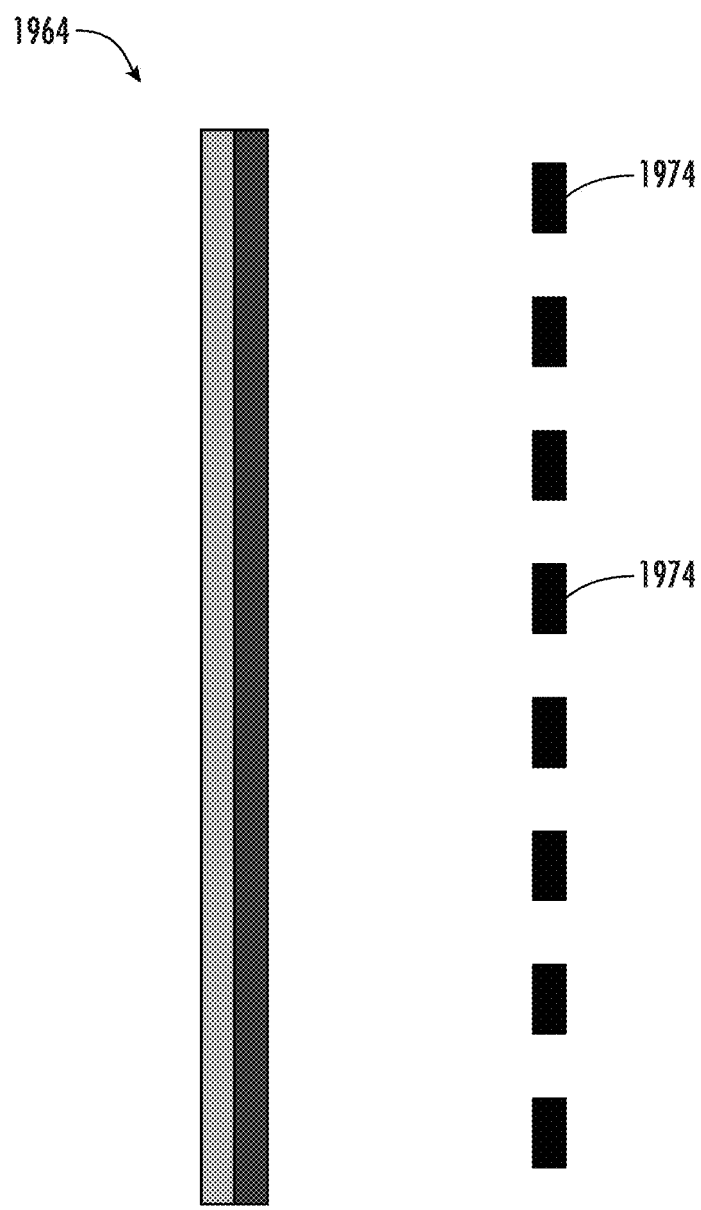
Figure 19E:
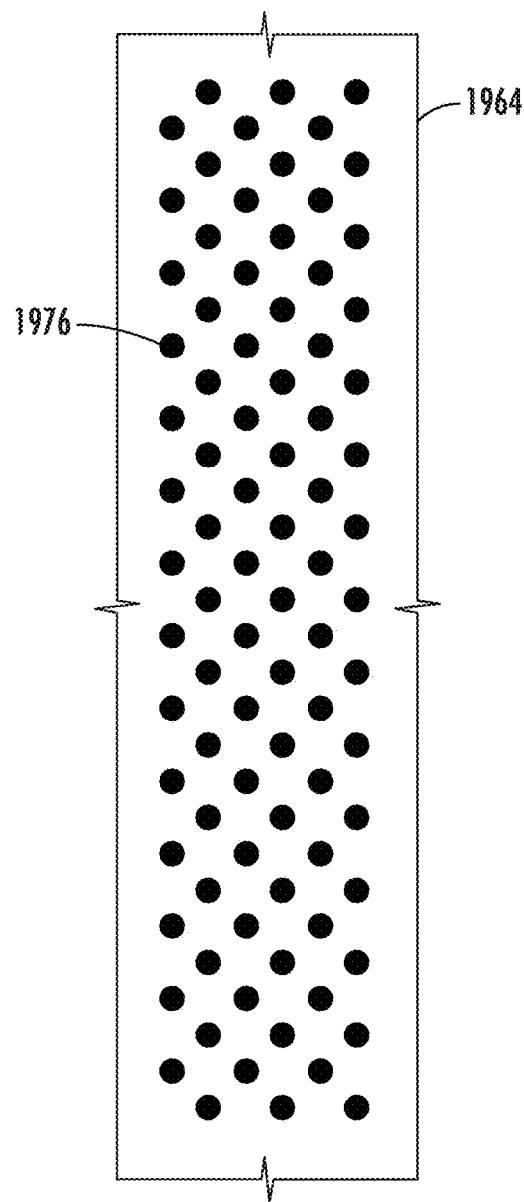
Figure 19F:
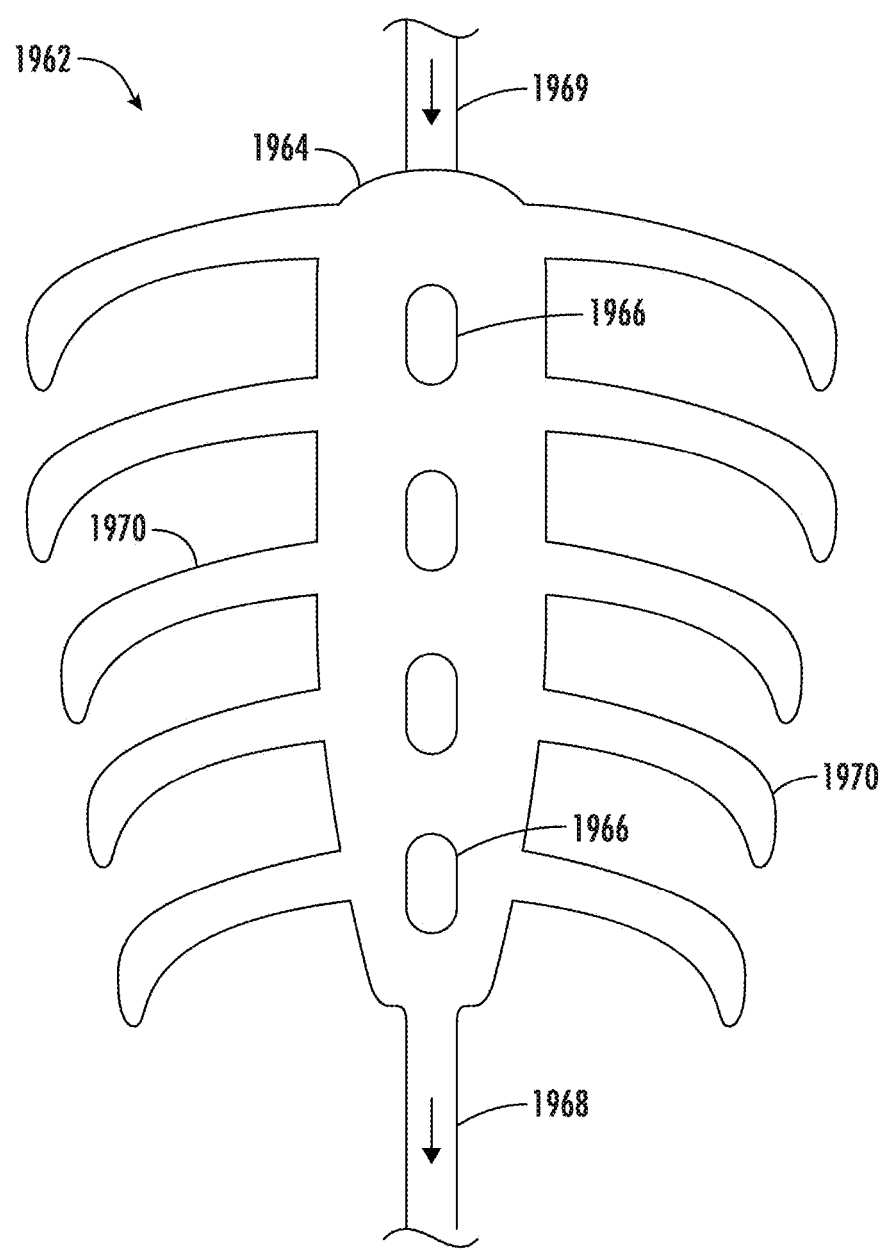
Figure 19G:
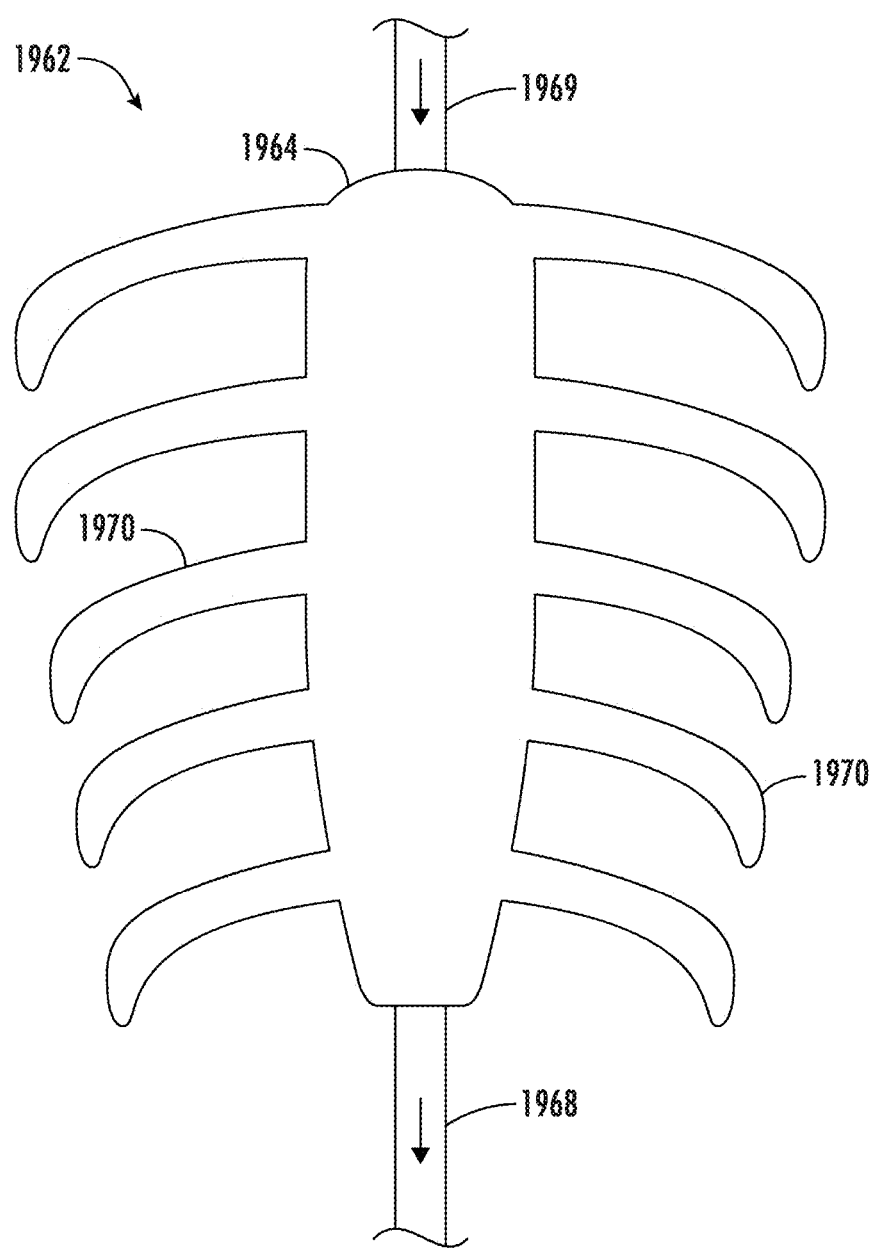
Figure 20:
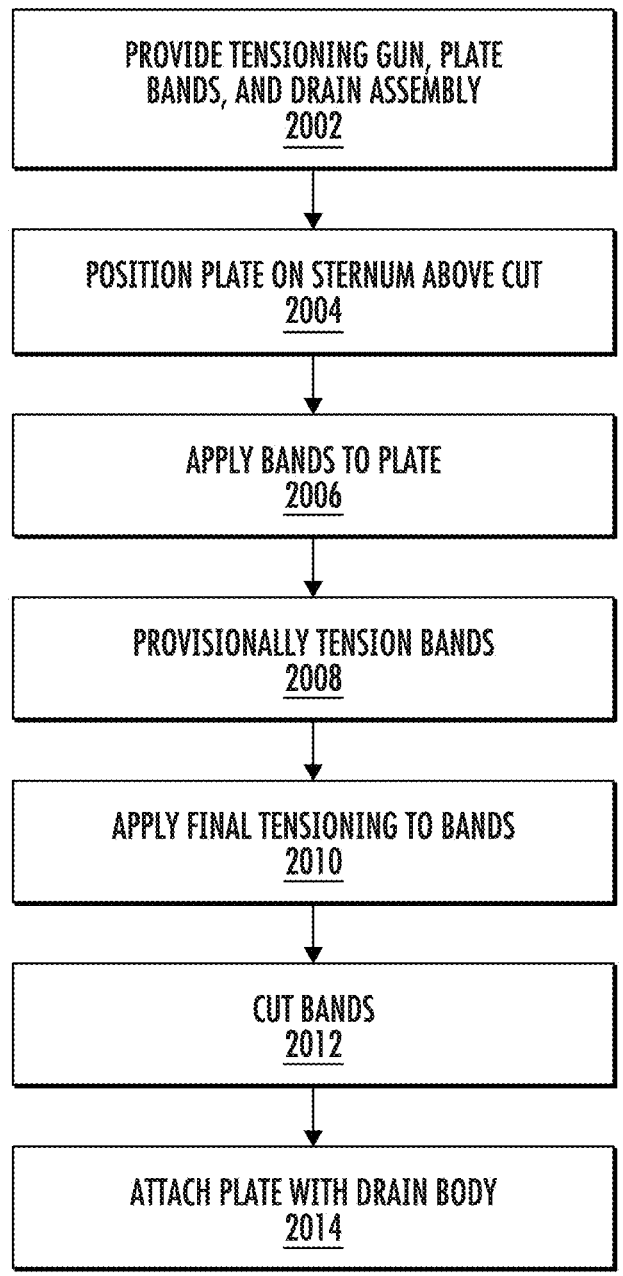
Figure 21:
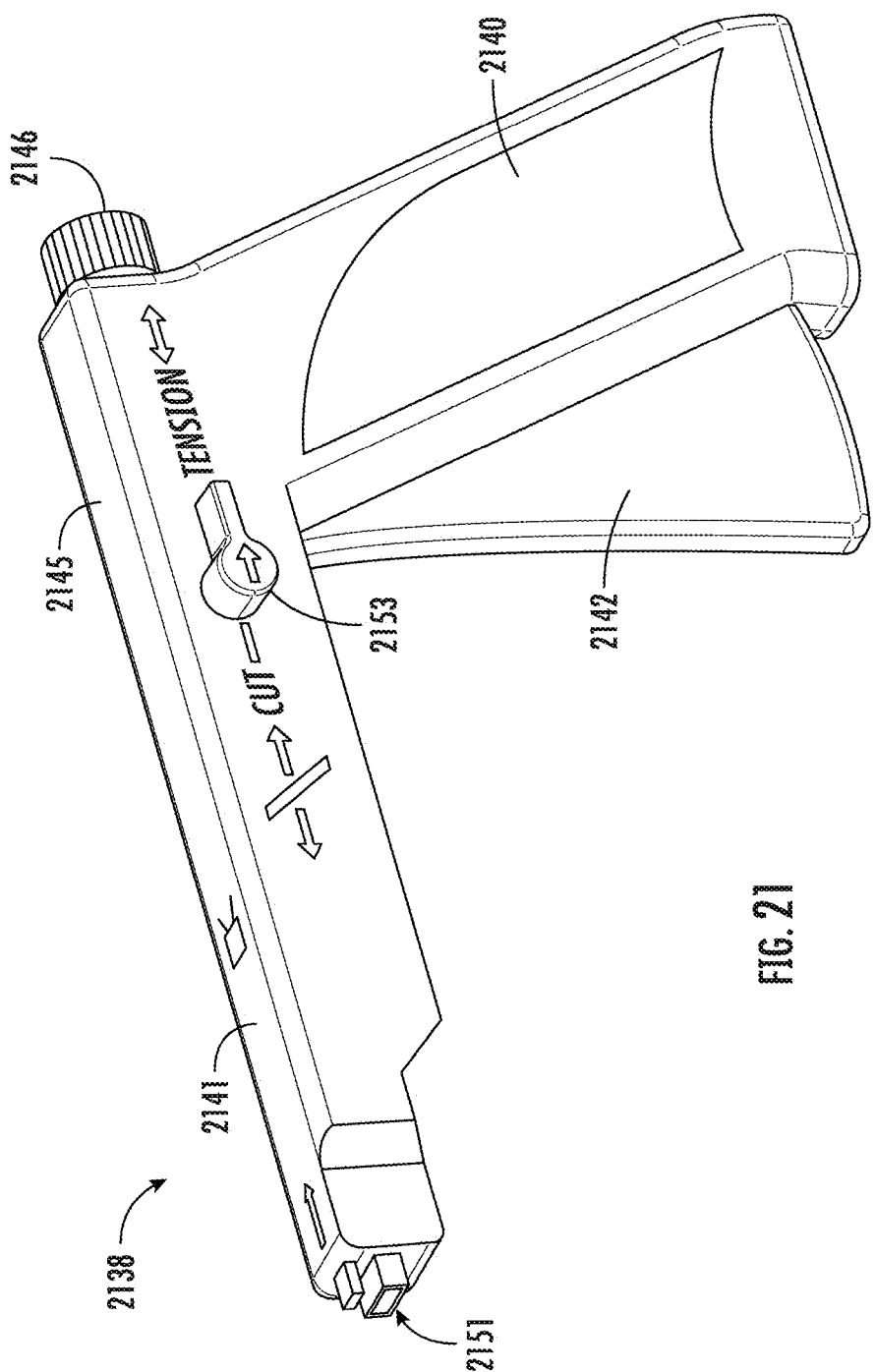
Figure 22:
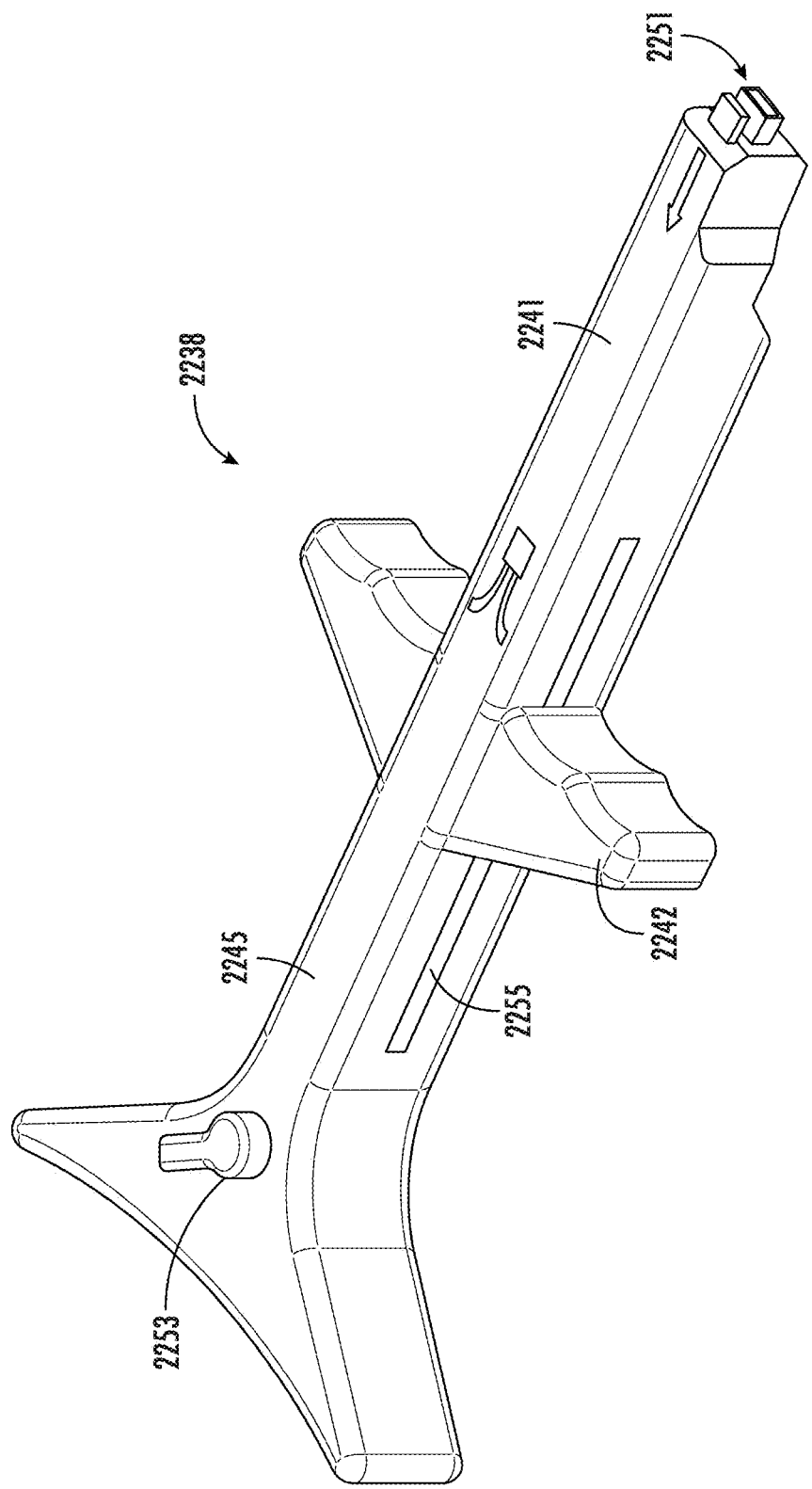
Figure 23:
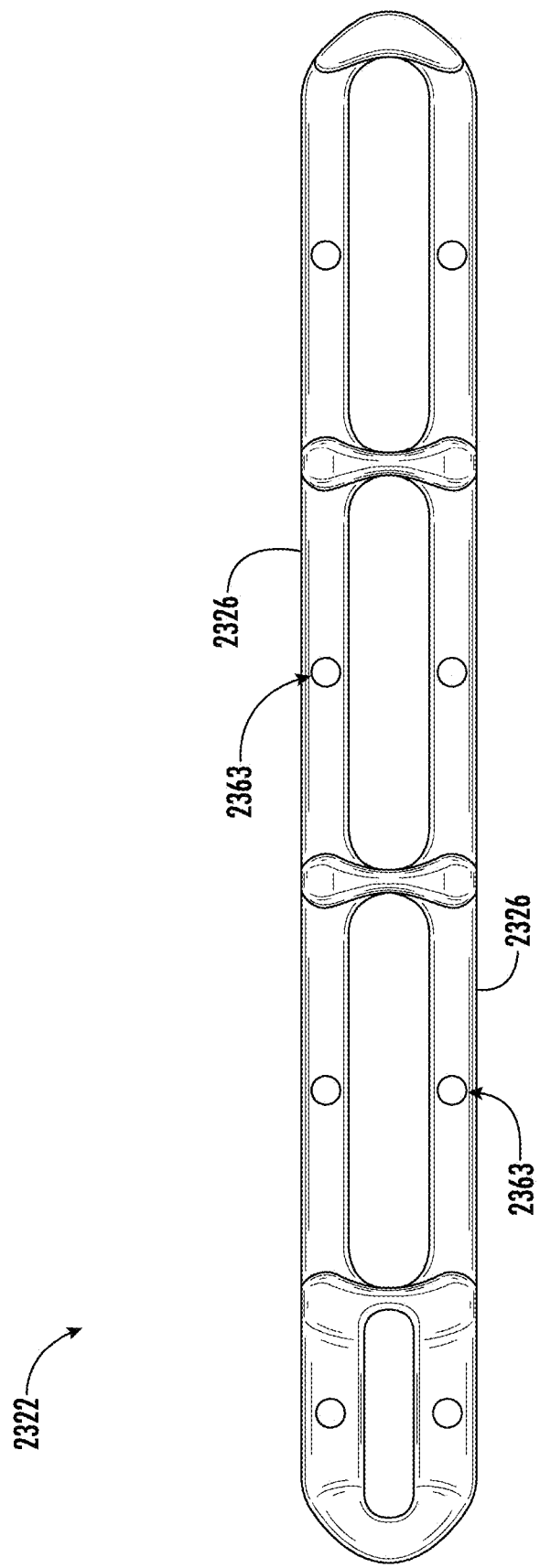
Figure 24A:
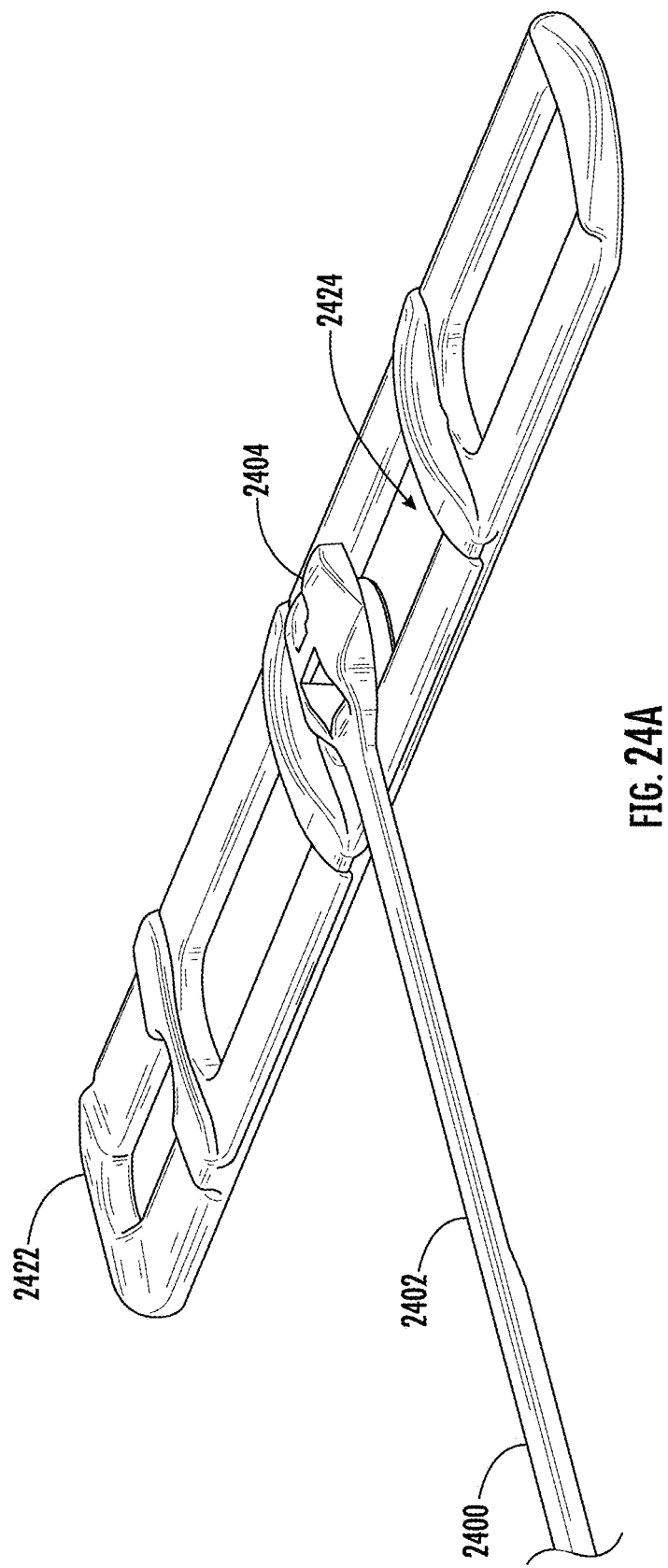
Figure 24B:
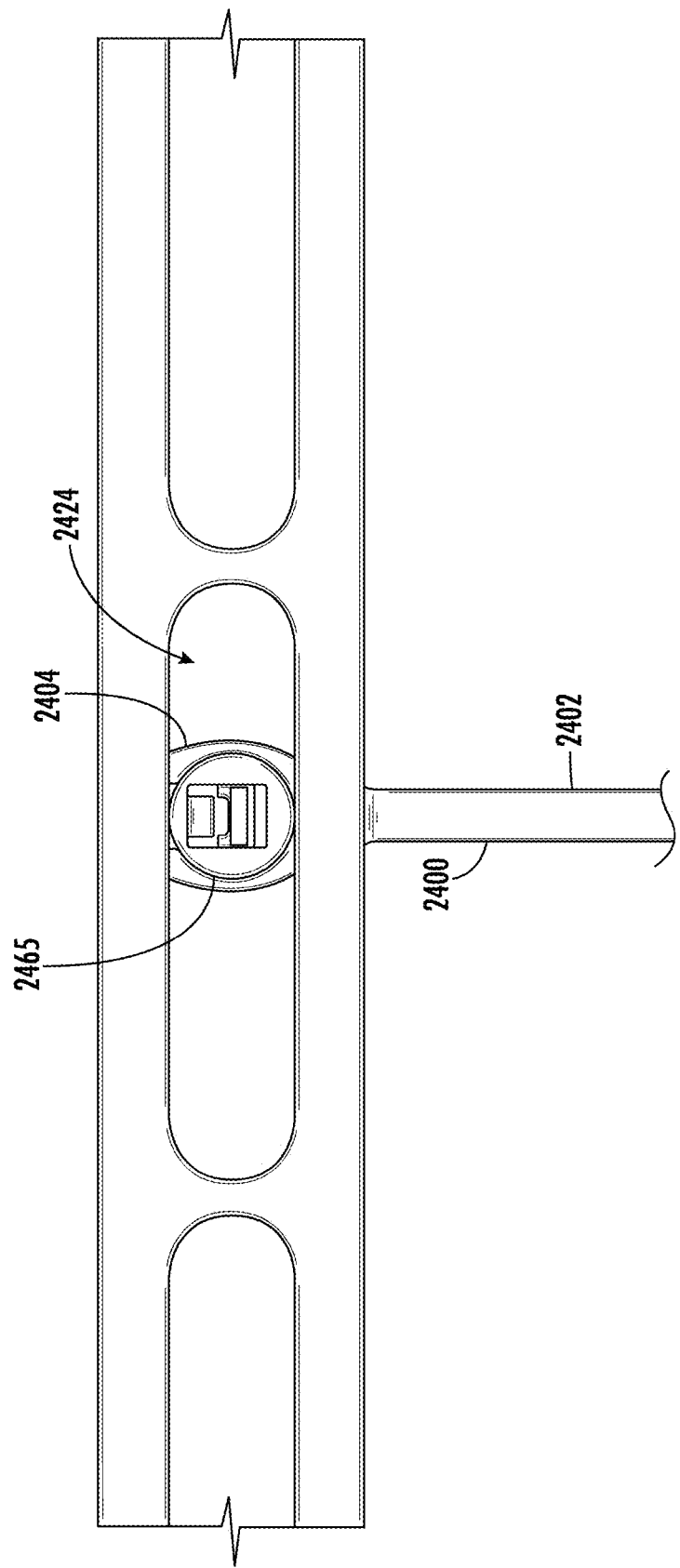
Figure 24E:
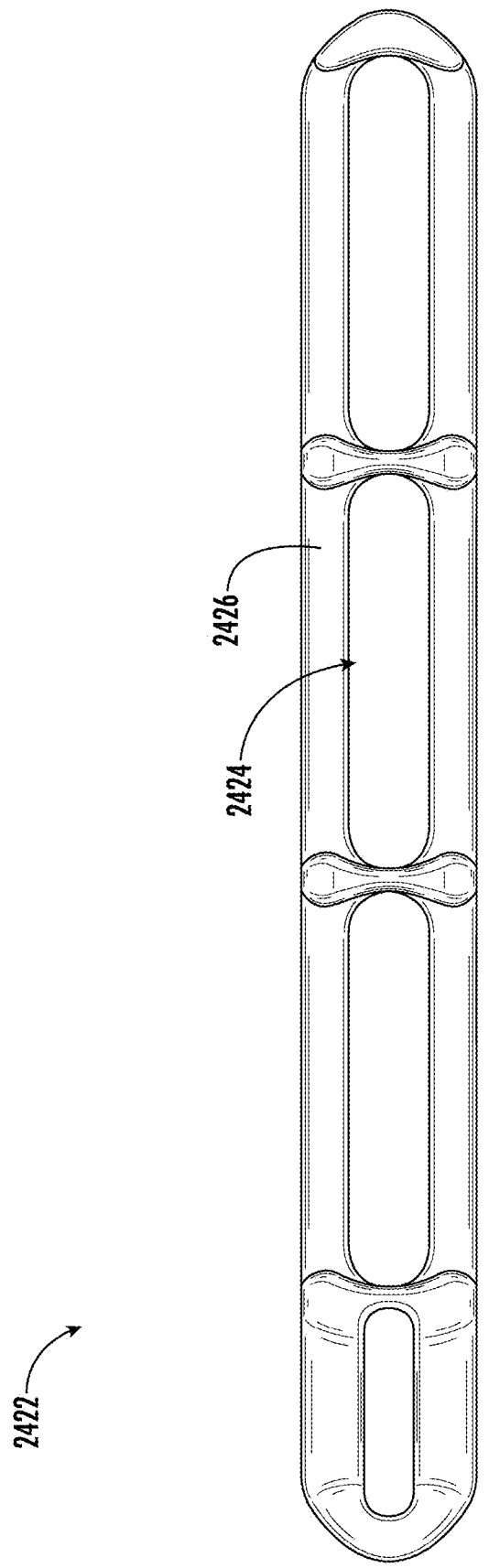
Figure 25A:
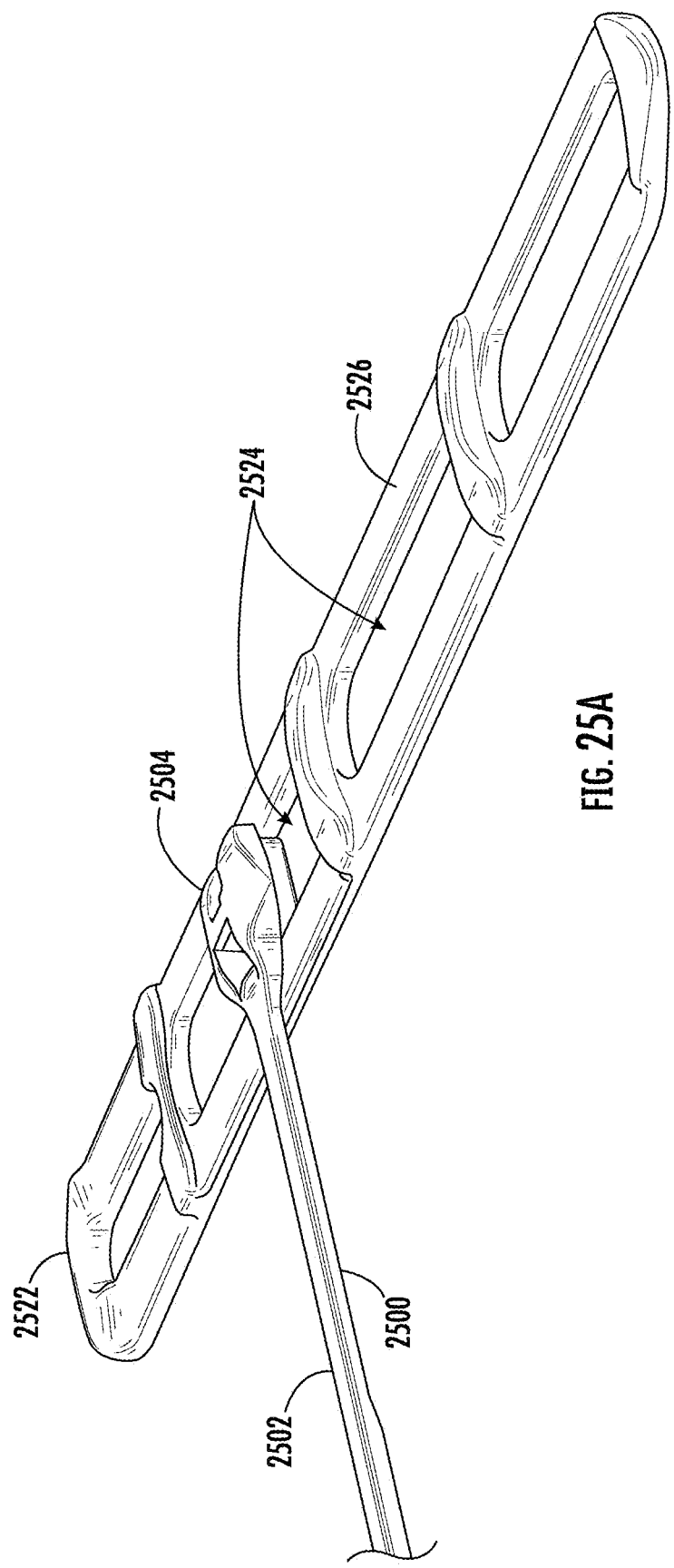
Figure 25C:
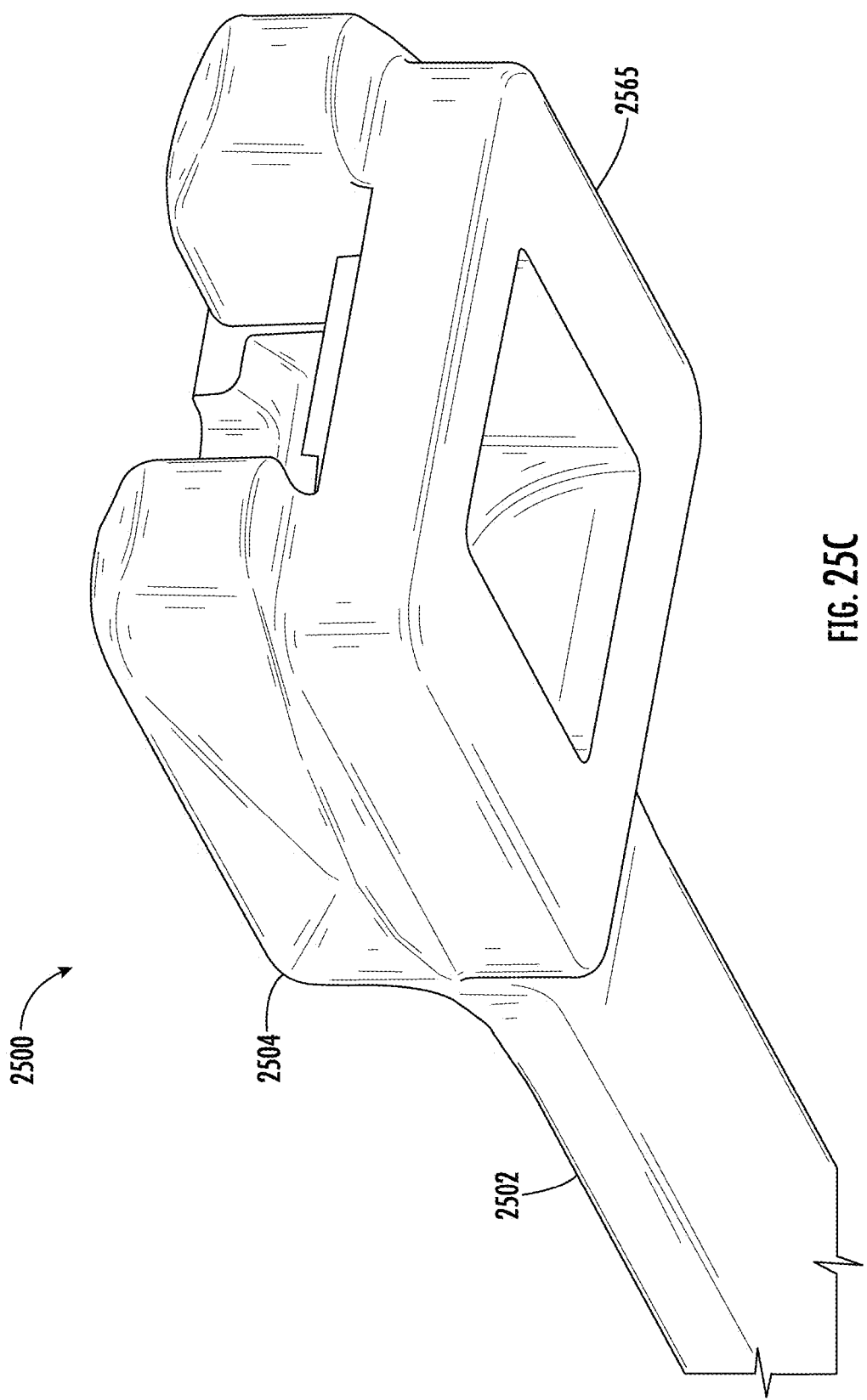
Figure 25D:
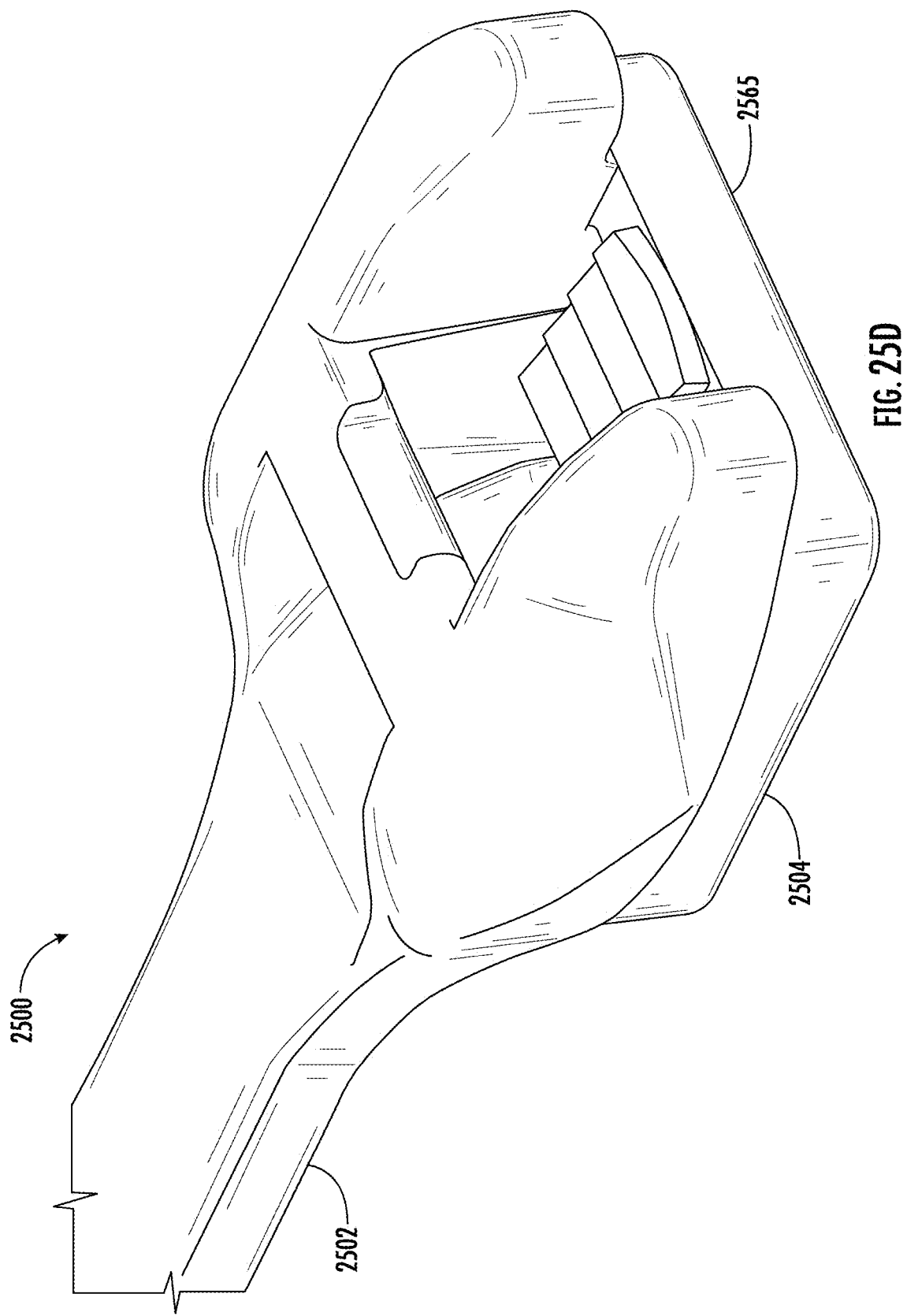
Figure 26B:
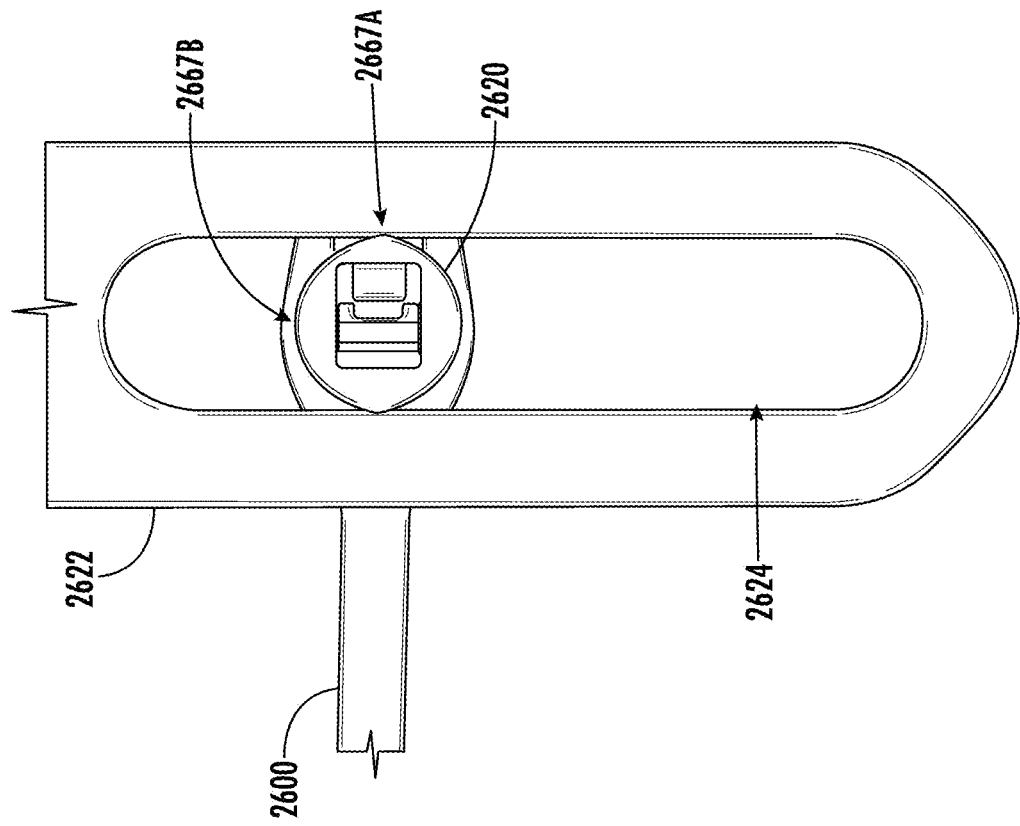
Figure 26A:
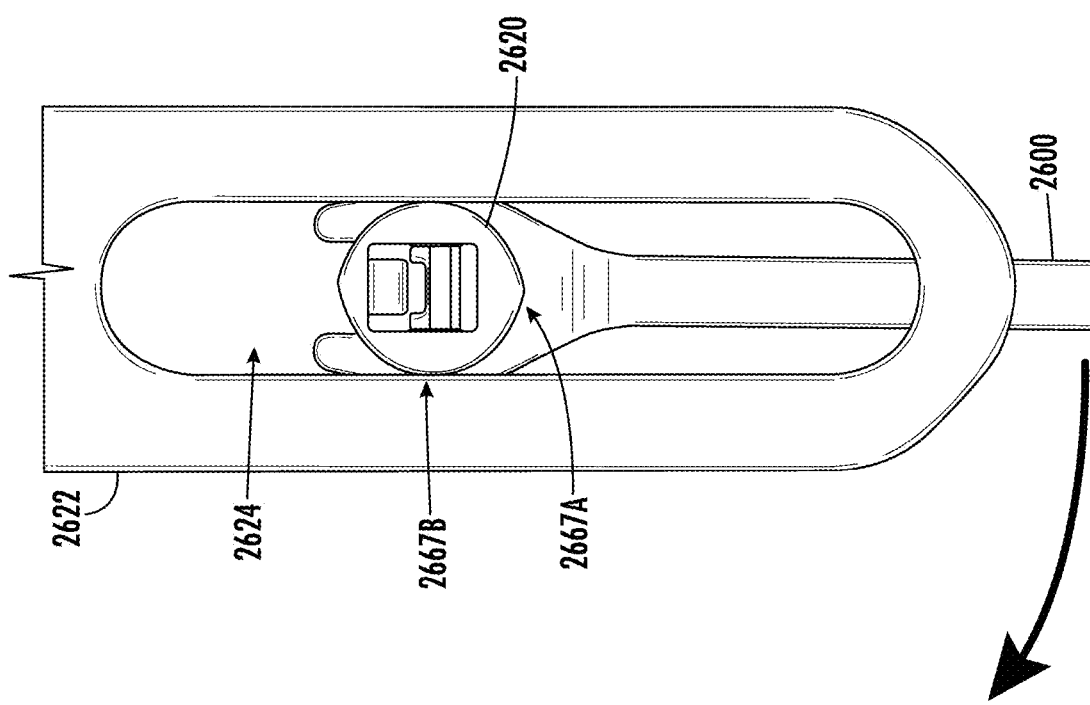
Figure 26C:
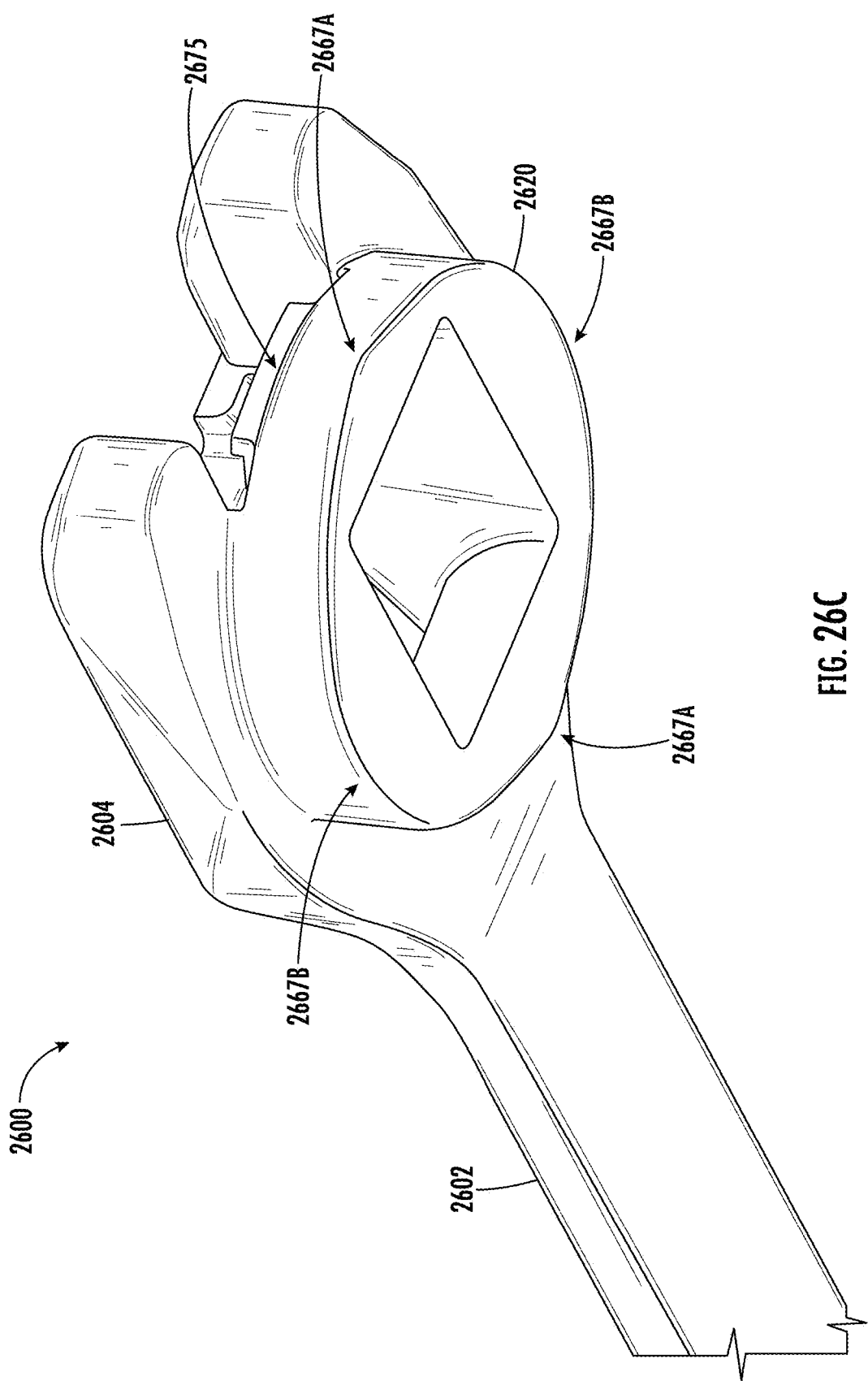
Figure 26D:
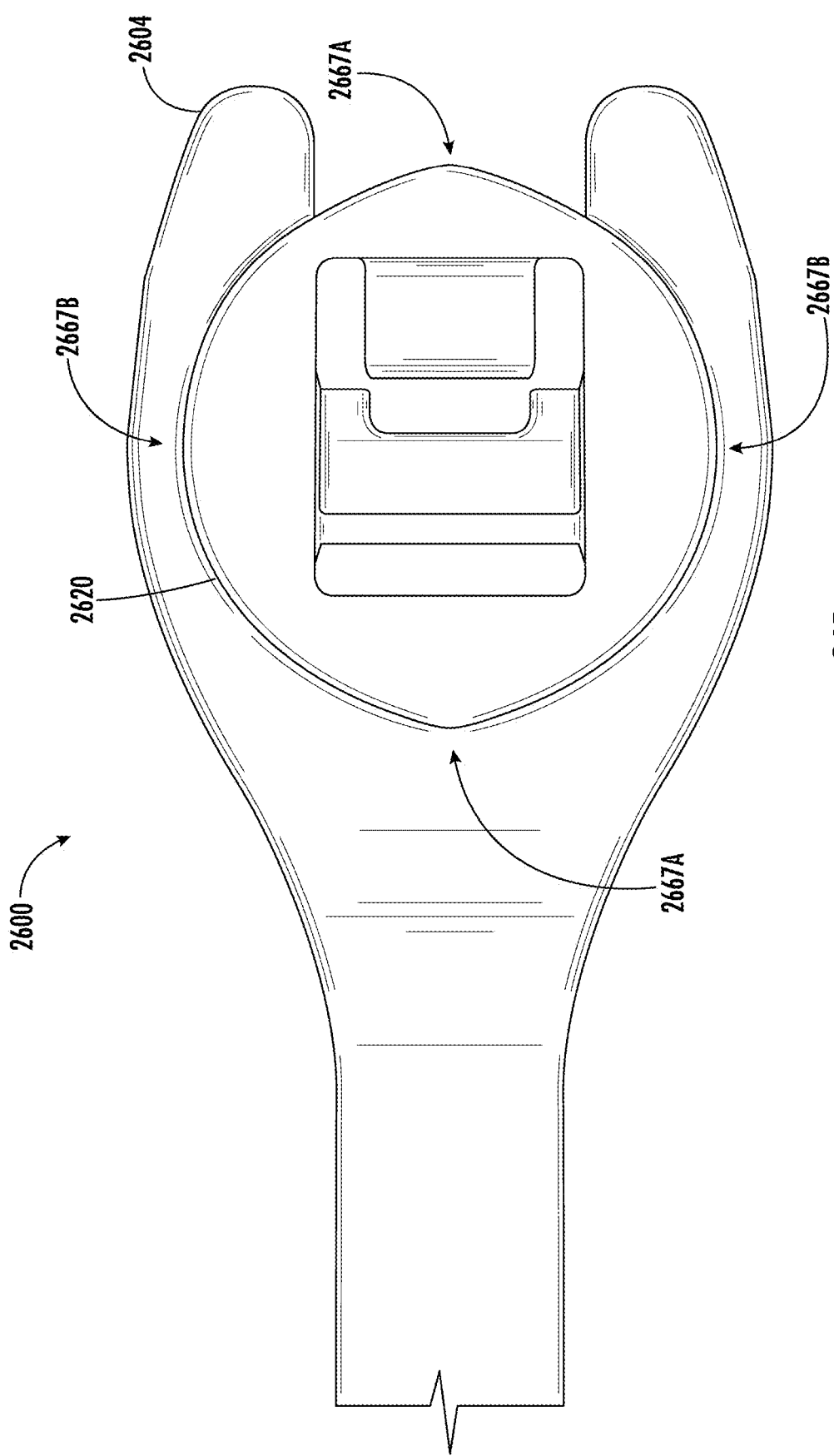

Having thus described the invention in general terms, reference will now be made to the accompanying drawings, which are not necessarily drawn to scale, and wherein:

FIG. 1A illustrates a top view of an example band, in accordance with some embodiments discussed herein;

FIG. 1B illustrates an enhanced top view of a head of the band of FIG. 1A, in accordance with some embodiments discussed herein;

FIG. 1C illustrates an enhanced side view of the head of the band of FIG. 1A, in accordance with some embodiments discussed herein;

FIG. 1D illustrates an enhanced perspective view of the head of the band of FIG. 1A, in accordance with some embodiments discussed herein;

FIG. 1E illustrates an enhanced cross-sectional view of the head of the band of FIG. 1D about the line A'-A', in accordance with some embodiments discussed herein;

FIG. 2A illustrates an enhanced top view of another example band, in accordance with some embodiments discussed herein;

FIG. 2B illustrates an enhanced side view of the head of the band of FIG. 2A, in accordance with some embodiments discussed herein;

FIG. 2C illustrates an enhanced perspective view of the head of the band of FIG. 2A, in accordance with some embodiments discussed herein;

FIG. 2D illustrates an enhanced cross-sectional view of the head of the band of FIG. 2C about the line B'-B', in accordance with some embodiments discussed herein;

FIG. 3 illustrates an enhanced cross-sectional view of the head of another example band, in accordance with some embodiments discussed herein;

FIG. 4A illustrates an enhanced top view of another example band, in accordance with some embodiments discussed herein;

FIG. 4B illustrates an enhanced side view of the band of FIG. 4A, in accordance with some embodiments discussed herein;

FIG. 4C illustrates an enhanced perspective view of the band of FIG. 4A, in accordance with some embodiments discussed herein;

FIG. 4D illustrates an enhanced cross-sectional view of the head of the band of FIG. 4B about the line C'-C', in accordance with some embodiments discussed herein;

FIG. 5A illustrates an enhanced side view of another example band, in accordance with some embodiments discussed herein;

FIG. 5B illustrates an enhanced perspective view of the band of FIG. 5A, in accordance with some embodiments discussed herein;

FIG. 6A illustrates a front view of an example fixation plate, in accordance with some embodiments discussed herein;

FIG. 6B illustrates a cross-sectional view of the fixation plate of FIG. 6A about the line D'-D', in accordance with some embodiments discussed herein;

FIG. 6C illustrates a side view of the fixation plate of FIG. 6A, in accordance with some embodiments discussed herein;

FIG. 6D illustrates a perspective view of the fixation plate of FIG. 6A, in accordance with some embodiments discussed herein;

FIG. 6E illustrates a top view of the fixation plate of FIG. 6A, in accordance with some embodiments discussed herein;

FIG. 7A illustrates a front view of another example fixation plate, in accordance with some embodiments discussed herein;

FIG. 7B illustrates a cross-sectional view of the fixation plate of FIG. 7A about the line E'-E', in accordance with some embodiments discussed herein;

FIG. 7C illustrates a perspective view of the fixation plate of FIG. 7A, in accordance with some embodiments discussed herein;

FIG. 7D illustrates a side view of the fixation plate of FIG. 7A, in accordance with some embodiments discussed herein;

FIG. 7E illustrates a side view of an example fixation plate having spikes on its bottom surface, in accordance with some embodiments discussed herein;

FIG. 8A illustrates a front view of another example fixation plate, in accordance with some embodiments discussed herein;

FIG. 8B illustrates a side view of the fixation plate of FIG. 8A, in accordance with some embodiments discussed herein;

FIG. 8C illustrates a cross-sectional view of the fixation plate of FIG. 8A about the line F'-F', in accordance with some embodiments discussed herein;

FIG. 8D illustrates a perspective view of the fixation plate of FIG. 8A, in accordance with some embodiments discussed herein;

FIG. 9A illustrates a front view of another example fixation plate, in accordance with some embodiments discussed herein;

FIG. 9B illustrates a cross-sectional view of the fixation plate of FIG. 9A about the line G'-G', in accordance with some embodiments discussed herein;

FIG. 9C illustrates a side view of the fixation plate of FIG. 9A, in accordance with some embodiments discussed herein;

FIG. 9D illustrates a perspective view of the fixation plate of FIG. 9A, in accordance with some embodiments discussed herein;

FIG. 10A illustrates a top view of an example fixation plate with an example band assembled to the fixation plate, in accordance with some embodiments discussed herein;

FIGS. 10B-10D illustrate cross-sectional views of the fixation plate and band of FIG. 10A about the line H'-H', in accordance with some embodiments discussed herein;

FIG. 10E illustrates a top view of the fixation plate and band of FIG. 10A where the attached band has been rotated, in accordance with some embodiments discussed herein;

FIG. 11A illustrates a perspective view of an example tensioning gun being used to generate tension on an example band, in accordance with some embodiments discussed herein;

FIG. 11B illustrates an enhanced view of the tensioning gun and band of FIG. 11A, in accordance with some embodiments discussed herein;

FIG. 12A illustrates a top view of an example tensioning gun, in accordance with some embodiments discussed herein;

FIG. 12B illustrates a side view of the tensioning gun of FIG. 12A, in accordance with some embodiments discussed herein;

FIG. 13A illustrates a perspective view of an example tensioning gun being used to generate tension on an example band where a sidewall of the tensioning gun is made transparent, in accordance with some embodiments discussed herein;

FIG. 13B illustrates an enhanced view of the tensioning gun of FIG. 13A, in accordance with some embodiments discussed herein;

FIG. 14 illustrates an enhanced cross sectional view of an example tensioning gun being used to generate tension on a band, in accordance with some embodiments discussed herein;

FIG. 15 illustrates an example cutting blade of a trim system for a tensioning gun being used to cut an excess portion of a tail for a band, in accordance with some embodiments discussed herein;

FIG. 16A illustrates a front view of an example fixation plate assembled at a sternum, in accordance with some embodiments discussed herein;

FIG. 16B illustrates a perspective view of the fixation plate of FIG. 16A assembled at the sternum, in accordance with some embodiments discussed herein;

FIG. 17 illustrates a perspective view of an example tensioning gun being used to assist in securing an example fixation plate to a sternum of a person, in accordance with some embodiments discussed herein;

FIG. 18A illustrates a perspective view of an example fixation plate being positioned against a cut sternum, in accordance with some embodiments discussed herein;

FIG. 18B illustrates a perspective view of the fixation plate of FIG. 18A with a band being assembled to the fixation plate, in accordance with some embodiments discussed herein;

FIG. 18C illustrates a perspective view of the fixation plate of FIG. 18A with a tensioning gun being used to tension and cut bands, in accordance with some embodiments discussed herein;

FIG. 19A illustrates a bottom view of an example drainage assembly, in accordance with some embodiments discussed herein;

FIG. 19B illustrates a side view of the drainage assembly of FIG. 19A, in accordance with some embodiments discussed herein;

FIG. 19C illustrates a schematic view of the drainage assembly of FIG. 19A having an internal cavity, in accordance with some embodiments discussed herein;

FIG. 19D illustrates an enhanced view of an example drain body of a drainage assembly having suture holes, in accordance with some embodiments discussed herein;

FIG. 19E illustrates an enhanced view of the drain body of FIG. 19A having a plurality of openings in the surface of the drain body, in accordance with some embodiments discussed herein;

FIG. 19F illustrates a bottom schematic view of another example drainage assembly, in accordance with some embodiments discussed herein;

FIG. 19G illustrates a top schematic view of the drainage assembly of FIG. 19F, in accordance with some embodiments discussed herein;

FIG. 20 illustrates an example method for installing a fixation plate and a drainage assembly to a severed sternum, in accordance with some embodiments discussed herein;

FIG. 21 illustrates an alternative tensioning gun having a switch to alternate between a cutting mode and a tensioning mode, in accordance with some embodiments discussed herein;

FIG. 22 illustrates another alternative tensioning gun, in accordance with some embodiments discussed herein;

FIG. 23 illustrates a bottom view of a fixation plate with holes provided within rails, in accordance with some embodiments discussed herein;

FIG. 24A illustrates a top perspective view of a head of a band that is passively engaged with a fixation plate, in accordance with some embodiments discussed herein;

FIG. 24B illustrates a bottom view of a head of a band that is passively engaged with a fixation plate, in accordance with some embodiments discussed herein;

FIG. 24C illustrates a top perspective view of the head of the band of FIG. 24A, in accordance with some embodiments discussed herein;

FIG. 24D illustrates a bottom perspective view of the head of the band of FIG. 24A, in accordance with some embodiments discussed herein;

FIG. 24E illustrates a bottom view of the fixation plate of FIG. 24A, in accordance with some embodiments discussed herein;

FIG. 25A illustrates a top perspective view of a head of a band that is passively engaged with a fixation plate, in accordance with some embodiments discussed herein;

FIG. 25B illustrates a bottom view of a head of a band that is passively engaged with a window of a fixation plate, in accordance with some embodiments discussed herein;

FIG. 25C illustrates a bottom perspective view of the head of the band, in accordance with some embodiments discussed herein;

FIG. 25D illustrates a top perspective view of the head of the band, in accordance with some embodiments discussed herein;

FIG. 26A illustrates a bottom view of a head of a band that includes a cam shaped bottom lock in an open position relative to a fixation plate, in accordance with some embodiments discussed herein;

FIG. 26B illustrates another bottom view of the head in a closed position relative to the fixation plate, in accordance with some embodiments discussed herein;

FIG. 26C illustrates a bottom perspective view of the head of FIG. 26A, in accordance with some embodiments discussed herein;

FIG. 26D illustrates a bottom view of the head of FIG. 26A, in accordance with some embodiments discussed herein;

FIG. 27 illustrates a top view of a fixation plate with circular windows, in accordance with some embodiments discussed herein; and FIG. 28 illustrates a top view of a fixation plate with square windows, in accordance with some embodiments discussed herein.

DETAILED DESCRIPTION

Example embodiments of the present invention now will be described more fully hereinafter with reference to the accompanying drawings, in which some, but not all embodiments of the invention are shown. Indeed, the invention may be embodied in many different forms and should not be construed as limited to the example embodiments set forth herein; rather, these embodiments are provided so that this disclosure will satisfy applicable legal requirements. Like reference numerals generally refer to like elements throughout. For example, reference numerals 104, 204, 304, etc. may each refer to the head of a band. Additionally, any connections or attachments may be direct or indirect connections or attachments unless specifically noted otherwise.

Various bands may be provided that may be used to form loops that may be compressed around a sternum and tensioning plate. FIG. 1A illustrates a top view of an example band. The band 100 may comprise an elongated strip including a tail 102 and a head 104. The tail 102 may be wrapped around to engage with features on the head 104, which may thereby form the band 100 into a loop. Furthermore, tension may be applied to the tail 102 to tighten the band 100. The band 100 may be wrapped around one or more objects to constrain the movement of the objects. For example, the band 100 may be wrapped around a bone of a person. In some embodiments further described herein, the band 100 may be wrapped around a sternum of a person after surgery where the sternum has previously been cut.

Additional features of the example band 100 may be more readily understood in reference to FIGS. 1B-1E, which illustrate various enhanced views of a head 104 of the band 100. The head 104 may define a top surface 109, at least two sidewalls, a bottom surface, and an internal cavity where the end of the tail 102 may be received. The internal cavity may extend from the entrance 106 to the exit 108. Looking at the cross-sectional view of FIG. 1E, the entrance 106 and exit 108 may be seen. In an embodiment, the entrance 106 may be located on the top surface 109 of the band 100. In an embodiment, the exit 108 may be located on the top surface 109 of the band 100. In an embodiment, the entrance 106 and the exit 108 are each located on the top surface 109 of the band 100 such that the tail 102 enters and exits the head 104 via the top surface 109. A locking bar 110 which extends from one sidewall of the head 104 to the other sidewall of the head 104, adjacent the top surface 109, may separate the entrance 106 from the exit 108.

The end of the tail 102 may be inserted through the entrance 106, extended into the space between the pawl 112 and the locking bar 110, and extended through the exit 108 (referred to herein as the insertion direction). As the end of the tail 102 extends toward the exit 108, the pawl 112 may direct the tail 102 toward an exit ramp 118. A portion of the tail 102 may contact the exit ramp 118. The exit ramp 118 may be provided as a trough having a thirty degree angle in some embodiments, but other angles may be used for the exit ramp 118. The exit ramp 118 may be linearly sloped in some embodiments, but the exit ramp may have a curved slope in other embodiments. In either case, the exit ramp 118 may be configured to urge the end of the tail 102 toward the top surface 109, and thus the exit 108, of the head 104. After the end of the tail 102 has been inserted through the internal cavity and slides over the exit ramp 118 and out of the exit 108, tension may be applied to the tail 102 to further tighten the tail 102. Said alternatively, the end of the tail 102 may be pulled while maintaining the head 104 in a relatively stationary position to apply such tension.

Ridges 112A may be provided on the pawl 112, and these ridges 112A of the pawl 112 may engage with ridges 202A (see FIG. 2A) on the top surface 109 of the tail 102 in some embodiments. The engagement of the ridges may generally prevent the band 100 from being untightened or from moving in the direction opposite the insertion direction. To disengage the band 100, an operator may simply cut the band 100, making the band 100 easily removable if necessary.

The head 104 of the band 100 may include a top portion 114 and a bottom lock 120. A gap 119 may be defined between the top portion 114 and the bottom lock 120. As described further herein, the gap 119 between the top portion 114 and the bottom lock 120 may be used to receive a portion of a fixation plate 1022 to restrain the movement of the band 100 relative to the fixation plate 1022 (see FIG. 10B).

Furthermore, in some embodiments, the head 104 may include pockets 116. The illustrated embodiment includes two pockets 116, but any number of pockets may be used. The pockets 116 may be configured to assist in generating tension between the tail 102 and the head 104 of the band 100, as will be more fully explained herein.

In some embodiments, the bands 100 may be pre-bent or curved at a pre-determined radius. This may help facilitate maneuverability of the bands 100 through and under the intercostal spaces and under the posterior surface of the sternum.

FIGS. 2A-2D illustrate various enhanced views of a head of another band. Looking at FIG. 2A, a tail 202 having ridges 202A is illustrated on the left, and the head 204 of the band is illustrated on the right. As noted above, the end of the tail 202 may be wrapped around and inserted into an internal cavity extending from the entrance 206 to the exit 208 within the head 204. Looking at FIG. 2D, the end of the tail 202 may be inserted through the entrance 206, extend underneath the locking bar 210, and extend out through the exit 208. The locking bar may include ridges similar to the ridges 112A illustrated on the pawl 112 of FIG. 1E. As illustrated in FIG. 2A, as the end of the tail 202 extends out through the exit 208, the tail 202 may rest on the exit ramp 218.

Additionally, the head 204 of the band may include a top portion 214 and a bottom lock 220. A gap may be defined between the top portion 214 and the bottom lock 220. As described further herein, the gap between the top portion 214 and the bottom lock 220 may be used to restrain the movement of the head 204 of the band relative to a fixation plate 1022 (see FIG. 10B). The head 204 may be different from the head 104 of FIGS. 1A-1E in that only a single locking bar 210 is provided without a separate pawl. Furthermore, the overall shape of the head 204 may be more rounded than the head 104. Additionally, the head 204 is provided without any pockets 116 (see FIG. 1D). Additionally, the bottom lock 220 may be tapered to increase the ease of installing the head 204 in a window of a fixation plate 1022 (see FIG. 10B).

FIG. 3 illustrates an enhanced cross-sectional view of the head 304 of another example band. FIG. 3 also permits the tail 302 of the band to be seen. The end of the tail 302 may be wrapped around and inserted into an internal cavity extending from the entrance 306 to the exit 308 within the head 304. Looking at FIG. 3, the end of the tail 302 may be inserted through the entrance 306, extend underneath the locking bar 310 but above the pawl 312, and extend out through the exit 308. The pawl 312 may include ridges 312A similar to the ridges 112A illustrated on the pawl 112 of FIG. 1E. Where this is the case, ridges may be provided on the bottom surface of the tail 302 so that the ridges of the tail 302 may engage with the ridges 312A of the pawl 312.

Additionally, the head 304 of the band may include a top portion 314 and a bottom lock 320. A gap may be defined between the top portion 314 and the bottom lock 320. As described further herein, the gap between the top portion 314 and the bottom lock 320 may be used to restrain the movement of the head 304 of the band relative to a fixation plate 1022 (see FIG. 10B). In the head 304 of FIG. 3, the top portion 314 may be enlarged on both the entry side (on the right) and on the exit side (on the left) relative to the head 104 of FIGS. 1A-1E so that the top portion may have a larger interface surface with a fixation plate 1022 (see FIG. 10A).

FIGS. 4A-4D illustrate various enhanced views of a head 404 of another band. FIG. 4A also permits the tail 402 of the band and ridges 402A on the tail 402 to be seen. The end of the tail 402 may be wrapped around and inserted into an internal cavity extending from the entrance 406 to the exit 408 within the head 404. Looking at FIG. 4D, the end of the tail 402 may be inserted through the entrance 406, extend underneath the pawl 412, and extend out through the exit 408. The pawl 412 may include ridges 412A similar to the ridges 112A illustrated on the pawl 112 of FIG. 1E. Similar to other embodiments, the head 404 may include a top portion 414 and a bottom lock 420 that may create a gap configured to restrain the movement of the head 404 of the band relative to a fixation plate 1022 (see FIG. 10B). The exit ramp 418 (see FIG. 4C) for the head 404 is also curved, unlike the exit ramp 118 of FIG. 1D.

FIGS. 5A-5B illustrate various enhanced views of another example band. The end of the tail 502 may be wrapped around and inserted into an internal cavity extending from the entrance 506 to the exit 508 within the head 504. Looking at FIG. 5B, the end of the tail 502 may be inserted through the entrance 506, extend under the locking bar and above a pawl, and extend out through the exit 508. The pawl may include ridges similar to the ridges 112A illustrated on the pawl 112 of FIG. 1E. Similar to other embodiments, the head 504 may include a top portion 514 and a bottom lock 520 that may create a gap configured to restrain the movement of the head 504 of the band relative to a fixation plate 1022 (see FIG. 10B).

The head 504 may also include one or more pockets 516. In the illustrated embodiment, two pockets 516 are illustrated. The pockets 516 may provide a location where alignment features 1150 (see FIG. 11B) of a tensioning gun 1138 (see FIG. 11A) may be received. The pockets 516 may provide leverage for the tensioning gun 1138 as the tensioning gun 1138 applies tension to a head 504.

Various fixation plates are also contemplated that may be used to assist in securing two severed halves of a severed sternum together. Fixation plates may comprise materials and possess features that permit the fixation plates to conform to the shape of the underlying bone. Furthermore, the fixation plates may disperse any stress generated by bands across a greater surface area on the underlying bone to prevent stress concentrations at specific locations where the bands are provided. FIG. 6A-6E illustrate various views of an example fixation plate 622. The fixation plate 622 may generally comprise an elongated body, similar in length and width to a portion of the human sternum. The fixation plate 622 may include at least two rails 626 that extend lengthwise. In an embodiment, the rails 626 may be connected to one another via crossbars 628. In another embodiment, the fixation plate 622 may comprise two rails 626 and two crossbars 628 (one at each end-see FIG. 7A). In an embodiment, the fixation plate 622 may comprise two rails 626 and three crossbars 628. In another embodiment, the fixation plate 622 may comprise two rails 626 and five crossbars 628. Any number of rails 626 and crossbars 628 are contemplated herein. The rails 626 and crossbars 628 may form one or more windows 624 (i.e. open cavities). The windows 624 may be configured to receive the head 104 of a band 100 (see FIG. 1A). Three windows 624 are illustrated in FIG. 6A, but any number of windows 624 may be included. In one embodiment, the fixation plate 622 might resemble a ladder, consisting of parallel longitudinal rails 626 joined by multiple crossbars 628 occurring at various points along the long axis of the fixation plate 622, creating windows 624 within the central region of the fixation plate 622. In an embodiment, the fixation plate 622 may extend the entire length of the forward-facing aspect of the sternal anatomy from the manubrium to the xiphoid process, but the fixation plate 622 may be configured to extend only a portion of this length in other embodiments.

In some embodiments, the windows 624 are ovular or elliptical in shape. In other embodiments, the windows 624 are square or rectangular in shape. Any shape known in the art may be utilized herein. In some embodiments, the windows 624 may be positioned and sized differently from one another. That is, in the lengthwise direction, the fixation plate 622 may not be symmetrical. The fixation plate 622 may comprise two longer windows 624 on one lengthwise side of the contoured section 630 (explained below), one window 624 of moderate length on the other lengthwise side of the contoured section 630, and one shorter window 624 within the contoured section 630, in an embodiment. Likewise, the widths of the various windows 624 may vary. One or more windows 624 may have a first width while one or more other windows 624 may have a second width.

As can be seen in FIG. 6B, the rails 626 may include a protruding portion 626A that extends partially into a window 624. This protruding portion 626A may extend into the gap 119 (see FIG. 1E) formed between the top portion 114 and the bottom lock 120 of the head 104 of a band 100 (see FIG. 1E). When the protruding portion 626A extends into this gap 119 (see FIG. 1E), the engagement between the protruding portion 626A and the head 104 of the band 100 (see FIG. 1E) may restrict the movement of the head 104—the head 104 may be permitted to slide along the length of the window (i.e. along the rails, left and right in FIG. 6A), but the engagement may prevent the head 104 from moving perpendicular to the window (i.e. toward the rails, up and down in FIG. 6A). The engagement between the protruding portion 626A and the head 104 may keep the head 104 retained in the window 624, but, upon the application of sufficient force, one may remove the head 104 from the window 624 if desired. Alternatively, the bottom lock 120 of the head 104 of the band 100 may be keyed to passively insert through the window 624 when the head 104 is partially rotated (e.g. by rotating the bottom lock 120 by 90 degrees), and the bottom lock 120 may then become locked underneath the rails 626 by partially rotating the bottom lock 120 (e.g. by rotating the bottom lock 120 in a reverse direction by 90 degrees). The bottom lock 120 may be a twist lock in some embodiments. Where the fixation plate 622 is used with a sternum, the rails 626 of the fixation plate 622 may have a height (H) that is less than 5 mm in some embodiments. This reduced height (H) may make the fixation plate 622 have a lower profile, with the bands wrapped closer to the bone. This may reduce the amount that the band needs to change in direction, and this may increase the amount of surface area on the bone that the band comes into contact with. However, other larger or smaller sized fixation plates 622 may be used at the sternum. Furthermore, where the fixation plate 622 is used with a larger bone such as femur, the fixation plate 622 may have height that is 20 millimeters or greater.

The fixation plate 622 may also include one or more reinforced areas. In the illustrated embodiment, three reinforced areas are provided, with each of these reinforced areas being at the crossbars 628. As illustrated in the side view of FIG. 6C, the reinforced areas may have increased thickness and/or strength compared to other portions of the fixation plate 622. In some cases, the reinforced areas may also assist in providing an end point to the windows 624 to restrict the movement of a head 104 of a band 100. The reinforced areas that may provide strength and reinforcement and may disperse the structural load acting on the fixation plate 622 across the fixation plate 622 to minimize stress points.

In some embodiments, the reinforced areas may be provided at the crossbars 628 to provide rigidity against bending in the horizontal direction (up and down from the perspective in FIG. 6A) while permitting bending of the fixation plate 622 in the vertical direction (lengthwise, left and right from the perspective in FIG. 6A). By doing so, the fixation plate 622 may be free to bend in the vertical direction to conform to the shape of a sternum and may allow the patient to retail natural movement of the sternum. However, the reinforced areas may have limited rigidity against bending in the horizontal direction in other embodiments so that the fixation plate 622 may also be free to easily bend in the horizontal direction to conform to the shape of a sternum.

As illustrated in FIGS. 6A, 6C, and 6D, the fixation plate 622 may include a contoured section 630. The contoured section 630 may be provided so that the fixation plate 622 may more easily conform to the shape of the underlying sternum. In an embodiment, the bottom surface 632 of the fixation plate 622 may generally be linear, but the contoured section 630 may bow inwardly, in a curved or angular manner, toward a top surface 621 of the fixation plate 622. For example, the contoured section 630 may be configured to be placed over the sternal manubrial junction or the angle of Louis on the sternum in some embodiments. Additionally, a contoured section 630 may be placed over the sternal body xiphoid junction. In some embodiments, the fixation plate 622 may have areas of increased flexibility to allow it to better conform to the specific anatomy of a given patient at certain areas (e.g. the sternal manubrial junction, the sternal body xiphoid junction, etc.).

The bottom surface 632 of the fixation plate 622 may also include one or more spikes 732A (see FIG. 7E) to assist in gaining traction between the fixation plate 622 and the severed sternum (see FIG. 7E). However, the bottom surface 632 may be free from any spikes in some embodiments. One or more cavities 634 may be provided in some embodiments at the bottom surface 632 of the fixation plate 622. The windows 624 and the cavities 634 may provide an open architecture to allow for bodily fluids to flow through to permit proper healing in a cut 1857 in the severed sternum 1856 (see FIG. 18A). The radius R at the end of the windows 624 may have a large size to ensure that the head 104 of a band 100 may slide the maximum distance of the window 624. The fixation plate 622 may provide sufficient stiffness and rigidity to buttress an injured bone (e.g. the sternum) while providing sufficient ductility to conform to the shape and contours of the underlying bone.

Another alternative fixation plate 722 is also illustrated in FIGS. 7A-7E. Similar to the fixation plate 622 of FIGS. 6A-6E, the fixation plate 722 may include a window 724. The fixation plate 722 may include rails 726 that assist in forming the window 724. The window 724 may be configured to receive the head 104 of a band 100 (see FIG. 1A). As can be seen in FIG. 7B, the rails 726 may include a protruding portion 726A that extends into the window 724. This protruding portion 726A may extend into the gap 119 (see FIG. 1E) formed between the top portion 114 and the bottom lock 120 of the head 104 of a band 100 (see FIG. 1E) to restrict the movement of the head 104. The protruding portion 726A may operate similar to the protruding portion 626A of FIG. 6B.

As illustrated in FIG. 7D, the fixation plate 722 has a bottom surface 732, and this bottom surface 732 is flat in the fixation plate 722 of FIG. 7D. However, in other embodiments, the bottom surface 732 may have a concave shape, a convex shape, or some other non-flat shape. For example, the bottom surface 732 may be slightly concave so that the fixation plate 722 may follow the natural anatomic radius of the sternum. Furthermore, as illustrated in FIG. 7D, the fixation plate 722 may have spikes 732A on the bottom surface 732 in some embodiments. The spikes 732A may have sharp tips or dull tips in some embodiments, and the spikes 732A may be configured to engage bone at the sternum to minimize any noticeable pain for the patient. A single spike may be provided in some embodiments, or a plurality of smaller spikes may be used. Furthermore, the spikes 732A may possess a wide variety of shapes. In the illustrated embodiment, the spikes 732A have a rectangular pyramid shape. However, the spikes may be cone shaped, in another pyramid shape, in the shape of a triangular prism, asymmetrically shaped, etc. Likewise, in place of spikes 732A, the plate may be textured with bunt pegs or some other feature to permit improved traction on the bottom surface 732.

FIG. 8A-8D illustrate various views of another example fixation plate 822. The fixation plate 822 may include rails 826 that assist in forming windows 824. This fixation plate 822 may also have protruding portions 826A, crossbars 828 having reinforced areas, and a bottom surface 832 that may operate in generally the same manner as similar features described above. The fixation plate 822 may have a flatter shape than the fixation plate 622 of FIG. 6A as the fixation plate 822 may be provided without any contoured section 630.

FIG. 9A-9D illustrate various views of another example fixation plate 922. The fixation plate 922 may include rails 926 that assist in forming windows 924. This fixation plate 922 may also have protruding portions 926A, crossbars 928 having reinforced areas, and a bottom surface 932 that may operate in generally the same manner as similar features described above. Like the fixation plate 622 of FIG. 6C, the fixation plate 922 may include a contoured section 930 to permit the fixation plate 922 to accommodate the shape of certain features on the sternum. However, certain features on the fixation plate 922 may have a different shape and/or size than the fixation plate 622. For example, the contoured section 930 possesses a different shape than the contoured section 630 of the fixation plate 622. Additionally, the reinforced areas may have narrower width than the reinforced areas of the fixation plate 622 of FIG. 6D. Furthermore, the fixation plate 922 may have a low profile with the height of the rails 926 (see FIG. 9B) being smaller than rails of most other embodiments, and this smaller height may allow a band installed in the fixation plate 922 to be provided closer to the bone and reduce any change in direction for an installed band. The height of the rails 926 may be the same as the height (H) of the rails 626 in FIG. 6B.

The fixation plate 922 may contain nodes in some embodiments. These nodes may be large enough to span the sternum of the patient, and the nodes may contain a feature that may accept the head or tail of an independent fasteners such as but not limited to bands, screws, or cable ties. Furthermore, in some alternative embodiments, the fixation plate may have bands integrated into the fixation plate itself so that the installer will not be required to attach the bands to the fixation plate.

A fixation plate may be selected that may best conform to the size and shape of the sternum of a given patient, and the provision of fixation plates having different sizes and shapes may be beneficial to accommodate this. After a fixation plate has been selected, the head of a band may be removably attached to the fixation plate within a window in the fixation plate. FIG. 10A illustrates a top view of an example fixation plate 1022 with an example band 1000 assembled to the fixation plate 1022. As can be appreciated, the bottom lock 1020 of the head 1004 may be inserted into the window 1024. Due to the engagement between the head 1004 and the window 1024, the head 1004 may be permitted to shift along the track formed by the window 1024. For example, in the embodiment illustrated in 10A, the head 1004 may move up and down along the track formed by the window 1024. Furthermore, in the embodiment illustrated in 10A, the engagement of the head 1004 may prevent the head 1004 (1) from moving to the left or the right; (2) from moving into or out of the page (unless sufficient force is provided to remove the head 1004 from the window 1024). The head 1004 may be shaped in a manner that permits the head 1004 to rotate as it is retained in the window 1024. For example, in the illustrated embodiment of FIG. 10E, the head 1004 is rotated at an angle, and this may be beneficial to form an X-pattern, to fit to the anatomy of the patient, to apply forces to the sternum in other directions, etc. Where multiple bands 1000 are installed in the window 1024, the bands 1000 may be permitted to slide and pivot independently of each other in some embodiments. Furthermore, FIGS. 10B-10D illustrate a cross-sectional view of the fixation plate 1022 and band 1000 of FIG. 10A about the line H'-H'.

Looking at FIG. 10B, various features of the fixation plate 1022 and the band 1000 may be seen. The band 1000 may include a head 1004 and a tail 1002. Similar to the embodiments of fixation plates discussed above, the fixation plate 1022 may include rails 1026 that assist in forming windows 1024. The fixation plate 1022 may also include a protruding portion 1026A that extends into a window 1024.

This protruding portion 1026A may extend into a gap formed between the top portion 1014 and the bottom lock 1020 of the head 1004 of a band. When the protruding portion 1026A extends into this gap, the engagement between the protruding portion 1026A and the head 1004 of the band 1000 may have restrict the movement of the head 1004—the head 1004 may be permitted to slide along the window 1024 (left and right in FIG. 6A), but the engagement may prevent the head 1004 from moving perpendicular to the window 1024 (up and down in FIG. 6A). The engagement between the protruding portion 1026A and the head 1004 may keep the head 1004 retained in the window 1024, but, upon the application of sufficient force, one may remove the head 1004 from the window 1024 if desired. The head 1004 may be snapped in with or without aid on an external tool with forced pressure in some embodiments. The bottom lock 1020 of the head 1004 may be made of elastic material in some embodiments to permit the bottom lock 1020 to deform a sufficient amount so that the bottom lock 1020 may extend under the windows 1024. The head 1004 may be attached to the fixation plate 1022 within the window 1024 at a location proximate to an intercostal space 1660 (see FIG. 16A) or the head 1004 may be attached and then slid to an appropriate location.

In some embodiments, the bottom lock of the head may have a circular shape, and the width of the bottom lock may be a diameter of the bottom lock in that case. Examples of such a circularly shaped bottom lock are illustrated in FIGS. 2A, 4A, and 5A. However, in other embodiments, the bottom lock may possess other shapes. Where a circularly shaped bottom lock is utilized, the width of the bottom lock may be greater than the width of the window 1024 (e.g. the width runs left and right in FIG. 10A). Where this is the case, the head 1004 may be attached to the fixation plate 1022 between the rails 1026 within a window 1024 by applying a force on the head 1004 to urge the bottom lock towards the rails 1026, and the bottom lock may be configured to bend elastically upon application of the force to permit the bottom lock to extend through the window 1024.

In other embodiments, the bottom lock may have a non-circular shape (e.g. oval shaped, rectangularly shaped, etc.), and the bottom lock may define a minimum width and a maximum width. An example of this is illustrated in the bottom lock 120 of FIGS. 1A-1E. The bottom lock 120 may have a maximum width (W1) as illustrated in FIG. 1C, and the bottom lock 120 may have a minimum width (W2) as illustrated in FIG. 1D. The minimum width (W2) of the bottom lock 120 may be less than the width of the window 1024, and the maximum width (W2) of the bottom lock 120 may be greater than the width of the window 1024. Where this is the case, the head 1004 may be attached to the fixation plate 1022 by rotating the head 1004 so that the bottom lock 120 may fit through the window 1024 (i.e. so that the width of the bottom lock 120 becomes less than the width of the window 1024). Once the bottom lock 120 has been received in the window 1024, the head 1004 may be rotated again so that the bottom lock 120 may be retained within the window 1024. Once rotated, the width of the bottom lock 120 may be greater than the width of the window 1024. Other bottom locks 120 are also contemplated. For example, the bottom lock 120 may have a portion that is expandable and retractable, allowing the bottom lock 120 to be retracted so that it may be inserted into a window 1024 and allowing the bottom lock 120 to be expanded so that it may be retained in the window 1024.

Looking now at FIG. 10D, the tail 1002 may be looped around into the internal cavity extending from the entrance 1006 to the exit 1008, extending along the path of the arrows illustrated in FIG. 10D (the insertion direction). The end of the tail 1002 may be inserted through the entrance 1006, above the pawl 1012 and below the locking bar 1010, through a binding area 1036, and out of the exit 1008. The tail 1002 may be retained at the binding area 1036 as the pawl 1012 and the locking bar 1010 may be urged against the tail 1002. A buckling action may be created at the binding area 1036, and this may permit further portions of the tail 1002 to be inserted through the internal cavity (e.g. along the path of the arrows) without permitting reverse movement of the tail 1002 in the opposite direction.

While the fixation plate 1022 is effectively affixed to bone using bands 1000 in the illustrated embodiment, the fixation plate 1022 may also be affixed to bone with cerclage wire or other cabling techniques whereby cerclage wire or cable passes over and around the fixation plate 1022 as the fixation plate 1022 rests on the bone. Where this is done, the fixation plates may include slots that may be configured to receive wire or other cables. The fixation plate 1022 and one or more bands 1000 may be attached together before being inserted into the body of the patient in some embodiments, but the bands 1000 may simply be attached to the fixation plate 1022 once the fixation plate 1022 has been inserted into the body of the patient in other embodiments.

While the bands may be manually installed, tensioned, and then cut, it may be detrimental to perform these tasks manually for several reasons. First, manual performance of these tasks can lead to human error. The fixation plate may not be installed properly or the bands may not be tightened to an appropriate tension, and this may cause the patient to heal improperly. Second, manual performance of the tasks will be less user-friendly. Where the fixation plate is being installed at a severed sternum, one or more installers would need to maintain the two severed sternum halves in an appropriate position, they would need to maintain the fixation plate at the appropriate position, and they would need to install bands to retain the fixation plate in the appropriate position. This may be difficult to do at the same time, increasing frustration for the installers and leading to an increased risk of error during installation. Third, manual performance of the tasks may very time consuming for installer(s).

Tensioning guns are contemplated that may be used to apply tension to bands until a desired tension level is reached. Once the desired tension level is reached, the tensioning gun may cut the band. The tensioning gun may reduce human error by maintaining a consistent amount of tension in each band. Manual tensioning places undue reliance on user judgment based on prior experience, visualization or tactile feel, and approximations or guesswork from the installer may lead to errors. The tensioning gun may be easier for installers to operate eliminating any approximations or guesswork from the installer as to whether the tension level is appropriate. By cutting the bands automatically after the desired tension is obtained, this alleviates the need for the installer to perform this task separately. The tensioning gun may also tighten the bands up more quickly than manual tightening of bands.

FIG. 11A illustrates a perspective view of an example tensioning gun 1138 being used to generate tension on an example band 1100, and FIG. 11B illustrates an enhanced view of the tensioning gun 1138 and band 1100 of FIG. 11A.

Looking first at FIG. 11A, various features of the tensioning gun 1138 may be seen. The tensioning gun 1138 may tension the bands 1100 to precise levels. The tensioning gun 1138 may include a handle 1140 and a actuator lever 1142. One may hold the handle 1140 as he or she is using the tensioning gun 1138. Further, the actuator lever 1142 may be compressed when the user desires to provide tension to the band 1100. In some embodiments, upon the desired tension being reached, the tensioning gun 1138 may cease providing further tension, and the properties of the band may maintain this tension. For example, the band, the pawl, and the locking bar and any ridges thereon may generally maintain the tension at this level, but other locking mechanisms may be used to prevent the tension on the band 1100 from being released. The trim system 1148 may automatically be actuated so that the band 1100 may be cut. However, in other embodiments, a separate button may be provided that may be pressed when the user desires to actuate the trim system 1148, and the user may press this separate button once the desired tension is obtained. The actuator lever 1142 may be provided with a high mechanical advantage ratio so that it may be used more easily.

Additionally, the tensioning gun 1138 may include a barrel 1141 with one or more features provided therein. The barrel 1141 may contain an internal chamber that generally runs along the length of the barrel 1141. The barrel 1141 may include a trim system 1148 disposed proximate to the end of the barrel 1141. Furthermore, a safety lock 1144 is provided on the barrel 1141. The safety lock 1144 may be provided in the form of a switch, a lever, etc., and the safety lock 1144 may prevent premature or unintended cutting of bands 1100. The safety lock 1144 may be in a locked state to prohibit tension from being applied via the tensioning gun 1138 and/or to prevent the trim system 1148 from cutting the bands 1100. Furthermore, the safety lock 1144 may be in an unlocked state to permit tension to be applied via the tensioning gun 1138 and/or to permit the trim system 1148 to cut the bands. While the safety lock 1144 is provided on the barrel 1141 in FIG. 11A, the safety lock 1144 may be provided at another location in other embodiments. The safety lock 1144 may be provided on the left side, the right side, on both sides, on the rear, etc. of the tensioning gun 1138. In other embodiments, a secondary switch, lever, etc. may be added to the tensioning gun 1138 to actuate cutting.

Furthermore, a tension limit system 1252 (see FIG. 12A) may be provided. This tension limit system 1252 may be provided in the barrel 1141 in some embodiments, but the tension limit system 1252 may be provided at other locations. A knob 1146 may be provided to permit the desired tension level to be adjusted by a user. A top view showing a similar knob 1246 is also provided in FIG. 12A. Adjustment of the knob 1146 or the knob 1246 may cause a corresponding adjustment to be made at the tension limit system 1252, preventing tension from being applied past a maximum level. While a knob 1246 may be used as illustrated, other clutch mechanisms may be used in other embodiments to limit the amount of tension that may be applied to the bands.

In some embodiments, the tension limit system 1252 may include a spring-loaded probe. The spring-loaded probe may extend proximate to the end of the barrel 1141, and the spring-loaded probe may extend proximate to the trim system 1148 (see FIG. 11A). The spring-loaded probe may require depression of the probe into a corresponding barrel cavity before the trim system 1148 may cut any band. This tension limit system 1252 may prevent premature or unintentional band cutting. The tension limit system 1252 may also allow cutting only when the tip of the barrel 1141 and the cutting blade 1554 (see FIG. 15) are seated at the lowest and most optimal position to ensure a flush cut of the band.

Looking now at FIG. 11B, the engagement between the tensioning gun 1138 and the head 1104 of a band 1100 may be seen. The tensioning gun 1138 may include two alignment features 1150 extending from the barrel 1141, but any number of alignment features 1150 may be used. A channel 1151 may be provided between the two alignment features 1150 where the tail of the band 1100 may be received and positioned within the barrel 1141 of the tensioning gun 1138. The channel 1151 may correspond to the cross-sectional shape of the band 1100 so that the free end of the tail for the band 1100 may be precisely fed into the channel 1151 in a controlled manner. The tensioning gun 1138 may receive the excess portion of the band 1100 without unduly altering the angle of the band 1100—by doing this, the amount of stress and strain acting on the band 1100 and tensioning gun 1138 may be reduced, and the amount of tension that must be applied by the tensioning gun 1138 may be reduced.

The head 1104 may have pockets 116 (see FIG. 1D) that are configured to receive the alignment features 1150. As the tensioning gun 1138 is applying tension, the alignment features 1150 may be urged against a wall in a pocket 116 to provide leverage. The alignment features 1150 may ensure that the tensioning gun 1138 is appropriately positioned relative to the bands 1100. This positioning may help ensure that that the head 1104 of the band 1100 is maintained in a stationary position as tension is applied. By ensuring this proper positioning, the tension level in installed bands 1100 may be consistent, and errors may be avoided. By applying tension to the bands 1100 (e.g., by pulling the tail of the band 1100 into the tensioning gun 1138 via actuation of the actuator lever 1142 while maintaining the head 1104 of the band 1100 in a stationary position), the bands 1100 may tighten around the fixation plate 1022 (see FIG. 10A) and bone and cause the fixation plate 1022 to conform to the shape of the underlying sternum.

Upon continuous actuation of the actuator lever 1142, the band 1100 may advance through the channel 1151. As more portions of the band 1100 have advanced into the channel 1151, more tension may be applied to the bands 1100 to oppose further advancement of the bands 1100 in the insertion direction. This increased tension may occur due to the engagement between the notches 112A in the head 104 and notches 102A of the tail 102 (see, e.g., FIG. 1E). This increased tension may also occur based on other forces acting on other portions of the loop formed by the tail 102 as the loop extends around the bone and the fixation plate.

The tensioning gun 1138 may be removed quickly and easily, and the tensioning gun 1138 may only grip a band 1100 when the actuator lever 1142 is being actuated. To the extent an installer wishes to apply further tensioning after using the tensioning gun 1138 once, the tensioning gun 1138 may be subsequently reintroduced over the exposed free tail end of a band 1100.

In some embodiments, the tensioning gun 1138 may contain other features such as a battery operated light source such as LED or a fiber optic light source. Additionally, the tensioning gun 1138 might contain suctioning and/or irrigating capability or have a mount or fitting where such capabilities may be attached to the device. Where this is the case, batteries may be provided in the tensioning gun 1138, or some other power source may be included in the tensioning gun 1138. While various features of the tensioning gun 1138 are mechanically actuated in the illustrated embodiment of FIGS. 11A and 11B, the tensioning gun 1138 may include electronic circuitry in some embodiments to set the tension limit, to determine the applied tension, to actuate the trim system, etc. In some embodiments, the tensioning gun 1138 may include a memory to store computer readable instructions, and the tensioning gun 1138 may also include a user interface to permit user inputs.

Other view of an example tensioning gun are also provided in FIGS. 12A-12B. FIG. 12A illustrates a top view of an example tensioning gun 1238, and FIG. 12B illustrates a side view of the tensioning gun 1238 of FIG. 12A. Similar to the tensioning gun 1138, the tensioning gun 1238 may have a handle 1240, a actuator lever 1242, a safety lock 1244, alignment features 1250, a channel 1251, and a tension limit system 1252. FIG. 12A illustrates a top view of the tensioning gun 1238, permitting the tension limit system 1252 to be seen. In some embodiments, no top surface is provided for the tensioning gun 1238. This may be beneficial to permit cut portions of a band to be easily removed from the tensioning gun 1238. Cut portions of a band may be easily removed from the tensioning gun 1238 upon deactivation or release of the actuator lever 1142. However, a top surface may be provided in other embodiments to contain the features of the tensioning gun 1238 (e.g. the tension limit system 1252).

Further features of an example tensioning gun are provided in FIGS. 13A-13B. FIG. 13A illustrates a perspective view of an example tensioning gun 1338 being used to generate tension on an example band 1300 where a sidewall of the tensioning gun 1338 is made transparent, and FIG. 13B illustrates an enhanced view of the tensioning gun 1338 of FIG. 13A. Looking at FIG. 13B, the tail of the band 1300 may be looped around and then the free end of the tail may be inserted through the channel 1251 (see FIG. 12A) formed in the tensioning gun 1338 between the alignment features 1250 (see FIG. 12A). Excess portions of the tail may extend through the channel 1251. Once cut, one may remove the excess portions of the tail through an open top surface.

FIG. 13B permits portions of a trim system 1348 provided in the tensioning gun 1338 to be seen. The trim system 1348 may be provided with a cutting blade 1354, and the trim system 1348 may be configured to receive an indication of whether or not the tension limit has been reached at the tension limit system 1252 (see FIG. 12A). Upon the tension limit being reached, the trim system 1348 may be activated automatically so that the cutting blade 1354 may cut the excess portions of a tail. The cutting blade 1354 may cut the tail so that no jagged edges remain. The trim system 1348 may be located proximate to the end of the barrel 1141. Placement of the trim system 1348 at this location may assist in ensuring a flush cut of the band so no portion of the remaining band may irritate overlying tissues and/or be palpated by the patient and potentially cause discomfort.

The tensioning gun 1338 may apply tension to a band 1300 prior to and at the time of cutting using a cam mechanism 1355 housed within the tensioning gun 1338. This cam mechanism 1355 may be part of the tension limit system 1252 (see FIG. 12B) in some embodiments. The cutting blade 1354 may be activated while the band 1300 is under tension, and this may permit the cut to be performed with less force than if the band 1300 in not tensioned. Another consequence of a band 1300 being cut while under tension is that the band 1300 recoils slightly after cutting. This may cause retraction of the tail 102 (see FIG. 1E) of the band 1300 protruding though the internal cavity of the head 104 (see FIG. 1E). This retraction may keep the cut end of the band 1300 flush to or beneath the top surface of a head 104 (see FIG. 1E).

The tensioning gun may apply tension to a band to tighten loops formed by the band. FIG. 14 illustrates an enhanced, cross sectional view of an example tensioning gun being used to generate tension on a band 1400. As illustrated, the tail 1402 of the band 1400 may proceed in a manner similar to that shown in FIG. 10D. The tail 1402 may be inserted through the entrance 1006 (see FIG. 10D), through a binding area 1036 (see FIG. 10D) where the tail 1402 may be constrained between a pawl 1012 (see FIG. 10D) and a locking bar 1010 (see FIG. 10D), and out of the exit 1008 (see FIG. 10D). Once the end of the tail 1402 has been inserted in this manner, the tail 1402 may be provisionally tensioned further and/or the end of the tail 1402 may be inserted into the tensioning gun for further tensioning. The alignment features 1450 operate similarly to other alignment features discussed herein to assist in engaging the head of the band 1400.

FIG. 15 illustrates a schematic view of an example cutting blade 1554 of a trim system for a tensioning gun being used to cut an excess portion of a tail 1502 for a band. The trim system may be provided with a cutting blade 1554, and the trim system may be configured to receive an indication of whether or not the tension limit has been reached at the tension limit system 1252 (see FIG. 12A). Upon receiving an indication that the tension limit has been reached, the trim system may be configured to cause the cutting blade 1554 to be activated to cut the excess portion of the tail 1502. The trim system and the cutting blade 1554 may be configured to cut the tail 1502 to avoid the creation of any jagged edges at the cut end. Jagged edges may cause pain and/or discomfort for a patient. A band 1500 may be fed through the channel 1151 (see FIG. 11B) so that a perpendicular relationship may be maintained between the band 1500 and the cutting blade 1554 to ensure a clean and straight cut with no jagged edges. The cutting blade 1554 may be slightly curved or radially shaped to avoid any sharp edge on the end of the tail 1502 from extending through the exit 108 (see FIG. 1E) of the head 104 of a band to prevent soft tissue irritation.

Once assembled, the fixation plate may be positioned at the sternum above a cut on the sternum, and bands may be looped around to urge severed halves of the sternum together. FIG. 16A illustrates a front view of an example fixation plate 1622 assembled at a sternum 1656, and FIG. 16B illustrates a perspective view of the fixation plate 1622 of FIG. 16A assembled at the sternum 1622. As illustrated, the fixation plate 1622 may be positioned adjacent to the sternum 1656, and bands 1600 may be wrapped around the sternum 1656 and secured in a loop. A band 1600 may proceed through the intercostal spaces 1660 formed between two ribs 1658 on one side of the sternum 1656. After that, the band 1600 may be wrapped around the rear of the sternum 1656 so that the band 1600 may proceed through an intercostal space 1660 on the opposite side of the sternum 1656. The band 1600 may then be inserted into the internal cavity in head of the band 1600 so that a loop may be formed. Alternatively, instead of wrapping the bands 1600 around the sternum 1656, a pilot hole may be created in the sternum 1656 where the bands 1600 may be inserted, and the bands 1600 may form a loop extending through the pilot hole.

The bands 1600 illustrated in FIGS. 16A-16B are provided in a level manner, with the bands 1600 proceeding through corresponding intercostal spaces 1660 on opposite sides of the sternum 1656. However, the bands 1600 may be installed in other ways, with the bands 1600 extending diagonally. For example, some may find it desirable to install two bands 1600 in an X-pattern. Further, bands 1600 are provided with only one band 1600 inserted in each intercostal space 1660, but additional bands 1600 may be provided in a single intercostal space 1660 in other embodiments. Additionally, as shown in FIG. 16A, more than one head may be received in a single window 1624 of the fixation plate 1622. In FIG. 16A, one head is received in the top window 1624, two heads are received in the middle window 1624, and one head is received in the bottom window 1624. In other embodiments, only one head may be received in each window 1624, or additional heads may be inserted into a single window.

While FIGS. 16A-16B show the fixation plate and bands installed on a sternum, a tensioning gun may be used to improve the installation process for the fixation plate and bands. FIG. 17 illustrates a perspective view of an example tensioning gun 1738 being used to assist in securing an example fixation plate 1722 to the sternum of a patient.

Similar to the bands and fixation plates discussed above, the bands 1700 may be inserted through intercostal spaces 1760 between ribs 1758 of the patient to form a loop, and the head of these bands 1700 may be installed at a fixation plate 1722. The end of the bands 1700 may be inserted into a tensioning gun 1738, and the tensioning gun 1738 may apply tension to the bands until a tension limit has been reached. In the illustrated embodiment, gripping jaws 1725 and a travel limiter 1725A are provided. The gripping jaws 1725 may pull on the band 1700 and tighten the band 1700 to a predetermined tension associated with placement of the travel limiter 1725A. However, in other embodiments, other mechanisms may be provided to apply tension to the band 1700 and/or the tension limit may be implemented without using a travel limiter 1725A. Upon the tension limit being reached, the amount of tension applied by the tensioning gun 1738 may be maintained. With the tension at this level, the trim system 1548 (see FIG. 15) within the tensioning gun 1738 may cause the cutting blade 1554 (see FIG. 15) to cut the excess portion of the band 1700. In some embodiments, the bands 1700 may be provisionally tensioned after the bands 1700 are formed into loops. Where provisional tensioning is performed, the loops formed by the bands 1700 may be tightened to some degree while still leaving some slack in the loops. By provisionally tensioning bands, proper positioning of the severed halves of the sternum, the fixation plate 1722, and the bands 1700 may be ensured before tension is applied via the tensioning gun 1738. However, in other embodiments, provisional tensioning may not be performed. Tensioning of the bands 1700 with the tensioning gun 1738 may simultaneously compress the fixation plate 1722 and bone components together to effectively form a splint that may provide adequate stability for healing. The fixation plate 1722 may provide sufficient stiffness and rigidity to buttress the injured bone while providing sufficient ductility to conform to the shape and contours of the underlying bone (e.g. the sternum) upon the tensioning of the bands 1700.

Skipping ahead to FIG. 21, an alternative tensioning gun 2138 is illustrated. The tensioning gun 2138 may take on the form of a "trigger-pull" shape similar to a handgun. The tensioning gun 2138 may include a rotatable knob 2146 on the body 2145 of the tensioning gun 2138, and the rotatable knob 2146 may be located on the end of the tensioning gun 2138 opposite the aperture 2151. The tensioning gun 2138 may include a handle 2140 and an actuator lever 2142. When twisted, the rotatable knob 2146 may operate to adjust the tension setting such that a desirable amount of tension may be generated in a band 1300 when a user depresses the actuator lever 2142. Further, a switch 2153 may also be included. The switch 2153 may enable the tensioning gun 2138 to alternate between a tensioning mode and a cutting mode. Where the switch 2153 is in a tensioning mode, the tensioning gun 2138 may tighten the band 1300 being fed through the aperture 2151 on the distal end of the barrel 2141 when a user squeezes and depresses the actuator lever 2142. Once the tension in band 1300 reaches a desirable or pre-determined level, the switch 2153 may be used to change from the tensioning mode to the cutting mode. In the cutting mode, a user may depress the actuator lever 2142 to cut the tensioned band 1300. The resulting band 1300 may be neatly flush to or beneath the top surface of a head 104 (see FIG. 1E).

Looking now at FIG. 22, another alternative tensioning gun 2238 is illustrated. The tensioning gun 2238 may take the form of a "linear-pull" mechanism shaped similarly to a syringe. In such an embodiment, the actuator lever 2242 may take on a more linear movement profile, and the actuator lever 2242 may function to tension a band 1300 when the user pulls the actuator lever 2242 backwards along a slider track 2255 in a direction away from the aperture 2251. The slider track 2255 may be provided on the barrel 2241 of the body 2245 for the actuator lever 2242. Once the band 1300 reaches the tension limit, a switch 2253 may be utilized to switch the tensioning gun 2238 from a tensioning mode to a cutting mode. In the cutting mode, the user may cut the tensioned band 1300 by pulling the actuator lever 2242 back along the slider track 2255, and the resulting band 1300 may be neatly flush to or beneath the top surface of a head 104 (see FIG. 1E). The tensioning gun 2238 illustrated in FIG. 22 may be a highly intuitive tool, and it may be a disposable, single-use tool in some embodiments. However, the tensioning gun 2238 and other tensioning guns provided herein may be durable tools that may be intended for repeated use in other embodiments.

The actuator lever 2142 of FIG. 21 and the actuator lever 2242 of FIG. 22 may be configured to cause both the actuation of the cutting blade and the application of tension to the band, and the switch 2153, 2254 may be used to control the mode that the actuator lever is in. However, tensioning guns may switch between a cutting mode and a tensioning mode in other ways in other embodiments. For example, the tensioning gun may alternate between the tensioning mode and the cutting mode each time that the actuator lever is compressed. In some embodiments, the tensioning gun may only be used to apply tension up to a tension limit, and another cutting tool may be deployed to cut a band upon the tension limit being reached.

FIGS. 18A-18C provide another illustration of the fixation plate being installed at a cut sternum to assist in restricting two severed halves of the cut sternum. FIG. 18A illustrates a perspective view of an example fixation plate being positioned against a cut sternum. FIG. 18B illustrates a perspective view of the fixation plate of FIG. 18A with a band being assembled to the fixation plate, in accordance with some embodiments discussed herein. FIG. 18C illustrates a perspective view of the fixation plate of FIG. 18A with a tensioning gun being used to tension and cut bands, in accordance with some embodiments discussed herein.

As illustrated in FIG. 18A, the sternum 1856 may include a cut 1857, and two severed halves of the sternum 1856 may be provided on opposite sides of the cut 1857. With the two severed halves of the sternum 1856 being adjusted to the appropriate position, the fixation plate 1822 may be provided at the sternum 1856 above the cut 1857. As illustrated in FIG. 18B, a spring 1859 may be provided at the fixation plate 1822, and the spring 1859 may assist in urging the fixation plate 1822 against the sternum 1856 to conform the shape of the fixation plate 1822 to the shape of the sternum 1856. Manubrial extensions may be provided in the fixation plate 1822 at the upper portion of the fixation plate 1822 to enable the fixation plate 1822 to easily conform to features at the manubrium of the sternum. Furthermore, the spring 1859 may have small wires that may extend through small holes in the sternum. These wires may extend from the top side of the sternum through the sternum to the bottom side of the sternum, and the wires may form a loop that may be tightened at the bottom side of the sternum. The head of a band 1800 may be installed within a window within the fixation plate 1822, and the band 1800 may be wrapped around the sternum 1856 through intercostal spaces 1860 between the ribs 1858 of a patient to form a loop as described herein. This band 1800 may be wrapped around using instruments as illustrated in FIG. 18B, but this may instead be done by hand in other embodiments. Furthermore, as illustrated in FIG. 18C, a tensioning gun 1838 may be used to apply tension to the bands 1800 and to remove excess portions of the bands 1800. Tensioning of the bands 1800 may simultaneously compress the fixation plate 1822 and bone components together to effectively form a splint that may provide adequate stability for healing. The fixation plate 1822 may provide sufficient stiffness and rigidity to buttress the injured bone while providing sufficient ductility to conform to the shape and contours of the underlying bone (e.g. the sternum) upon the tensioning of the bands 1800. The fixation plate 1822 may disperse stress over a larger surface area of the bone components than the bands 1800 applied by themselves.

In some embodiments, a surgical drain assembly may be provided alongside a fixation plate. Surgical drain assemblies may be beneficial in open heart procedures with sternotomy, but the surgical drains may be used for other procedures and may be used alongside bones other than the sternum. Surgical drain assemblies may remove excess fluid such as blood that may collect near a surgical site. If excess fluid is not removed, this excess fluid may become infectious posing serious risk to the health of the patient while retarding or preventing recovery. Surgical drains may be provided on a temporary basis in some embodiments, and the surgical drains may be removed once the surgical site has sufficiently healed.

FIG. 19A illustrates a bottom view of an example surgical drain assembly 1962, FIG. 19B illustrates a side view of the surgical drain assembly 1962, and FIG. 19C illustrates a schematic view of the surgical drain assembly 1962 of FIG. 19A having an internal cavity 1972. As illustrated in FIG. 19A, the surgical drain assembly 1962 may include a drain body 1964. The drain body 1964 may generally have a similar shape to a fixation plate that the drain body 1964 is being used with in some embodiments. However, the drain body 1964 may differ in size and/or shape from the fixation plate in other embodiments. The drain body 1964 is configured to have a similar size and shape as the fixation plate 822 of FIGS. 8A-8D so that the drain body 1964 may easily be attached to the fixation plate 822.

The drain body 1964 may include protrusions 1966 extending downwardly from a bottom surface of the drain body 1964. The protrusions 1966 may be configured to engage with a portion of the windows 824 of the fixation plate 822 (see FIG. 8A) to restrict the movement of the drain body 1964 relative to the fixation plate 822. The protrusions 1966 may form a press fit with a portion of the windows 824, but the drain body 1964 may be restrained relative to the fixation plate 822 in other ways. While the protrusions 1966 generally match the shape of the windows 824 of the fixation plate 822, the protrusions 1966 and other features on the drain body 1964 may be configured to match the features of another fixation plate 822 in other embodiments. For example, contoured sections may be provided in the drain body 1964, or additional protrusions may be provided.

The drain body 1964 may be configured to be placed above a fixation plate 822 (see FIG. 8A) resting on a sternum 1856 (see FIG. 18A). Extension tubes 1970 may connect to the drain body 1964, and the extension tubes 1970 may extend around to the opposite side of the sternum 1856. The extension tubes 1970 may be wrapped through intercostal spaces 1860 (see FIG. 18A) between adjacent ribs 1858 (see FIG. 18A) of the patient. The extension tubes 1970 may collect excess fluid at locations behind the sternum 1856 where excess fluids tend to collect, and this excess fluid may flow through the extension tubes 1970 to an internal cavity 1972 within the drain body 1964. The drain body 1964 and the extension tubes 1970 may comprise soft and flexible material and may comprise an approved implant material such as silicone.

Placement of the drain body 1964 above the fixation plate may be beneficial for various reasons. Placement of the drain body 1964 at this position may permit the drain body 1964 to be easily installed and easily removed. To the extent one desires to remove the surgical drain assembly 1962, the drain body 1964 may be simply removed by gently prying the protrusions 1966 free from the fixation plate 822. This may effectively decouple the drain body 1964 and the fixation plate 822. This removal of the drain body may be done using surgical instruments. Once the drain body 1964 and the fixation plate 822 are decoupled, the surgical drain assembly 1962 may be removed from the body of the patient by shifting the surgical drain assembly 1962 through a small incision where the drainage tube 1968 exits though the skin. Notably, positioning of the drain body 1964 above the sternum 1656 (see FIG. 16A) permits easy removal-if the drain body 1964 were installed behind the sternum 1656, removal of the drain body 1964 is made more difficult. To remove a drain body 1964 installed behind the sternum 1656, one would need to grasp the drain body 1964 (which is positioned in a hard to reach location behind the sternum 1656), maneuver the drain body 1964 through an intercostal space 1660 (see FIG. 16A) between the ribs 1658 (see FIG. 16A), and then maneuver the drain body 1964 to an incision in the skin of the patient where the drain body 1964 may be removed. Such an approach would be more difficult and would potentially require a larger incision to better enable one to remove the drain body 1964. Furthermore, installation and removal of a drain body 1964 at a position behind the sternum 1656 may be problematic due to the presence of other organs located behind the sternum 1656. By placing the drain body 1964 above the sternum 1656, these issues may be avoided, and smaller extension tubes 1970 may be more easily wrapped around through the intercostal spaces 1660 (see FIG. 16A) to capture excess fluid from behind the sternum 1656.

Fluid may be retained in the internal cavity 1972 until it is removed via a drainage tube 1968. This drainage tube 1968 may be provided at or proximate to the bottom of the drain body 1964 when the drain body 1964 is in an upright position (e.g. when the patient is standing up). Thus, the force of gravity may urge fluids in the drain body 1964 to flow to the drainage tube 1968 where they may be removed. However, in some embodiments, multiple drainage tubes 1968 may be connected to the drain body 1964. Additionally, drainage tubes 1968 may be provided at other locations on the drain body 1964. In some embodiments, the drainage tube 1968 may extend to an external environment from within the body of the patient, passing through layers of flesh.

The force of gravity may be relied on exclusively in some embodiments to urge fluids to the drainage tube 1968. However, in other embodiments, a negative pressure device may be utilized to urge fluid to and through the drainage tube 1968. The negative pressure device may also tend to urge fluid through any openings 1976 (see FIG. 19E) in the drain body 1964, and the negative pressure device may tend to urge fluid through the extension tubes 1970 so that fluid may flow into the internal cavity 1972 and out of the drainage tube 1968. A negative pressure device (manually or mechanically actuated) can be attached to the free end of the drainage tube 1968. This negative pressure device may create suction throughout the surgical drain assembly 1962 to assist in the removal of excess fluid. In some embodiments, manually actuated negative pressure devices such as syringes or hand pumps may be used. Negative pressure does not rely of gravity feed to remove excess fluid, so the negative pressure device may permit excess fluid removal while the patient is resting, for example, in a supine position. However, the negative pressure device may be used in conjunction with gravitational forces to remove excess fluid in some embodiments. Alternatively, an inlet tube may be provided, and a positive pressure device may be installed at the inlet to urge excess fluid towards the drainage tube 1968 and out of the surgical drain assembly 1962.

While the drain body 1964 of FIG. 19A includes protrusions 1966 to assist in restraining the drain body 1964 relative to a fixation plate, other approaches for restraining these two components are also contemplated. For example, FIG. 19D illustrates an enhanced view of an example drain body 1964 of a drainage assembly 1962 having suture holes

1974. Suture holes 1974 may be provided on the drain body 1964 and the fixation plate, and the drain body 1964 and the fixation plate may be stitched together using the suture holes 1974. Suture holes 1974 may be provided generally parallel to the lateral edges of the fixation plate. A surgical suture may extend through the suture holes 1974 to bind the drain body 1964 and a fixation plate 822 (see FIG. 8A) together, and the surgical suture may eventually be knotted and/or cut. However, other fasteners may be used. In some embodiments, multiple surgical sutures may be used to provide increased security. In some embodiments, the surgical sutures and suture holes 1974 may be used instead of the protrusions 1966 to attach the drain body 1964 and fixation plate 822 together, but these different approaches could be used simultaneously to provide further security in some embodiments. Additionally, in other embodiments, the fixation plate and the drain body 1964 may form one integral part.

Extension tubes may be used to provide obtain excess fluid, but the drain body may also include openings where fluid may flow through to enter the internal cavity of the drain body. FIG. 19E illustrates an enhanced view of an example drain body 1964 having a plurality of openings 1976 in the surface of the drain body 1964. Openings 1976 having larger or smaller sizes may be used in other embodiments. Furthermore, while the openings 1976 are illustrated as having a circular shape in FIG. 19E, the openings 1976 may have other shape in other embodiments (e.g. rectangular slits, oval shaped, asymmetrically shaped, etc.). Openings 1976 may be provided on the top surface of the drain body 1964 so that fluid at the fixation plate may flow through the windows or other gaps to the openings 1976 so that the fluid may enter into the internal cavity 1972. Additionally, openings 1976 may be provided on other surfaces of the drain body 1964 and/or extension tubes 1970. Suction or other forces applied at an inlet tube or a drainage tube may tend to urge excess fluid through the openings and into the internal cavity of the drain body 1964. The openings 1976 may be positioned on the drain body 1964 to receive fluid when a user is lying down, but similar openings may be provided at other locations on the drain body 1964 to receive fluid when the user is standing up.

While the surgical drain assembly 1962 may be used primarily as a drain in some embodiments, it may additionally or alternatively be used to introduce antiseptic and/or other fluids to post-operatively flush the surgical site. In addition, medications may be introduced to a surgical site post-operatively using the surgical drain assembly 1962. For example, an inlet tube (see, e.g., 1969, FIG. 19G) may be provided where medications may be introduced, and positive pressure may be generated by gravity, a syringe, a hand pump, or some other device to urge the medications towards the surgical drain assembly and the surgical site. Positive pressure for introducing fluids may be generated by gravity feed such as an elevated IV bag or via a syringe or hand pump or a mechanical device. The introduced medication fluid may eventually be removed with the application of a negative pressure (manual or mechanical) device applied at the drainage tube 1968 or gravity feed. Additionally or alternatively, some or all of the surgical drain assembly 1962 (e.g. the surface of the drain body 1964) may be coated with antimicrobial agents that release into the surrounding in-vivo environment.

Looking now at FIGS. 19F-19G, another example embodiment of a drain assembly 1962 is illustrated. FIG. 19F illustrates a bottom view of the drain assembly 1962, and FIG. 19G illustrates a top view of the drain assembly 1962. The drain assembly 1962 may include a drain body 1964. The drain body of FIGS. 19F-19G may generally match the shape of the sternum for a patient. The drain body 1964 may include one or more protrusions 1966 that extend downwardly from the bottom surface of the drain body 1964. The protrusions 1966 may be configured to engage with a portion of the windows 824 of the fixation plate 822 (see FIG. 8A) to restrict the movement of the drain body 1964 relative to the fixation plate 822. The protrusions 1966 may form a press fit with a portion of the windows 824, but the drain body 1964 may be restrained relative to the fixation plate 822 in other ways. For example, protrusions may be provided on the drain body 1964 that are configured to engage with the outer perimeter of the fixation plate 822. Additional protrusions may be provided on the bottom surface of the drain body 1964 that are configured to engage with the sternum itself, and these protrusions may extend at least partially into intercostal spaces 1660 (see FIG. 16A) between the ribs 1658 (see FIG. 16A) of the patient to assist in positioning the drain body 1964. Similar to the drain assembly of FIG. 19A, the drain assembly 1962 in FIGS. 19F and 19G may include extension tubes 1970. However, a drain assembly may be provided without extension tubes in some embodiments. The extension tubes 1970 may extend into intercostal spaces 1660 between the ribs 1658 of the patient so that the extension tubes 1970 reach the area behind the sternum of the patient where excess fluid tends to collect. The extension tubes 1970 may be pre-bent or curved at a pre-determined radius. This may help facilitate maneuverability of the bands 100 through and under the intercostal spaces 1660 and under the posterior surface of the sternum. The extension of extension tubes 1970 into the intercostal spaces 1660 may aid in the positioning of the drain body 1964. The drain assembly 1962 may also include an inlet tube 1969 and a drainage tube 1968.

While various embodiments described herein illustrate or describe the use of the fixation plate, bands, the tensioning device, and/or the drain assembly with a severed sternum, these components may be used with other bones in the human body, or these components may be used for bones of an animal. The fixation plate and bands described herein may be formed from any polymeric material known in the art. The polymeric material should preferably have some rigidity and some flexibility. In an embodiment, the polymeric material used to form the fixation plate and/or the bands may comprise polyether ether ketone (PEEK). The polymeric material may be thermoformed, 3D printed, or formed using any other method known in the art. Additionally, the drain assembly may comprise a variety of materials. Drain assemblies may comprise an elastic material in some embodiments that may be easily conformed to the shape of the sternum. For example, the drain assembly may comprise a silicone, another soft rubber based material, or a polymeric material such as PEEK. The material in the drain assemblies may be porous on some or all sides so that excess fluid may enter into the drain assembly through the material, and suction may be applied to the drain assembly to urge excess fluid into the drain assembly through the porous material.

While various apparatuses and assemblies are provided, methods for using these apparatuses and assemblies are also contemplated. FIG. 20 illustrates an example method for installing a fixation plate and a drainage assembly to a severed sternum, in accordance with some embodiments discussed herein. At operation 2002, a tensioning gun, a fixation plate, bands, and a surgical drain assembly may be provided. In some embodiments, these components may not be provided. For example, where a user desires to install the fixation plate without any surgical drain assembly, the surgical drain assembly may be omitted.

At operation 2004, a fixation plate and a drain body of the surgical drain assembly may be attached. The fixation plate and the drain body may be attached together to increase the ease of installation on the severed sternum. By attaching these components together, fewer moving parts may exist during installation.

At operation 2006, the fixation plate and the drain body may be placed on the severed sternum above the cut. The fixation plate may be positioned on the sternum with the drain body positioned above the fixation plate. The two severed halves of the severed sternum may need to have their positions adjusted before placement of the fixation plate and drain body to ensure proper healing.

At operations 2008-2012, bands may be applied and tensioned. At operation 2008, bands may be applied to the fixation plate. This may be done by placing a portion of the bands (e.g. the head) within windows of the fixation plate so that the movement of the bands may be restricted relative to the fixation plate. The end of the tail of a band may be inserted into an internal cavity at the head of the band so that a loop is formed. At operation 2010, bands may be provisionally tensioned. This provisional tensioning may be done by hand or some other instrument. Multiple bands may be applied and provisionally tensioned to ensure that the fixation plate and bands are positioned appropriately before performing any final tensioning. At operation 2012, final tensioning may be applied to the bands. This final tensioning may be performed using the tensioning gun. The tensioning gun may be configured to apply tensioning until the tension within the band reaches a tension limit, and the tensioning gun may cease applying further tension to the bands once this tension limit is reached. Alternatively, the tensioning may continue being applied at the same tension level proximate to the tension limit, until the bands are cut at operation 2014. At operation 2014, the bands may be cut. Where the tensioning gun is used, the bands may be cut automatically upon the desired tension level being reached within a band.

The operations of FIG. 20 may be performed in any order unless otherwise noted. For example, Furthermore, the operations of FIG. 20 may be performed simultaneously in some embodiments. For example, operations 2012 and 2014 may be performed simultaneously where a tensioning gun is used to simultaneously perform final tensioning and cutting, and this may be beneficial to increase the ease of installation as it reduces the number of separate tasks that need to be performed by the installer. Additionally, certain operations of FIG. 20 may be omitted or certain operations may be added to FIG. 20. For example, in some embodiments, no drain body is provided at operation 2004 and only a fixation plate may be provided instead. In other embodiments, provisional tensioning is not performed and the user may simply apply final tensioning at operation 2012.

In some embodiments, fixation plates may be provided with additional holes configured to receive further fasteners, and this may be beneficial to cause the fixation plate to further conform to the shape of the underlying bone. FIG. 23 illustrates a fixation plate 2322 with holes 2363 provided within rails 2326. These holes 2363 are configured to receive fasteners, and these fasteners may extend through the holes 2363 and engage a bone. By engaging a bone, fasteners may assist in attaching the fixation plate 2322 to the underlying bone. Fasteners may also assist in forcing the fixation plate 2322 to change in shape to conform to the shape of the underlying bone. Fasteners inserted through holes 2363 may include screws, wires, sutures, cables, etc. Holes 2363 may be threaded in some embodiments, but the holes 2363 may be provided without any threading in other embodiments. Furthermore, in some embodiments, the holes 2363 may be configured to receive a fastener in the form of a wire, and the wire may be inserted into a bone to restrict movement of the fixation plate. Alternatively, the wire could simply be wrapped around a bone to further aid in restricting movement of the fixation plate. By providing holes 2363, additional fasteners may be received in the holes to reduce the amount of forces acting on each individual fastener and on any bands that are attached to the fixation plate 2322, and this may reduce the likelihood of failure in the bands and fasteners. The fixation plate 2322 may possess other features of the various embodiments of fixation plates described herein and illustrated in the drawings.

In various embodiments, a head of a band may passively engage windows formed in a fixation plate, and movement of the band out of the windows may be at least partially restricted once tension is applied to the band. FIGS. 24A-24B illustrate examples of such passively engaging heads. FIG. 24A illustrates a top perspective view of a head 2404 of a band 2400 that is passively engaged with a fixation plate 2422, and FIG. 24B illustrates a bottom view of a head 2404 of a band 2400 that is passively engaged with a fixation plate 2422. As illustrated, bands 2400 may be provided having a head 2404 and a tail 2402. The head 2404 is passively engaged with windows 2424 formed in the fixation plate 2422. As illustrated in the bottom view of FIG. 24B, the bottom portion 2465 may simply rest within the window 2424—this may be done without any protruding portion 626A (see FIG. 6B) extending from the rails 2426 into the window, and this may be done without any bottom lock 120 (see FIG. 1E) being provided on the bottom portion 2465. When the band 2400 has not been tightened, the bottom portion 2465 is configured to be easily removed from the window 2424 with minimal interference. However, when the band 2400 has been tightened around a bone or some other object, tension forces may act on the band 2400 and urge the head 2404 of the band 2400 downwardly into the windows 2424. This downward force acting on the head 2404 of the band 2400 will retain the head 2404 of the band 2400 within the windows 2424. In some instances, the head 2404 of the band 2400 may still be able to slide along the windows 2424 after tensioning. However, in some instances, the downward force acting on the head 2404 may cause a significant amount of friction between the head 2404 and the fixation plate 2422, and this friction may wholly prevent or partially restrict the movement of the head 2404 along a window 2424.

FIGS. 24C and 24D illustrate further views of the head 2404 where the bottom portion 2465 may be seen in more detail. FIG. 24C illustrates a top perspective view of the head 2404 of the band 2400 of FIG. 24A, and FIG. 24D illustrates a bottom perspective view of the head 2404 of the band 2400 of FIG. 24A. The illustrated band 2400 has a tail 2402 and a head 2404, and an bottom portion 2465 is provided at the bottom of the head 2404. The bottom portion 2465 includes circular shape, but other shapes may be provided. Notably, the bottom portion 2465 does not include any sort of bottom lock (see, e.g., bottom lock 120 of FIG. 1E, bottom lock 220 of FIG. 2C) or any tabs extending radially from the center of the bottom portion 2465. Thus, where no other forces are acting on a head 2402, the bottom portion 2465 of the head 2402 may be easily raised and lowered out of the windows 2424 without any significant interference between the bottom portion 2465 and the rails 2426.

In FIGS. 24C and 24D, the bottom portion 2465 is configured to permit rotation of the band 2400 relative to a fixation plate 2422. As illustrated in FIG. 24C, the bottom portion 2465 generally possesses a circular shape. With this shape, the bottom portion 2465 may be inserted into the window 2424 (see FIG. 24A). When received in the window 2424, the circular shaped bottom portion 2465 may be configured to permit rotation of the band 2400 relative to the fixation plate 2422 when the amount of tension applied in the band 2400 is low. However, when a high amount of tension is applied to the band 2400, the ability of the band 2400 to rotate relative to the fixation plate 2422 may be partially or wholly restricted. The use of circular shaped bottom portions 2465 may be advantageous to provide increased flexibility while assembling the band 2400 to the fixation plate 2422. While a circular shaped bottom portion 2465 is provided as one example of an bottom portion that is configured to rotate, the bottom portion may still rotate when possessing other shapes (depending on the shape of the window that the bottom portion is being received in).

FIG. 24E illustrates a bottom view of the fixation plate 2422 of FIG. 24A. As illustrated, the fixation plate 2422 may include rails 2426 running along the sides of the fixation plate 2422. Windows 2424 may be formed in spaces between the rails 2426. In the fixation plate 2422 of FIG. 24A, the windows 2424 may be formed without any protruding portion 626A (see FIG. 6B) that extends into the windows 2424. Thus, where no other forces are acting on a head 2402, the bottom portion 2465 of the head 2402 may be easily raised and lowered out of the windows 2424 without any significant interference between the head 2402 and the rails 2426.

In some embodiments, bands may be provided having passively engaging heads that are configured to restrict rotation of bands relative to a fixation plate. FIG. 25A illustrates a top perspective view of a head 2504 of a band 2500 that is passively engaged with a window 2524 of a fixation plate 2522, and FIG. 25B illustrates a bottom view of a head 2504 of a band 2500 that is passively engaged with a window 2524 of a fixation plate 2522. As illustrated, the fixation plate 2522 may include rails 2526 running along the sides of the fixation plate 2522. Windows 2524 may be formed in spaces between the rails 2526. The bands 2500 have a head 2504 and a tail 2502.

In FIGS. 25A-25B, the bottom portion 2565 is configured to restrict rotation of the band 2500 relative to the fixation plate 2522. As illustrated in FIG. 25B, the bottom portion 2565 generally possesses a square shape. With this shape, the bottom portion 2565 may be inserted into the window 2524. When received in the window 2524, the square shaped bottom portion 2565 may be configured to restrict rotation of the band 2500 relative to the fixation plate 2522—an attempt to rotate the square shaped bottom portion 2565 in a clockwise or counterclockwise direction will result in contact between the edges of the bottom portion 2565 and the rails 2526.

Further views of the square shaped bottom portion 2565 in isolation are provided in FIGS. 25C and 25D. FIG. 25C illustrates a bottom perspective view of the head 2504 of the band 2500, and FIG. 25D illustrates a top perspective view of the head 2504 of the band 2500. Fillets may be provided at the corners of the square shaped bottom portion 2565, and the fillets may reduce the likelihood of stress concentrations at the corners of the bottom portion 2565. While the square shaped bottom portion 2565 is illustrated, the bottom portion 2565 may possess other shapes. For example, where it is desirable to use a band 2500 having an bottom portion that is configured to restrict rotation of the band 2500, bottom portions may possess a triangular shape, rectangular shape, a pentagonal shape, a hexagonal shape, an octagonal shape, a star shape, a polygonal shape, an asymmetrical shape, or some other non-circular shape. The band 2500 may be configured so that the band 2500 will not slip, move, or change position due to the passive engagement of the head 2504.

In some embodiments, the head may possess a bottom lock that possesses a cam shape. The head may be restricted from moving out of the windows at one rotational orientation, and the head may be permitted to move out of the windows at another rotational orientation.

FIGS. 26C and 26D illustrate the head having a cam shaped bottom lock in isolation. FIG. 26C illustrates a bottom perspective view of the head 2604 of FIG. 26A. FIG. 26D illustrates a bottom view of the head 2604 of FIG. 26A. The cam shaped bottom lock 2620 may possess an enlarged portion 2667A and reduced portions 2667B. The enlarged portion 2667A may take the form of winged tabs. The edges of the enlarged portion 2667A may extend farther away from the center of the cam shaped bottom lock than the edges of the reduced portions 2667B. A lip 2675 may be formed at the enlarged portions 2667A, and a fixation plate 2622 (see FIG. 26B) may be retained between the lip 2675 and the upper portions of the head 2604. As illustrated in FIG. 26C, the band 2600 may also have a tail 2602.

FIGS. 26A and 26B illustrate an example of such a head 2604 interacting with a fixation plate 2622. FIG. 26A illustrates a bottom view of a head 2604 of a band 2600 that includes a cam shaped bottom lock 2620 in an open position relative to a fixation plate 2622. FIG. 26B illustrates another bottom view of the head 2604 in a closed position relative to the fixation plate 2622. The fixation plate 2622 possesses protruding portions 626A (see FIG. 6B) that extend into the windows 2624, and these protruding portions 626A may assist in engaging an enlarged portion 2667A of the bottom lock 2620. The cam shaped bottom lock 2620 may be received in a window 2624 of the fixation plate 2622. This may be done with the cam shaped bottom lock 2620 oriented such that the enlarged portion 2667A will not interfere with the fixation plate 2622. Once the bottom lock 2620 is received within the window 2624, the bottom lock 2620 may be rotated so that the enlarged portions 2667A of the bottom lock 2620 come in contact with the fixation plate 2622 as illustrated in FIG. 26B. Contact between the enlarged portions 2667A and the fixation plate 2622 will prevent the band 2600 from moving out of the windows 2624. In some embodiments, contact between the enlarged portions 2667A and the fixation plate 2622 may generate friction to at least partially restrict movement of the bands 2600 along the length of the windows 2624 (e.g. up and down in FIG. 26B). In some embodiments, this friction may be large enough to effectively lock the band 2600 in place relative to the fixation plate 2622. The bottom lock 2620 may be rotated by ninety (90) degrees in a clockwise or counterclockwise direction to lock and/or unlock the head 2604 relative to the fixation plate 2622 in some embodiments. The cam shaped bottom lock may possess a variety of shapes. For example, the cam shaped member may possess an oval shape, a polygonal shape, an asymmetrical shape, etc. The bottom lock 120 illustrated in FIGS. 1C and 1D may act as a cam shaped bottom lock, and this bottom lock 120 may function similarly to the bottom lock 2620.

While various embodiments provide fixation plates having windows configured to allow a head of a fastener to slide along the windows, other fixation plates are contemplated having windows that do not permit the head of a fastener to slide. FIGS. 27 and 28 illustrate two such embodiments. FIG. 27 illustrates a top view of a fixation plate 2722 with circular windows 2771. FIG. 28 illustrates a top view of a fixation plate 2822 with square windows 2871.

Looking first at FIG. 27, the circular windows 2771 may receive a portion of a head of a band. The circular windows 2771 are configured to restrict translatory movement of the head of the band in a lengthwise direction along the fixation plate 2722 (e.g. left and right in FIG. 27) or in a traverse direction (e.g. up and down in FIG. 27). Thus, the head may be locked in position in this regard. However, circular windows 2771 may be configured to permit the head of a band 2700 received therein to rotate relative to the fixation plate 2722. This rotational movement of the head of the band 2700 may be beneficial to permit bands 2700 to be rotated as necessary so that the band 2700 may extend into an intercostal space 1660 (see FIG. 16A) between ribs 1658 (see FIG. 16A).

Looking now at FIG. 28, the square windows 2871 of the fixation plate 2822 may receive a portion of a head of a band. The square windows 2871 are configured to restrict translatory movement of the head of the band in a lengthwise direction along the fixation plate 2822 (e.g. left and right in FIG. 28) or in a traverse direction (e.g. up and down in FIG. 28). Thus, the head may be locked in position in this regard. Furthermore, depending on the shape of an bottom portion or a head of a band, the square windows 2871 may be configured to prevent the head of a band received therein from rotating relative to the fixation plate 2822. For example, where an appropriately sized head having a square shaped bottom portion 2565 (see FIG. 25C) is received in a square window 2871, this may prevent translatory movement and rotational movement of the head. While the square windows 2871 are illustrated, the windows may possess other shapes. For example, windows may possess a triangular shape, rectangular shape, a hexagonal shape, a star shape, a polygonal shape, an asymmetrical shape, or some other non-circular shape. The windows may be designed to generally match the shape of the bottom portion of a corresponding head.

The fixation plate 2722 and fixation plate 2822 do not have any protruding portion 626A (see FIG. 6B). Thus, the head of bands may be passively engaged with fixation plates 2722 and fixation plate 2822. Once tension is applied to the bands, the head of the bands may be urged towards the fixation plate to retain the head of the bands within the windows. However, in other embodiments the fixation plate 2722 or the fixation plate 2822 may include protruding portions 626A (see FIG. 6B) that extend into the windows, and bands may be used having a bottom lock 120 (see FIG. 1E) that may engage the protruding portions.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the invention. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the invention. In this regard, for example, different combinations of elements and/or functions than those explicitly described above are also contemplated within the scope of the invention. Although specific terms are employed herein, they are used in a generic and descriptive sense only and not for purposes of limitation.

That which is claimed:

1. A plate assembly for stabilizing a bone, comprising:
a fixation plate having rails that form a window;
a band having
  a tail; and
  a head defining an internal cavity being configured to receive a portion of the tail,
wherein the head includes a bottom portion that does not include radially extending tabs; and
wherein the fixation plate is configured to be positioned proximate to a bone, wherein the head is configured to be at least partially received at the fixation plate between the rails within the window, wherein the band is configured to be wrapped around the fixation plate and the bone, wherein the internal cavity of the head is configured to receive an end of the tail to form a loop, wherein the band is configured to receive a tension force to tighten the loop formed by the band, and wherein a shape of the bottom portion and a shape of the window are both configured to permit the band to rotate relative to the window when no tension is being applied to the band.

2. The plate assembly of claim 1, wherein the bottom portion is configured to be passively received within the window.

3. The plate assembly of claim 2, wherein the head is configured to be selectively removable from the window when no loop has been formed by the band, and wherein the band is configured to urge the head towards the fixation plate upon tightening of the loop formed by the band.

4. The plate assembly of claim 2, wherein the window possesses an elongate shape that is configured to permit the head to slide along the rails forming the window.

5. The plate assembly of claim 4, wherein translatory movement of the band is at least partially restricted upon tightening of the loop formed by the band.

6. The plate assembly of claim 2, wherein a shape of the bottom portion and a shape of the window are both configured to prevent the band from rotating relative to the window when no tension is being applied to the band.

7. The plate assembly of claim 6, wherein the bottom portion has a square shape, a triangular shape, a rectangular shape, a pentagonal shape, a hexagonal shape, an octagonal shape, or a star shape.

8. The plate assembly of claim 6, wherein the bottom portion has a square shape.

9. The plate assembly of claim 2, wherein a shape of the bottom portion matches the shape of the window, and wherein receipt of the bottom portion in the window is configured to prevent translatory movement of the bottom portion relative to the window.

10. The plate assembly of claim 9, wherein receipt of the bottom portion in the window is configured to prevent rotational movement of the bottom portion relative to the window.

11. The plate assembly of claim 1, wherein the bottom portion has a circular shape.

12. The plate assembly of claim 1, wherein the fixation plate includes one or more holes, and wherein the one or more holes are configured to receive one or more additional fasteners.

13. The plate assembly of claim 12, wherein the one or more additional fasteners include at least one of a screw, a wire, or a suture.

14. The plate assembly of claim 1, wherein the window possesses an elongate shape that is configured to permit the head to slide along the rails forming the window.

15. The plate assembly of claim 1, wherein the head includes a bottom lock, wherein the bottom lock possesses a cam shape with reduced portions and enlarged portions, and wherein edges of the enlarged portions extend farther away from a center of the bottom lock than edges of the reduced portions.

16. A plate assembly for stabilizing a bone, comprising:
a fixation plate having rails that form a window;
a band having
   a tail; and
   a head defining an internal cavity being configured to receive a portion of the tail,
wherein the fixation plate is configured to be positioned proximate to a bone, wherein the head is configured to be at least partially received at the fixation plate between the rails within the window, wherein the band is configured to be wrapped around the fixation plate and the bone, wherein the internal cavity of the head is configured to receive an end of the tail to form a loop, wherein the band is configured to receive a tension force to tighten the loop formed by the band, wherein the head includes a bottom lock having radially extending tabs, wherein the rails have protruding portions that extend into the window, wherein a portion of the head is configured to be received within the window, and wherein the bottom lock is configured to engage the protruding portions to restrict the head from being removed from the window.

17. The plate assembly of claim 16, wherein the bottom lock possesses a cam shape with reduced portions and enlarged portions, and wherein edges of the enlarged portions extend farther away from a center of the bottom lock than edges of the reduced portions.

18. The plate assembly of claim 17, wherein the band is configured to rotate between an open position and a closed position, wherein the bottom lock is oriented relative to the fixation plate such that the head is capable of being removed from the fixation plate when the band is in an open position, and wherein the bottom lock is oriented relative to the fixation plate such that the head is not capable of being removed from the fixation plate when the band is in a closed position.

19. The plate assembly of claim 16, wherein the window possesses an elongate shape that is configured to permit the head to slide along the rails forming the window.

* * * * *